US008382818B2

(12) United States Patent
Davis et al.

(10) Patent No.: US 8,382,818 B2
(45) Date of Patent: *Feb. 26, 2013

(54) OSTIUM SUPPORT FOR TREATING VASCULAR BIFURCATIONS

(75) Inventors: H. Richard Davis, Coral Springs, FL (US); Aaron Kaplan, Norwich, VT (US)

(73) Assignee: Tryton Medical, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,193

(22) Filed: Jul. 1, 2010

(65) Prior Publication Data

US 2011/0004291 A1    Jan. 6, 2011

Related U.S. Application Data

(60) Provisional application No. 61/222,744, filed on Jul. 2, 2009, provisional application No. 61/243,433, filed on Sep. 17, 2009.

(51) Int. Cl.
*A61F 2/06* (2006.01)
(52) U.S. Cl. ..................................... 623/1.16
(58) Field of Classification Search .......... 606/108, 606/194, 200; 623/1.11, 1.15, 1.16
See application file for complete search history.

(56) References Cited

U.S. PATENT DOCUMENTS

| 4,950,227 A | 8/1990 | Savin et al. |
| 4,958,634 A | 9/1990 | Jang |
| 4,994,071 A | 2/1991 | MacGregor |
| 5,071,406 A | 12/1991 | Jang |
| 5,074,845 A | 12/1991 | Miraki et al. |
| 5,102,417 A | 4/1992 | Palmaz |
| 5,226,889 A | 7/1993 | Sheiban |
| 5,304,132 A | 4/1994 | Jang |
| 5,342,387 A | 8/1994 | Summers |
| 5,383,892 A | 1/1995 | Cardon et al. |
| 5,395,333 A | 3/1995 | Brill |
| 5,415,635 A | 5/1995 | Bagaoisan et al. |
| 5,507,769 A | 4/1996 | Marin et al. |
| 5,522,882 A | 6/1996 | Gaterud et al. |
| 5,540,712 A | 7/1996 | Kleshinski et al. |
| 5,575,817 A | 11/1996 | Martin |
| 5,593,442 A | 1/1997 | Klein |
| 5,607,444 A | 3/1997 | Lam |
| 5,609,605 A | 3/1997 | Marshall et al. |
| 5,609,627 A | 3/1997 | Goicoechea et al. |

(Continued)

FOREIGN PATENT DOCUMENTS

| EP | 0712614 B1 | 5/1996 |
| EP | 0505686 | 11/1996 |

(Continued)

OTHER PUBLICATIONS

A New Team to Fight Arterial Disease, *Building Innovation& Construction Technology*, No. 10, Dec. 1999, http://www.cmit.csiro.au/innovation/1999-12/arterial.htm.

(Continued)

*Primary Examiner* — Ryan Severson
*Assistant Examiner* — Ashley Cronin
(74) *Attorney, Agent, or Firm* — Knobbe, Martens, Olson & Bear LLP

(57) ABSTRACT

A prosthesis is disclosed for placement across an ostium opening from a main body lumen to a branch body lumen. The prosthesis comprises a radially expansible support at one end, a circumferentially extending link at the other end and at least one frond extending axially therebetween. The circumferential link can comprise a catheter securement portion and a frond engagement portion.

24 Claims, 44 Drawing Sheets

U.S. PATENT DOCUMENTS

| | | |
|---|---|---|
| 5,613,980 A | 3/1997 | Chauhan |
| 5,628,783 A | 5/1997 | Quiachon et al. |
| 5,632,762 A | 5/1997 | Myler |
| 5,632,772 A | 5/1997 | Alcime et al. |
| 5,632,840 A | 5/1997 | Campbell |
| 5,645,560 A | 7/1997 | Crocker et al. |
| 5,656,036 A | 8/1997 | Palmaz |
| 5,658,251 A | 8/1997 | Ressemann et al. |
| 5,662,608 A | 9/1997 | Imran et al. |
| 5,669,924 A | 9/1997 | Shaknovich |
| 5,669,932 A | 9/1997 | Fischell et al. |
| 5,713,917 A | 2/1998 | Leonhardt et al. |
| 5,718,712 A | 2/1998 | Bonnal et al. |
| 5,720,724 A | 2/1998 | Ressemann et al. |
| 5,720,735 A | 2/1998 | Dorros |
| 5,741,325 A | 4/1998 | Chaikof et al. |
| 5,749,825 A | 5/1998 | Fischell et al. |
| 5,749,851 A | 5/1998 | Wang |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,778 A | 5/1998 | Kleshinski |
| 5,755,781 A | 5/1998 | Jayaraman |
| 5,788,708 A | 8/1998 | Hegde et al. |
| 5,810,871 A | 9/1998 | Tuckey et al. |
| 5,824,052 A | 10/1998 | Khodrsvi et al. |
| 5,827,320 A | 10/1998 | Richter et al. |
| 5,843,116 A | 12/1998 | Crocker et al. |
| 5,855,598 A | 1/1999 | Pinchuck |
| 5,860,998 A | 1/1999 | Robinson et al. |
| 5,868,777 A | 2/1999 | Lam |
| 5,868,783 A | 2/1999 | Tower |
| 5,891,191 A | 4/1999 | Stinson |
| 5,893,887 A | 4/1999 | Jayaraman |
| 5,897,588 A | 4/1999 | Hull et al. |
| 5,906,640 A | 5/1999 | Penn et al. |
| 5,906,641 A | 5/1999 | Thompson et al. |
| 5,922,019 A | 7/1999 | Hankh et al. |
| 5,961,546 A | 10/1999 | Robinson et al. |
| 5,964,771 A | 10/1999 | Beyar et al. |
| 5,967,971 A | 10/1999 | Bolser |
| 5,968,089 A | 10/1999 | Krajicek |
| 5,972,017 A | 10/1999 | Berg et al. |
| 5,976,181 A | 11/1999 | Whelan et al. |
| 5,980,532 A | 11/1999 | Wang |
| 6,004,347 A | 12/1999 | McNamara et al. |
| 6,017,363 A | 1/2000 | Hojeibane |
| 6,027,486 A | 2/2000 | Crocker et al. |
| 6,027,517 A | 2/2000 | Crocker et al. |
| 6,033,434 A | 3/2000 | Borghi |
| 6,033,435 A | 3/2000 | Penn et al. |
| 6,048,361 A | 4/2000 | Von Oepen |
| 6,051,020 A | 4/2000 | Goiechea et al. |
| 6,053,913 A | 4/2000 | Tu et al. |
| 6,053,941 A | 4/2000 | Lindenburg et al. |
| 6,056,775 A | 5/2000 | Borghi et al. |
| 6,056,776 A | 5/2000 | Lau et al. |
| 6,066,155 A | 5/2000 | Amann et al. |
| 6,066,168 A | 5/2000 | Lau et al. |
| 6,068,654 A | 5/2000 | Berg et al. |
| 6,068,655 A | 5/2000 | Sequin et al. |
| 6,077,297 A | 6/2000 | Robinson et al. |
| 6,090,127 A | 7/2000 | Globerman |
| 6,090,133 A | 7/2000 | Richter et al. |
| 6,096,071 A | 8/2000 | Yadav |
| 6,096,073 A | 8/2000 | Webster et al. |
| 6,099,497 A | 8/2000 | Adams et al. |
| 6,099,560 A | 8/2000 | Penn et al. |
| 6,113,607 A | 9/2000 | Lau et al. |
| 6,120,523 A | 9/2000 | Crocker et al. |
| 6,127,597 A | 10/2000 | Beyar et al. |
| 6,129,738 A | 10/2000 | Lashiniski et al. |
| 6,156,052 A | 12/2000 | Richter et al. |
| 6,159,238 A | 12/2000 | Killion et al. |
| 6,162,243 A | 12/2000 | Gray et al. |
| 6,165,195 A | 12/2000 | Wilson et al. |
| 6,168,617 B1 | 1/2001 | Blaeser et al. |
| 6,183,509 B1 | 2/2001 | Dibie |
| 6,206,910 B1 | 3/2001 | Berry et al. |
| 6,210,429 B1 | 4/2001 | Vardi et al. |
| 6,214,036 B1 | 4/2001 | Letendre et al. |
| 6,221,080 B1 | 4/2001 | Power |
| 6,221,096 B1 | 4/2001 | Aiba et al. |
| 6,221,098 B1 | 4/2001 | Wilson et al. |
| 6,231,543 B1 | 5/2001 | Hegde et al. |
| 6,241,738 B1 | 6/2001 | Dereume |
| 6,241,744 B1 | 6/2001 | Imran et al. |
| 6,254,593 B1 | 7/2001 | Wilson |
| 6,258,116 B1 | 7/2001 | Hojeibane |
| 6,261,305 B1 | 7/2001 | Marotta et al. |
| 6,261,316 B1 | 7/2001 | Shaolian et al. |
| 6,264,682 B1 | 7/2001 | Wilson et al. |
| 6,264,686 B1 | 7/2001 | Rieu et al. |
| 6,267,783 B1 | 7/2001 | Letendre et al. |
| 6,270,525 B1 | 8/2001 | Letendre et al. |
| 6,280,412 B1 | 8/2001 | Pederson, Jr. et al. |
| 6,287,315 B1 | 9/2001 | Wijeratne et al. |
| 6,287,336 B1 | 9/2001 | Globerman et al. |
| 6,290,728 B1 | 9/2001 | Phelps et al. |
| 6,293,964 B1 | 9/2001 | Yadav |
| 6,325,826 B1 | 12/2001 | Vardi et al. |
| 6,331,186 B1 | 12/2001 | Wang et al. |
| 6,344,052 B1 | 2/2002 | Greenan et al. |
| 6,346,089 B1 | 2/2002 | Dibie |
| 6,346,118 B1 | 2/2002 | Baker et al. |
| 6,352,551 B1 | 3/2002 | Wang |
| 6,361,544 B1 | 3/2002 | Wilson et al. |
| 6,383,212 B2 | 5/2002 | Durcan et al. |
| 6,383,213 B2 | 5/2002 | Wilson et al. |
| 6,387,120 B2 | 5/2002 | Wilson et al. |
| 6,391,032 B2 | 5/2002 | Blaeser et al. |
| 6,395,008 B1 | 5/2002 | Ellis et al. |
| 6,402,778 B2 | 6/2002 | Wang |
| 6,409,741 B1 | 6/2002 | Crocker et al. |
| 6,409,750 B1 | 6/2002 | Hyodoh et al. |
| 6,409,755 B1 | 6/2002 | Vrba |
| 6,409,757 B1 | 6/2002 | Trout, III et al. |
| 6,428,567 B2 | 8/2002 | Wilson et al. |
| 6,436,104 B2 | 8/2002 | Hojeibane |
| 6,436,134 B2 | 8/2002 | Richter et al. |
| 6,440,165 B1 | 8/2002 | Richter et al. |
| 6,451,050 B1 | 9/2002 | Rudakov et al. |
| 6,478,814 B2 | 11/2002 | Wang et al. |
| 6,482,211 B1 | 11/2002 | Choi |
| 6,482,227 B1 | 11/2002 | Solovay |
| 6,485,509 B2 | 11/2002 | Killion et al. |
| 6,488,700 B2 | 12/2002 | Klumb et al. |
| 6,508,836 B2 | 1/2003 | Wilson et al. |
| 6,517,558 B2 | 2/2003 | Gittings et al. |
| 6,524,335 B1 | 2/2003 | Hartley et al. |
| 6,540,779 B2 | 4/2003 | Richter et al. |
| 6,547,813 B2 | 4/2003 | Stiger et al. |
| 6,554,856 B1 | 4/2003 | Doorly et al. |
| 6,562,061 B1 | 5/2003 | Wang et al. |
| 6,565,597 B1 | 5/2003 | Fearnot et al. |
| 6,572,649 B2 | 6/2003 | Berry et al. |
| 6,579,312 B2 | 6/2003 | Wilson et al. |
| 6,579,314 B1 | 6/2003 | Lombardi et al. |
| 6,582,394 B1 | 6/2003 | Reiss et al. |
| 6,589,274 B2 | 7/2003 | Stiger et al. |
| 6,596,020 B2 | 7/2003 | Vardi et al. |
| 6,599,316 B2 | 7/2003 | Vardi et al. |
| 6,607,552 B1 | 8/2003 | Hanson |
| 6,626,934 B2 | 9/2003 | Blaeser et al. |
| 6,637,107 B2 | 10/2003 | Yasuhara et al. |
| 6,652,580 B1 | 11/2003 | Chuter et al. |
| 6,656,215 B1 | 12/2003 | Yanez et al. |
| 6,656,216 B1 | 12/2003 | Hossainy et al. |
| 6,663,665 B2 | 12/2003 | Shaolian et al. |
| 6,663,666 B1 | 12/2003 | Quiachon et al. |
| 6,673,104 B2 | 1/2004 | Barry |
| 6,673,106 B2 | 1/2004 | Mitelberg et al. |
| 6,673,107 B1 | 1/2004 | Brandt et al. |
| 6,682,557 B1 | 1/2004 | Quiachon et al. |
| 6,706,062 B2 | 3/2004 | Vardi et al. |
| 6,726,714 B2 | 4/2004 | DiCaprio et al. |

| | | |
|---|---|---|
| 6,740,113 B2 | 5/2004 | Vrba |
| 6,756,094 B1 | 6/2004 | Wang et al. |
| 6,764,504 B2 | 7/2004 | Wang et al. |
| 6,770,092 B2 | 8/2004 | Richter |
| 6,790,224 B2 | 9/2004 | Gerberding |
| 6,805,697 B1 | 10/2004 | Helm et al. |
| 6,805,702 B1 | 10/2004 | Chen et al. |
| 6,824,553 B1 | 11/2004 | Samson et al. |
| 6,830,575 B2 | 12/2004 | Stenzel et al. |
| 6,843,802 B1 | 1/2005 | Villalobos et al. |
| 6,852,116 B2 | 2/2005 | Leonhardt et al. |
| 6,872,215 B2 | 3/2005 | Crocker et al. |
| 6,887,268 B2 | 5/2005 | Butaric et al. |
| 6,911,038 B2 | 6/2005 | Mertens et al. |
| 6,926,690 B2 | 8/2005 | Renati |
| 6,932,837 B2 | 8/2005 | Amplatz et al. |
| 6,986,786 B1 | 1/2006 | Smith |
| 7,481,834 B2 | 1/2009 | Kaplan et al. |
| 7,578,841 B2 | 8/2009 | Yadin et al. |
| 7,717,953 B2 | 5/2010 | Kaplan et al. |
| 7,731,747 B2 | 6/2010 | Kaplan et al. |
| 7,758,630 B2 | 7/2010 | Davis et al. |
| 7,972,369 B2 | 7/2011 | Kaplan et al. |
| 7,972,372 B2 | 7/2011 | Kaplan et al. |
| 8,083,791 B2 | 12/2011 | Kaplan et al. |
| 8,109,987 B2 | 2/2012 | Kaplan et al. |
| 8,187,314 B2 | 5/2012 | Davis et al. |
| 2001/0008976 A1 | 7/2001 | Wang |
| 2001/0011188 A1 | 8/2001 | Berry et al. |
| 2001/0020181 A1 | 9/2001 | Layne |
| 2001/0023356 A1 | 9/2001 | Raz et al. |
| 2001/0037137 A1 | 11/2001 | Vardi et al. |
| 2001/0041930 A1 | 11/2001 | Globerman et al. |
| 2002/0032478 A1* | 3/2002 | Boekstegers et al. ........ 623/1.16 |
| 2002/0058984 A1 | 5/2002 | Butaric et al. |
| 2002/0058993 A1 | 5/2002 | Landau et al. |
| 2002/0077692 A1 | 6/2002 | Besselink |
| 2002/0111619 A1 | 8/2002 | Keast et al. |
| 2002/0116047 A1 | 8/2002 | Vardi et al. |
| 2002/0151959 A1 | 10/2002 | Von Oepen |
| 2002/0156516 A1 | 10/2002 | Vardi et al. |
| 2002/0156525 A1* | 10/2002 | Smith et al. .................. 623/1.22 |
| 2002/0165602 A1 | 11/2002 | Douglas et al. |
| 2002/0169498 A1 | 11/2002 | Kim et al. |
| 2002/0173840 A1 | 11/2002 | Brucker et al. |
| 2002/0183763 A1 | 12/2002 | Callol et al. |
| 2002/0183780 A1 | 12/2002 | Wang |
| 2002/0193862 A1 | 12/2002 | Mitelberg et al. |
| 2002/0193868 A1 | 12/2002 | Mitelberg et al. |
| 2002/0198559 A1 | 12/2002 | Mistry et al. |
| 2003/0083734 A1 | 5/2003 | Friedrich et al. |
| 2003/0097171 A1 | 5/2003 | Elliott |
| 2003/0114912 A1 | 6/2003 | Sequin et al. |
| 2003/0125797 A1 | 7/2003 | Chobotov et al. |
| 2003/0125799 A1 | 7/2003 | Limon |
| 2003/0199967 A1 | 10/2003 | Hartley et al. |
| 2004/0015227 A1 | 1/2004 | Vardi et al. |
| 2004/0024441 A1 | 2/2004 | Bertolino et al. |
| 2004/0054362 A1 | 3/2004 | Lopath et al. |
| 2004/0054396 A1 | 3/2004 | Hartley et al. |
| 2004/0073250 A1 | 4/2004 | Pederson, Jr. et al. |
| 2004/0093058 A1 | 5/2004 | Cottone et al. |
| 2004/0106985 A1 | 6/2004 | Jang |
| 2004/0133261 A1 | 7/2004 | Bigus et al. |
| 2004/0133268 A1 | 7/2004 | Davidson et al. |
| 2004/0138730 A1 | 7/2004 | Mitelberg et al. |
| 2004/0138737 A1 | 7/2004 | Davidson et al. |
| 2004/0143209 A1 | 7/2004 | Liu et al. |
| 2004/0158306 A1 | 8/2004 | Mitelberg et al. |
| 2004/0220655 A1 | 11/2004 | Swanson et al. |
| 2004/0230293 A1 | 11/2004 | Yip et al. |
| 2004/0249434 A1 | 12/2004 | Andreas et al. |
| 2004/0254627 A1 | 12/2004 | Thompson et al. |
| 2004/0260378 A1 | 12/2004 | Goshgarian |
| 2004/0260383 A1 | 12/2004 | Stelter et al. |
| 2005/0010278 A1 | 1/2005 | Vardi et al. |
| 2005/0015108 A1 | 1/2005 | Williams et al. |
| 2005/0049678 A1 | 3/2005 | Cocks et al. |
| 2005/0154447 A1 | 7/2005 | Goshgarian |
| 2005/0159803 A1 | 7/2005 | Lad et al. |
| 2005/0165469 A1 | 7/2005 | Hogendijk et al. |
| 2005/0192656 A1 | 9/2005 | Eidenschink |
| 2005/0203563 A9 | 9/2005 | Pederson, Jr. et al. |
| 2005/0209674 A1 | 9/2005 | Kutscher et al. |
| 2005/0234536 A1 | 10/2005 | Mitelberg et al. |
| 2005/0251195 A1 | 11/2005 | Wang |
| 2005/0261722 A1 | 11/2005 | Crocker et al. |
| 2005/0288769 A1 | 12/2005 | Globerman |
| 2006/0025849 A1 | 2/2006 | Kaplan et al. |
| 2006/0079956 A1 | 4/2006 | Eigler et al. |
| 2006/0116748 A1 | 6/2006 | Kaplan et al. |
| 2006/0178733 A1* | 8/2006 | Pinchuk et al. .............. 623/1.35 |
| 2007/0203571 A1 | 8/2007 | Kaplan et al. |
| 2007/0213803 A1 | 9/2007 | Kaplan et al. |
| 2007/0213804 A1 | 9/2007 | Kaplan et al. |
| 2007/0288082 A1 | 12/2007 | Williams |
| 2008/0015610 A1 | 1/2008 | Kaplan et al. |
| 2008/0015678 A1 | 1/2008 | Kaplan et al. |
| 2008/0183269 A2 | 7/2008 | Kaplan et al. |
| 2008/0294240 A1 | 11/2008 | Casey |
| 2009/0163988 A1 | 6/2009 | Kaplan et al. |
| 2009/0163999 A1 | 6/2009 | Kaplan et al. |
| 2009/0326641 A1 | 12/2009 | Kaplan et al. |
| 2010/0211160 A1 | 8/2010 | Kaplan et al. |
| 2010/0222870 A1 | 9/2010 | Kaplan et al. |
| 2011/0004292 A1 | 1/2011 | Davis et al. |

FOREIGN PATENT DOCUMENTS

| | | |
|---|---|---|
| EP | 0540290 | 1/1998 |
| EP | 0876805 A2 | 11/1998 |
| EP | 0959811 B1 | 1/1999 |
| EP | 1325715 A2 | 9/2003 |
| EP | 1325716 A1 | 9/2003 |
| EP | 1325717 A2 | 9/2003 |
| EP | 1362564 A1 | 11/2003 |
| EP | 1433441 A2 | 6/2004 |
| EP | 1 512 381 A2 | 3/2005 |
| WO | WO 96/38101 | 12/1996 |
| WO | WO 97/17101 A1 | 5/1997 |
| WO | WO 98/19629 A2 | 5/1998 |
| WO | WO 98/24503 | 6/1998 |
| WO | WO 00/15147 A1 | 3/2000 |
| WO | WO 00/69367 | 11/2000 |
| WO | WO 02/47580 A2 | 6/2002 |
| WO | WO 02/49538 A2 | 6/2002 |
| WO | WO 03/020173 A1 | 3/2003 |
| WO | WO 03/039626 A2 | 5/2003 |
| WO | WO 2004/026180 A2 | 4/2004 |
| WO | WO 2004/058100 A2 | 7/2004 |
| WO | WO 2004/089249 A1 | 10/2004 |
| WO | WO 2004/091428 A3 | 10/2004 |
| WO | WO 2004/103217 A1 | 12/2004 |
| WO | WO 2005/041810 A2 | 5/2005 |

OTHER PUBLICATIONS

Endovascular Grafts: History of Minimally Invasive Treatment of Vascular Disease, Timothy A.M. Chuter, *Endoluminal Vascular Prostheses*, pp. 3-17, 1995.

Esophageal Strictures: Treatment with a New Design of Modified Gianturco Stent, Ho. Young Song, M.D. et al., *Radiology*, vol. 184, No. 3, pp. 729-734 Sep. 1992.

Protection of Side-Branches in Coronary Lesions With a New Stent Design, Stephan Baldus, MD et al., *Catherization and Cardiovascular Diagnosis*, vol. 45: No. 4, 456-459, Dec. 1998.

Self-expanding Stainless Steel Biliary Stents, Harold G. Coons, MD, *Radiology*, vol. 170, No. 3, Part 2, pp. 979-983, Mar. 1989.

Serruys, Patrick W et al.; *Handbook of Coronary Stents*; Jan. 15, 2002; pp. 130-131; Martin Dunitz, Ltd.; London, UK.

The Impact of Stent Design on Proximal Stent-graft Fixation in the Abdominal Aorta: an Experimental Study, T. Resch et al., *European Journal of Vascular and Endovascular Surgery*, vol. 20, No. 2, pp. 190-195, Aug. 2000.

The Zenith endoluminal stent-graft system: suprarenal fixation, safety features, modular components, fenestration and custom crafting, Michael M.D. Lawrence-Brown et al., *Vascular and*

*Endovascular Surgical Techniques*, Fourth Edition, pp. 219-223, 2001.

International Search Report and Written Opinion in PCT Application No. PCT/US04/10591 dated Mar. 11, 2005 in 6 pages.

International Search Report in PCT Application No. PCT/US05/36987 dated Jun. 5, 2006.

International Search Report and Written Opinion in PCT Application No. PCT/US07/85429 dated Jun. 2, 2008 in 10 pages.

Supplemental European Search Report for Application No. EP 05 81 2396 mailed Nov. 18, 2009 in 7 pages.

Supplementary European Search Report for Application No. EP 04759166.4 dated Mar. 5, 2007 in 4 pages.

European Patent Office Communication (first substantive examination report) in Application No. 04 759 166.4-1526 dated Apr. 30, 2007 in 3 pages.

International Search Report and Written Opinion in Application No. PCT/US10/40962 dated Oct. 13, 2010, in 14 pages.

Extended European Search Report in Application EP12000249.8 dated May 11, 2012, in 7 pages.

International Search Report and Written Opinion in Application No. PCT/US11/062102 dated Feb. 29, 2012, in 14 pages.

\* cited by examiner

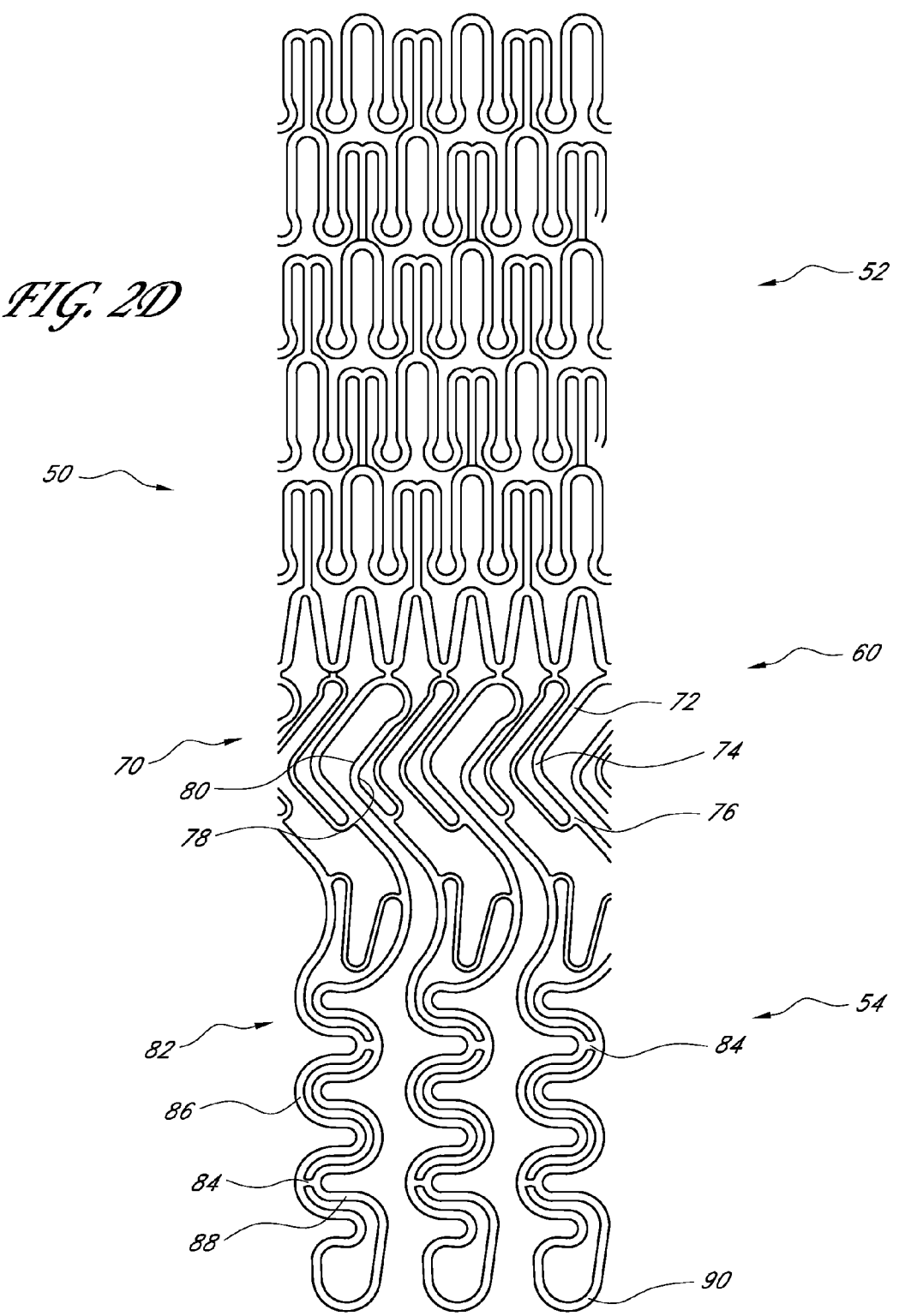

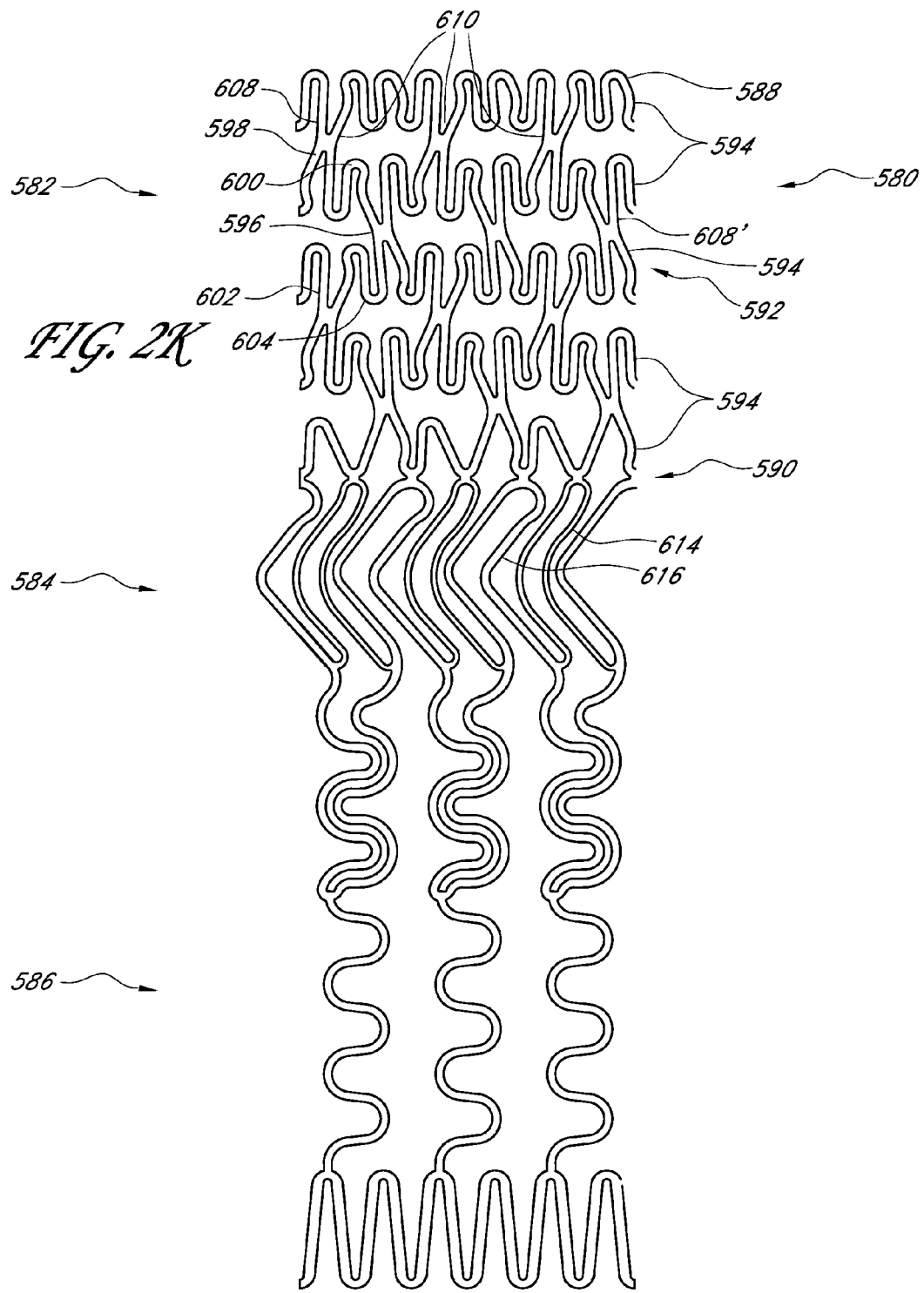

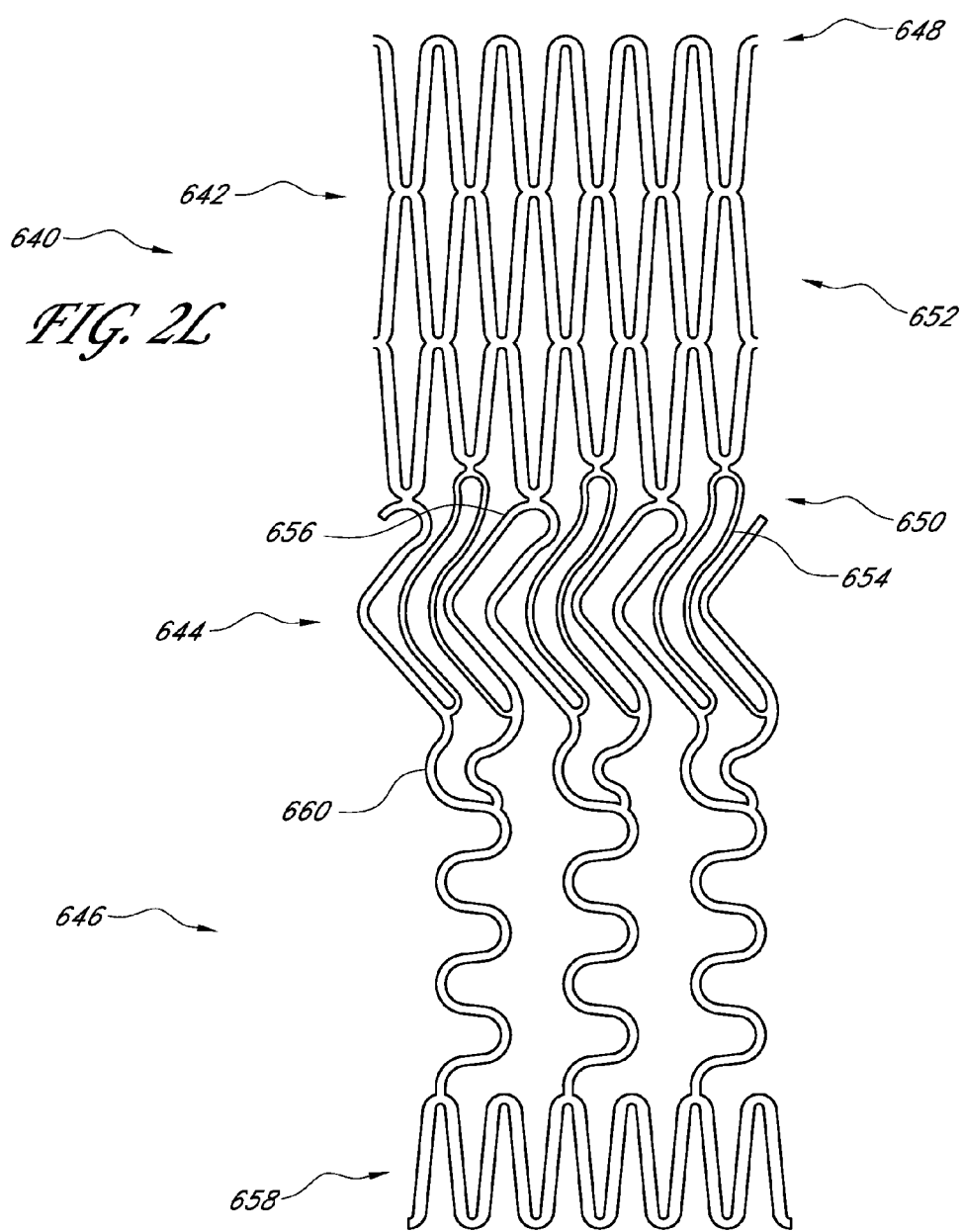

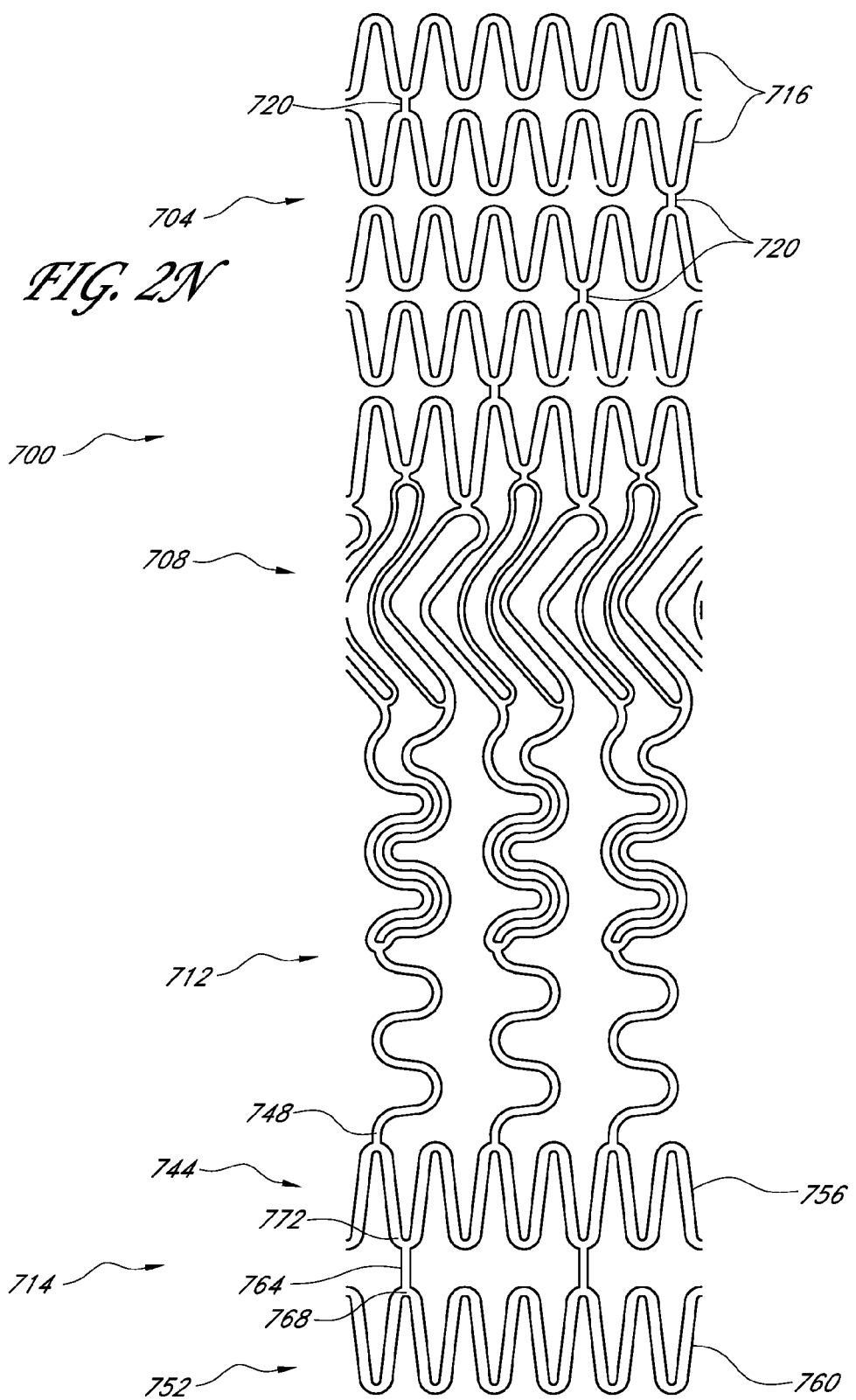

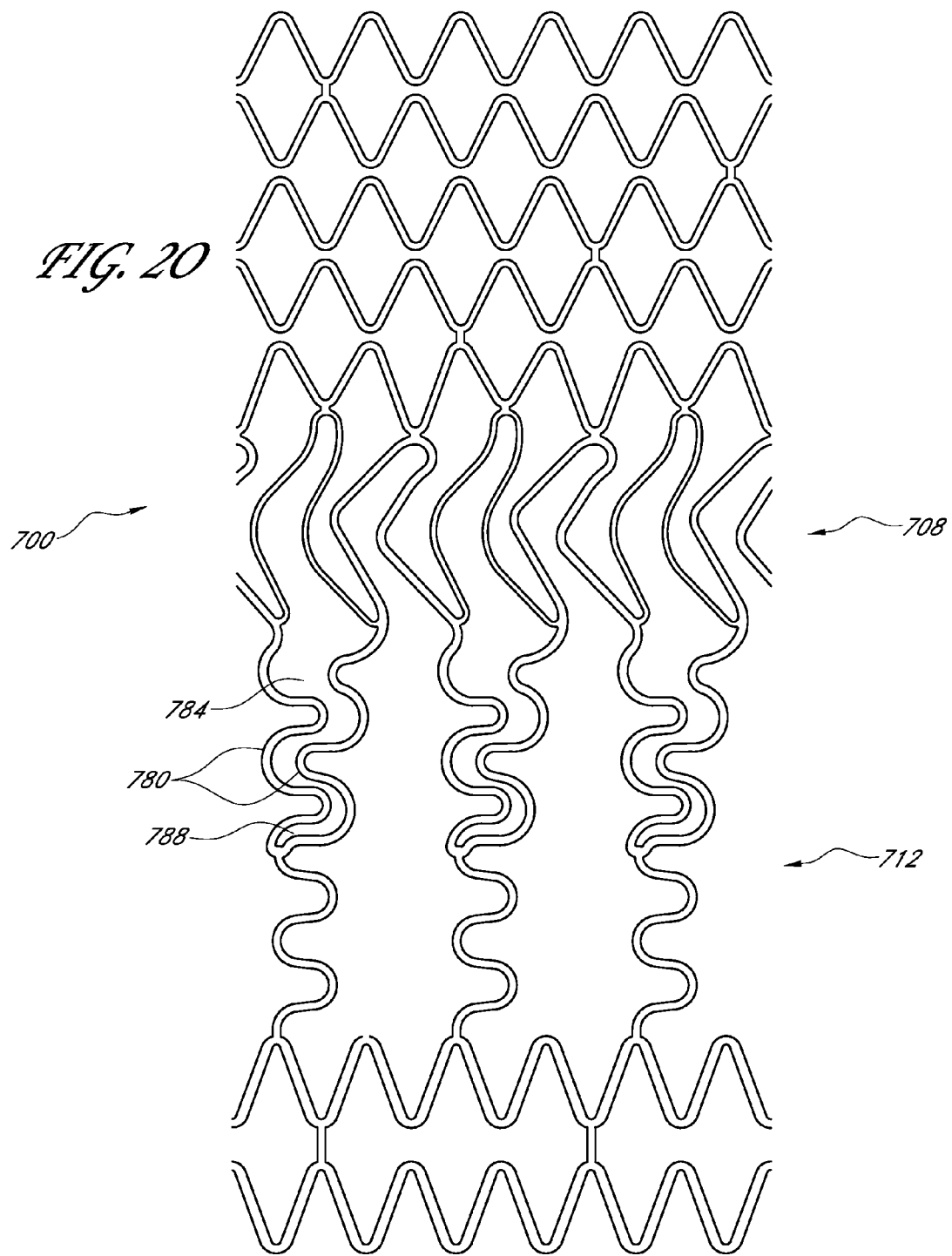

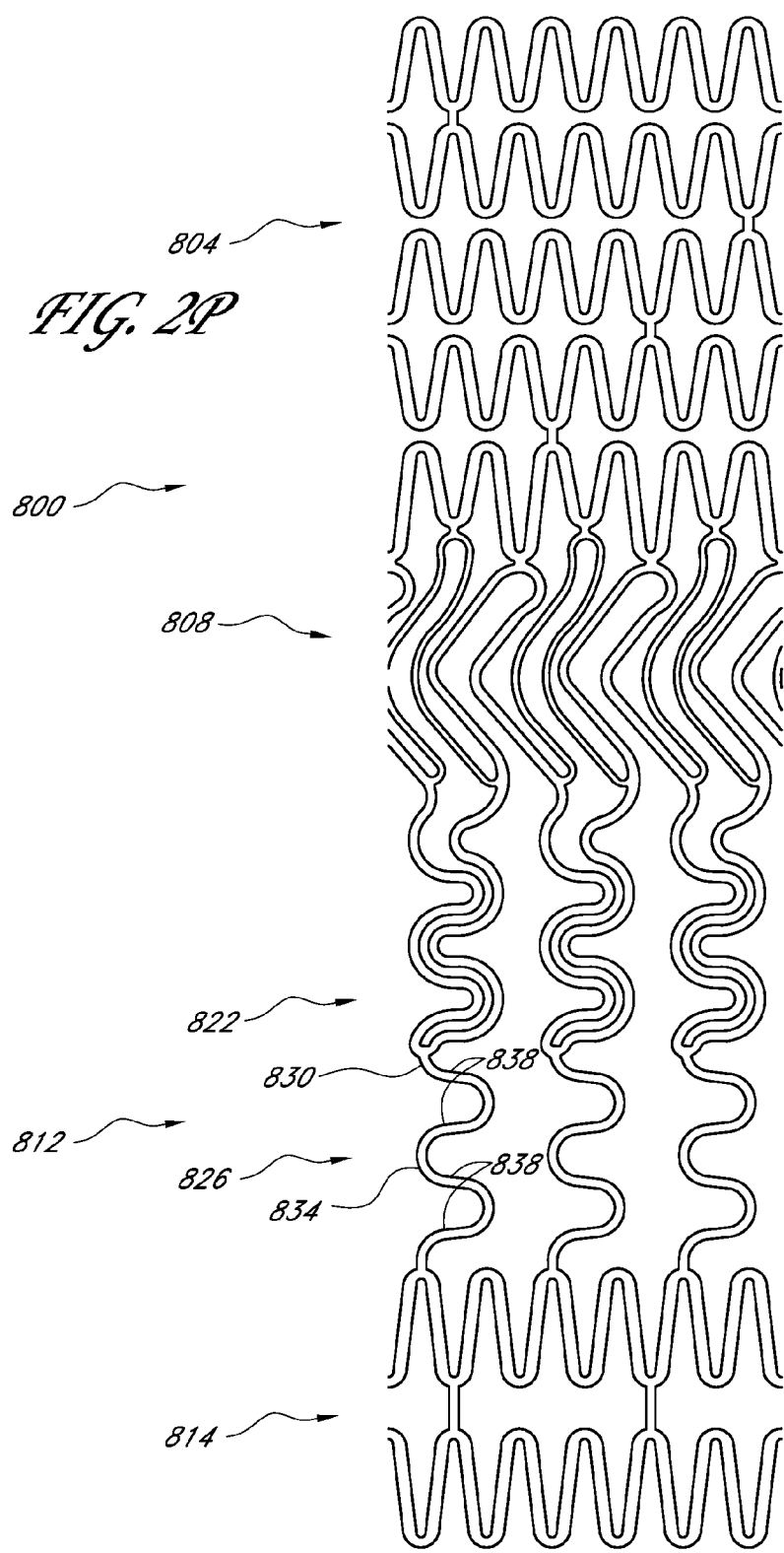

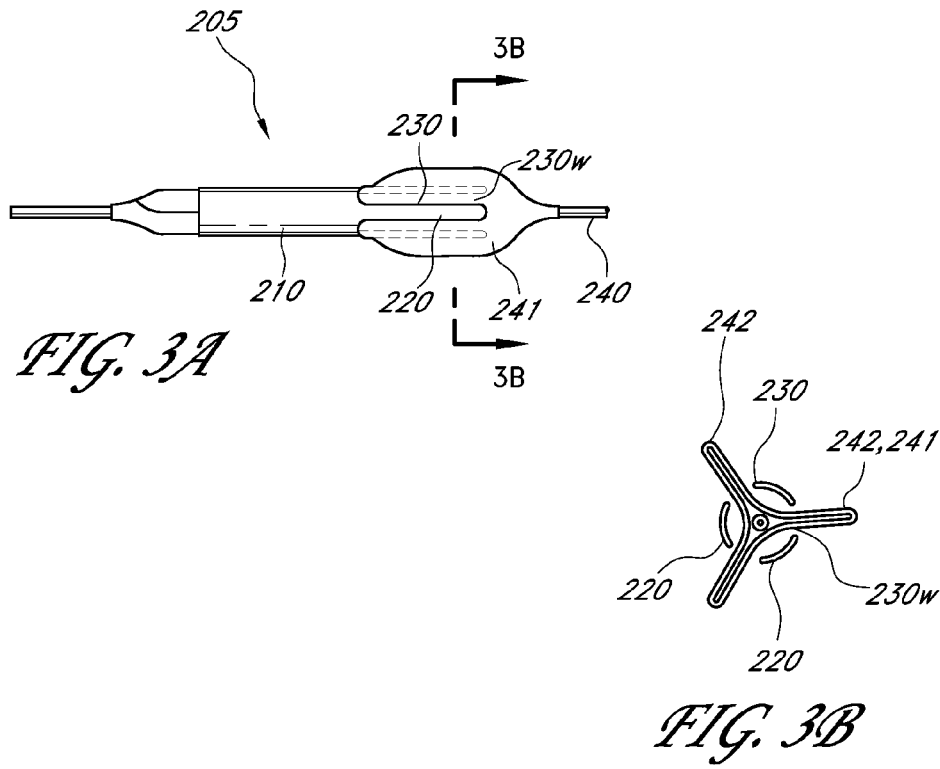
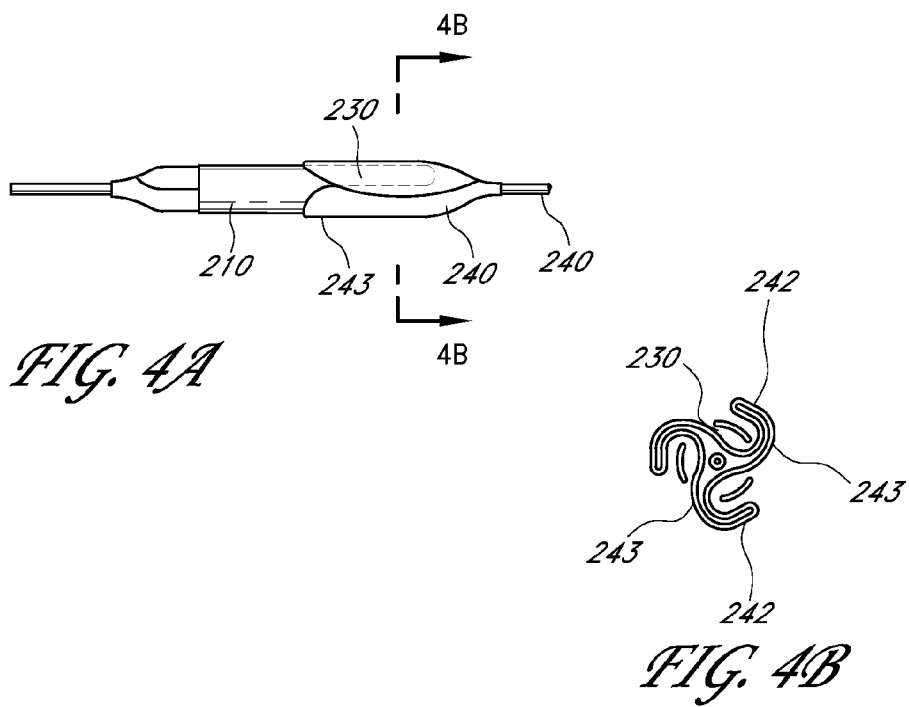

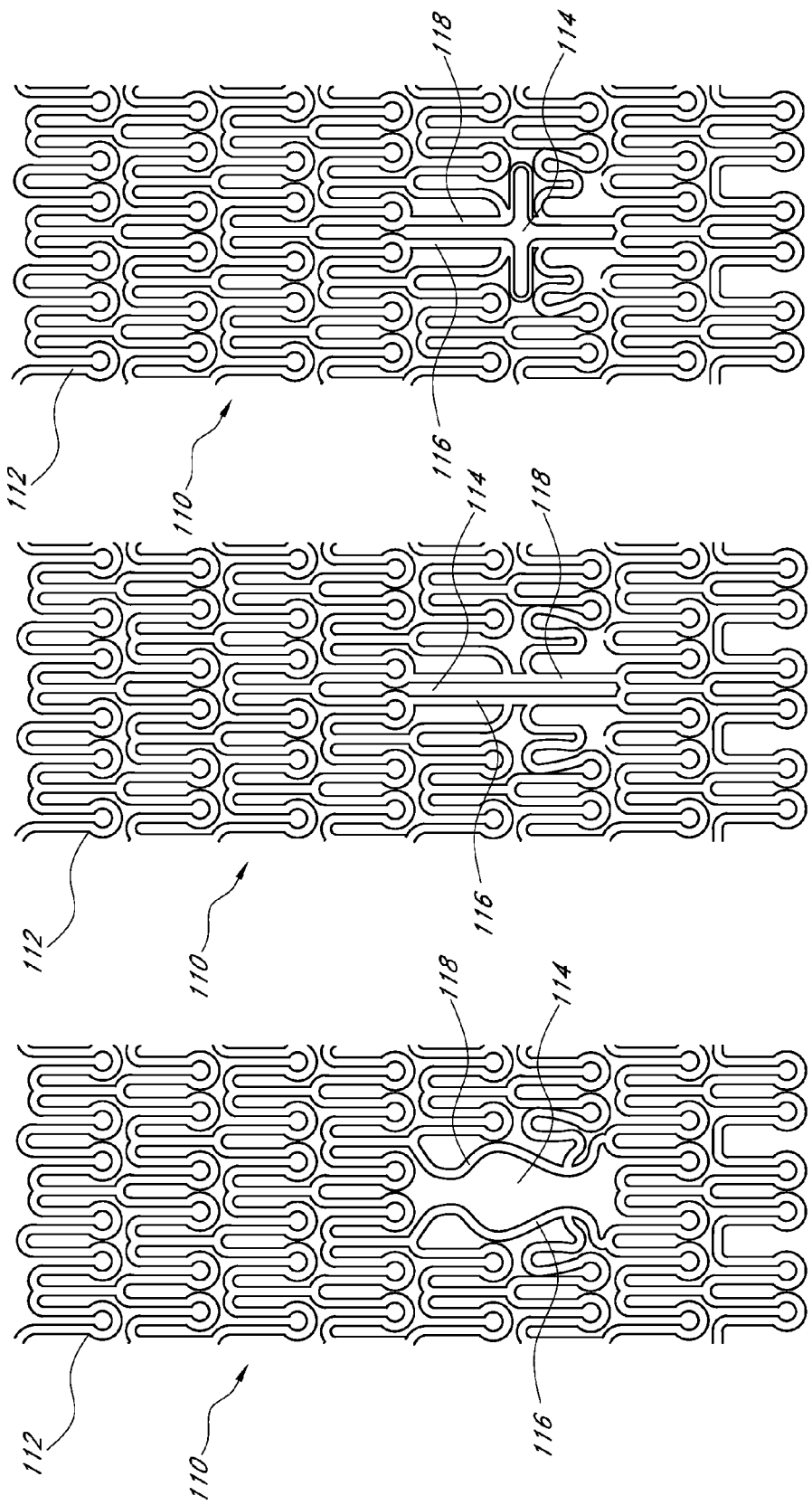

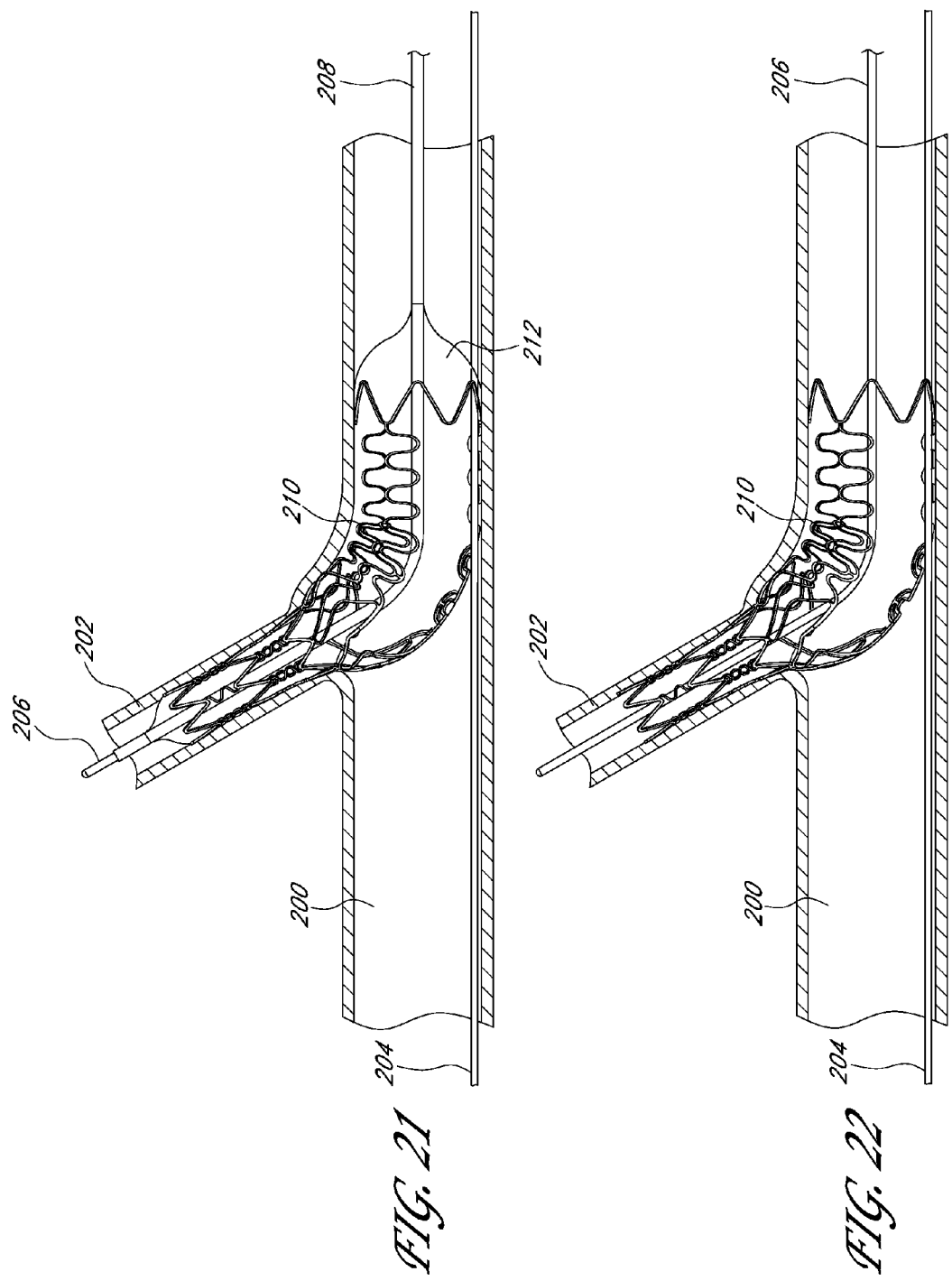

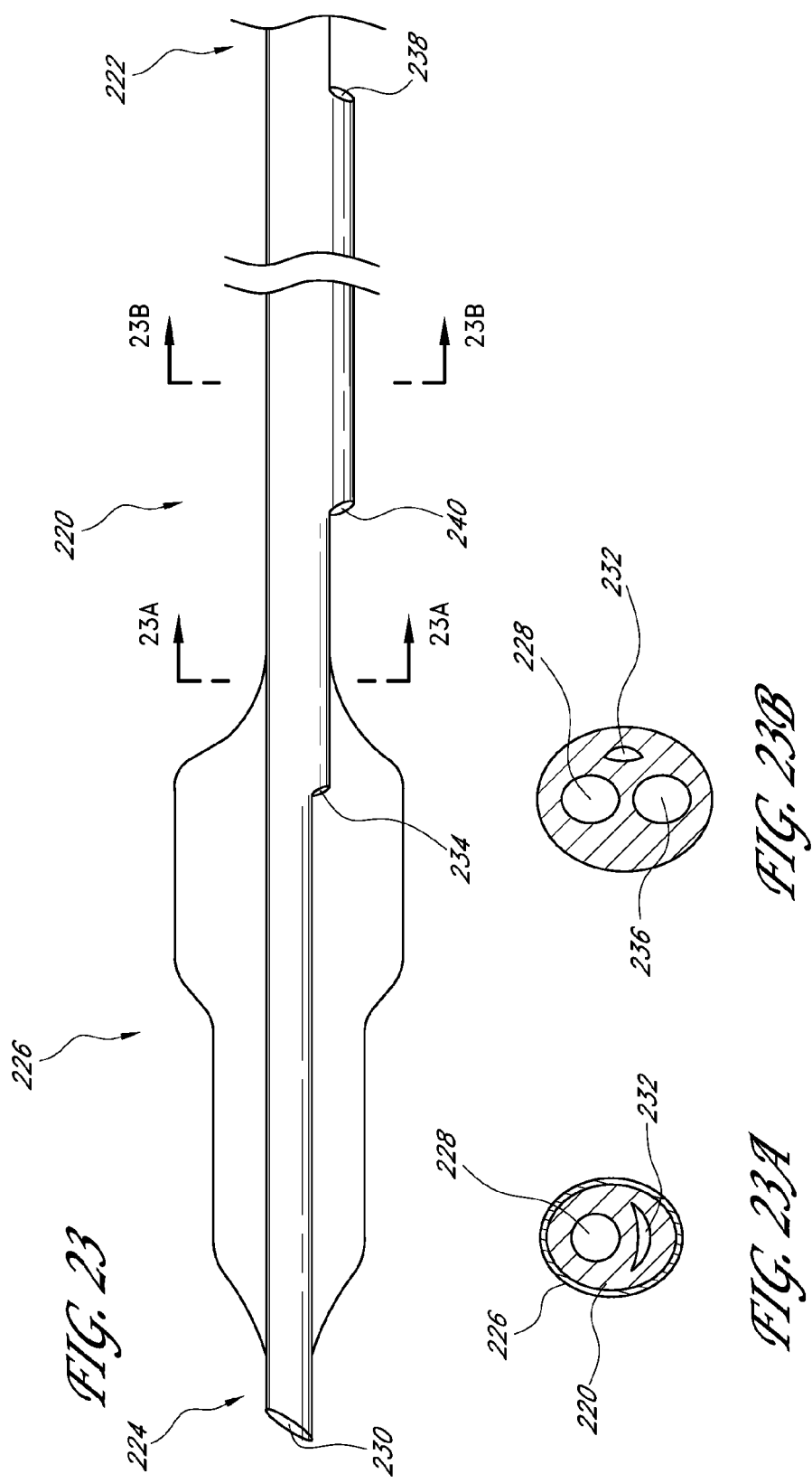

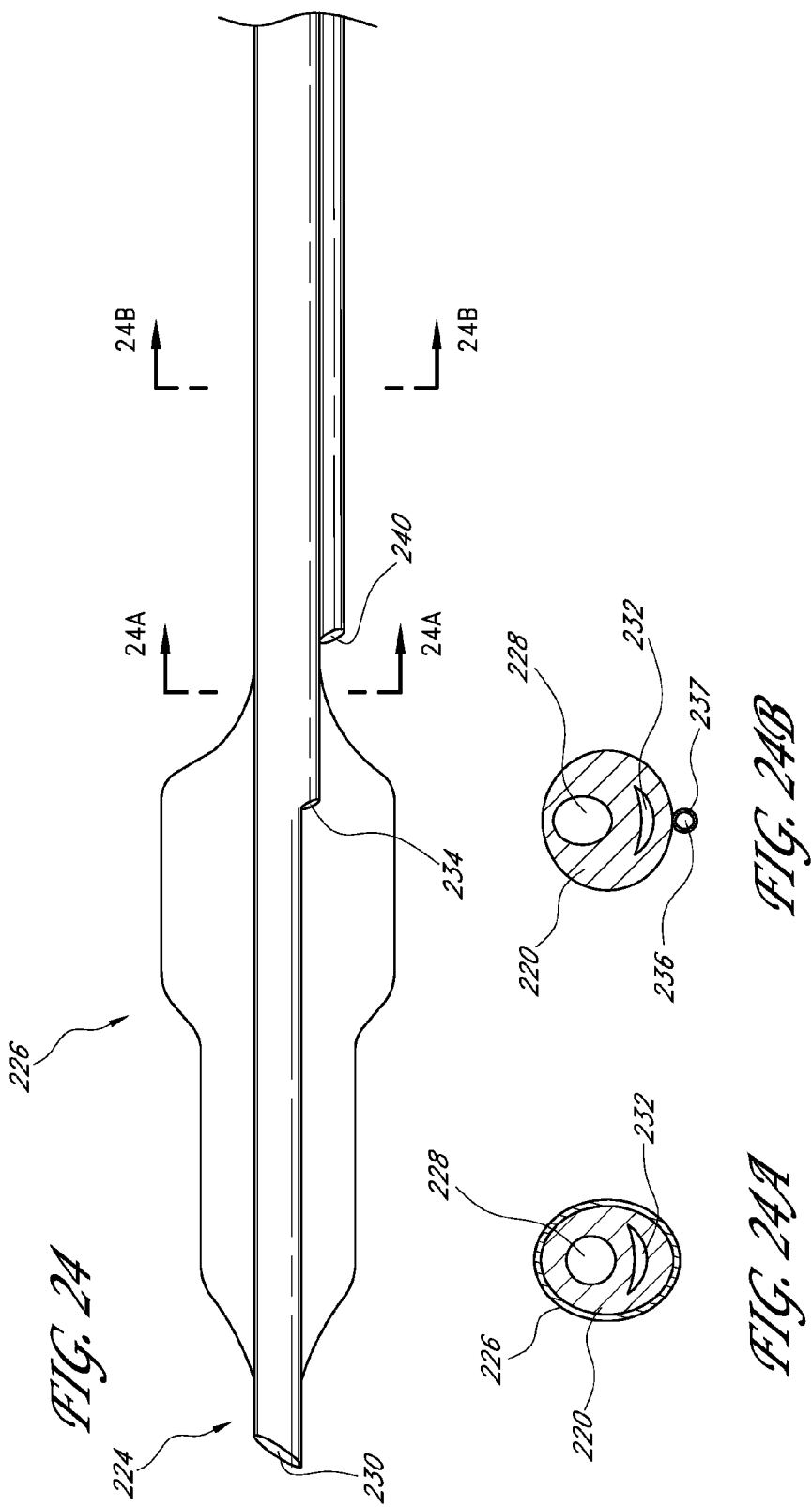

OSTIUM SUPPORT FOR TREATING VASCULAR BIFURCATIONS

CROSS-REFERENCE TO RELATED APPLICATIONS

The present application claims the benefit of priority of U.S. Provisional Patent Application No. 61/222,744, filed Jul. 2, 2009 and the benefit of priority of U.S. Provisional Patent Application No. 61/243,433, filed on Sep. 17, 2009, both of which are incorporated in its entirety by reference herein.

BACKGROUND OF THE INVENTION

1. Field of the Invention

Embodiments of the present invention relate generally to medical devices and methods. More particularly, embodiments of the present invention relate to the structure and deployment of a prosthesis having a stent or other support structure and at least one, and in some implementations at least two fronds for deployment at a branching point in the vasculature or elsewhere.

Maintaining the patency of body lumens is of interest in the treatment of a variety of diseases. Of particular interest to the present invention are the transluminal approaches to the treatment of body lumens. More particularly, the percutaneous treatment of atherosclerotic disease involving the coronary and peripheral arterial systems. Currently, percutaneous coronary interventions (PCI) often involve a combination of balloon dilation of a coronary stenosis (i.e. a narrowing or blockage of the artery) followed by the placement of an endovascular prosthesis commonly referred to as a stent.

A major limitation of PCI/stent procedures is restenosis, i.e., the re-narrowing of a blockage after successful intervention typically occurring in the initial three to six months post treatment. The recent introduction of drug eluting stents (DES) has dramatically reduced the incidence of restenosis in coronary vascular applications and offers promise in peripheral stents, venous grafts, arterial and prosthetic grafts, as well as A-V fistulae. In addition to vascular applications, stents are being employed in treatment of other body lumens including the gastrointestinal systems (esophagus, large and small intestines, biliary system and pancreatic ducts) and the genital-urinary system (ureter, urethra, fallopian tubes, vas deferens).

Treatment of lesions in and around branch points generally referred to as bifurcated vessels, is a developing area for stent applications, particularly, since at least about 5%-10% of all coronary lesions involve bifurcations. However, while quite successful in treating arterial blockages and other conditions, current stent designs are challenged when used at a bifurcation in the blood vessel or other body lumen. Presently, many different strategies are employed to treat bifurcation lesions with currently available stents all of which have major limitations.

One common approach is to place a conventional stent in the main or larger body lumen over the origin of the side branch. After removal of the stent delivery balloon, a second wire is introduced through a cell in the wall of the deployed stent and into the side branch. A balloon is then introduced into the side branch and inflated to enlarge the side-cell of the main vessel stent. This approach can work well when the side branch is relatively free of disease, although it is associated with increased rates of abrupt closure due to plaque shift and dissection as well as increased rates of late restenosis.

Another commonly employed strategy is the 'kissing balloon' technique in which separate balloons are positioned in the main and side branch vessels and simultaneously inflated to deliver separate stents simultaneously. This technique is thought to prevent plaque shift.

Other two-stent approaches including Culotte, T-Stent and Crush Stent techniques have been employed as well. When employing a T-Stent approach, the operator deploys a stent in the side branch followed by placement of a main vessel stent. This approach is limited by anatomic variation (angle between main and side branch) and inaccuracy in stent positioning, which together can cause inadequate stent coverage of the side branch origin commonly referred to as the ostium or Os. More recently, the Crush approach has been introduced in which the side-vessel stent is deployed across the Os with portions in both the main and side branch vessels. The main vessel stent is then delivered across the origin of the side branch and deployed, which results in crushing a portion of the side branch stent between the main vessel stent and the wall of the main vessel. Following main-vessel stent deployment, it is difficult and frequently not possible to re-enter the side branch after crush stenting. Unproven long-term results coupled with concern regarding the inability to re-enter the side branch, malapposition of the stents against the arterial wall and the impact of three layers of stent (which may be drug eluting) opposed against the main vessel wall has limited the adoption of this approach.

These limitations have led to the development of stents specifically designed to treat bifurcated lesions. One approach employs a stent design with a side opening for the branch vessel which is mounted on a specialized balloon delivery system. The specialized balloon delivery system accommodates wires for both the main and side branch vessels. The system is tracked over both wires which provides a means to axially and radially align the stent/stent delivery system. The specialized main vessel stent is then deployed and the stent delivery system removed while maintaining wire position in both the main and side branch vessels. The side branch is then addressed using the kissing balloon technique or by delivering an additional stent to the side branch. Though this approach has many theoretical advantages, it is limited by difficulties in tracking the delivery system over two wires (See, e.g., U.S. Pat. Nos. 6,325,826 and 6,210,429 to Vardi et al.).

Notwithstanding the foregoing efforts, there remains a need for improved devices as well as systems and methods for delivering devices, to treat body lumens at or near the location of an Os between a main body lumen and a side branch lumen, typically in the vasculature, and more particularly in the arterial vasculature. It would be further desirable if such systems and methods could achieve both sufficient radial support as well as adequate surface area coverage in the region of the Os and that the prostheses in the side branches be well-anchored at or near the Os.

2. Description of the Related Art

Stent structures intended for treating bifurcated lesions are described in U.S. Pat. Nos. 6,599,316; 6,596,020; 6,325,826; and 6,210,429. Other stents and prostheses of interest are described in the following U.S. Pat. Nos. 4,994,071; 5,102,417; 5,342,387; 5,507,769; 5,575,817; 5,607,444; 5,609,627; 5,613,980; 5,669,924; 5,669,932; 5,720,735; 5,741,325; 5,749,825; 5,755,734; 5,755,735; 5,824,052; 5,827,320; 5,855,598; 5,860,998; 5,868,777; 5,893,887; 5,897,588; 5,906,640; 5,906,641; 5,967,971; 6,017,363; 6,033,434; 6,033,435; 6,048,361; 6,051,020; 6,056,775; 6,090,133; 6,096,073; 6,099,497; 6,099,560; 6,129,738; 6,165,195; 6,221,080; 6,221,098; 6,254,593; 6,258,116; 6,264,682; 6,346,089; 6,361,544; 6,383,213; 6,387,120; 6,409,750;

6,428,567; 6,436,104; 6,436,134; 6,440,165; 6,482,211; 6,508,836; 6,579,312; and 6,582,394.

SUMMARY OF THE INVENTION

There is provided in accordance with one aspect of the present invention, a prosthesis for placement at an opening from a main body lumen to a branch body lumen. The prosthesis comprises a radially expansible support, the support configured to be deployed in at least a portion of the branch body lumen. A plurality of fronds extends from an end of the support. The fronds are configured to be positioned across the opening and into the main body lumen. A plurality of elongate side wall spaces in between adjacent fronds is provided. The spaces are configured to receive a stent deployment device therethrough. The prosthesis also includes a circumferential link connected to the fronds. The circumferential link is spaced apart from the support by the fronds. The circumferential link comprises a first portion located adjacent to proximal ends of the fronds, and a second portion located on a proximal side of the first portion. The second portion is configured to surround a space that can be occupied by at least a portion of an expansion device.

At least a portion of the prosthesis may be provided with a drug coating, and at least a portion of the fronds and the circumferential link may be provided without a drug coating.

In accordance with another aspect, a prosthesis for placement at an opening from a main body lumen to a branch body lumen is provided. The prosthesis comprises a radially expansible support configured to be deployed in at least a portion of the branch body lumen. The support is adapted to provide a radial force to support a first body lumen. The prosthesis also includes a plurality of fronds and a circumferential link. The fronds extend from an end of the support and are configured to be positioned across the opening and into a second body lumen. The circumferential link is connected to at least one of the fronds. The circumferential link is spaced apart from the support by the at least one frond. The circumferential link comprises a frond engagement portion adjacent to proximal ends of the fronds and a catheter securement portion located on a proximal side of the frond engagement portion.

In accordance with another aspect, a prosthesis for placement at an ostium opening from a first body lumen to a second body lumen is provided. The prosthesis includes a radially expansible support configured to be deployed in at least a portion of the first body lumen. The prosthesis also includes at least one frond and a circumferential link. The at least one frond extends from an end of the support. The at least one frond is configured to be positioned across the ostium opening. The circumferential link is connected to and is spaced apart from the support by the at least one frond. The circumferential link comprises a catheter securement portion and a frond engagement portion. The catheter securement portion and frond engagement portion are located adjacent the end of the at least one frond that is spaced apart from the support. The frond engagement portion located between the catheter securement portion and the support. The catheter securement portion configured to surround a space that can be occupied by at least a portion of an expansion device. The prosthesis is configured to receive a second prosthesis through the space surrounded by the catheter securement portion such that when the second prosthesis is deployed the at least one frond is entrapped between a vessel wall and the second prosthesis.

In accordance with a further aspect of the present invention, there is provided a method for treating a bifurcation between a main lumen and a branch lumen. The method can involve placing any of the prostheses described herein at the bifurcation. The prosthesis is translumenally navigated to a treatment site, and deployed at the site such that the support is in the branch lumen and the circumferential link is in the main lumen.

Further features and advantages of the present invention will become apparent from the detailed description of preferred embodiments which follows, when considered together with the attached drawings and claims.

BRIEF DESCRIPTION OF THE DRAWINGS

FIGS. 2A-2E are lateral views showing embodiments of a stent having fronds in a rolled out configuration. FIG. 2A shows an embodiment having serpentine-shaped fronds, FIG. 2B shows an embodiment having filament shaped fronds, while FIG. 2C shows an embodiment having filament shaped fronds with alternating shortened fronds. FIGS. 2D and 2E illustrate a nested transition zone configuration with two different stent wall patterns.

FIG. 2I is a lateral view as in FIG. 2H, with a modified stent section having enhanced longitudinal flexibility.

FIGS. 2J-2K are lateral views as in FIG. 2H, with a modified stent sections having open cell constructions.

FIG. 2L shows an embodiment with a tapered transition zone and a proximal serpentine section of relatively low stiffness.

FIG. 2N shows another embodiment of a wall pattern for a prosthesis adapted for deployment at a bifurcation.

FIG. 2O shows an expanded configuration of the wall pattern of the prosthesis of FIG. 2N.

FIG. 2P shows another embodiment of a wall pattern of a prosthesis adapted for deployment at a bifurcation.

FIGS. 3A and 3B are lateral and cross sectional views illustrating an embodiment of a stent having fronds and an underlying deployment balloon having a fold configuration such that the balloon folds protrude through the spaces between the fronds.

FIGS. 4A and 4B are lateral and cross sectional views illustrating the embodiment of FIGS. 3A and 3B with the balloon folded over to capture the fronds.

FIG. 5A shows pre-deployment, the balloon uninflated; FIG. 5B shows deployment, with the balloon inflated; and FIG. 5C post-deployment, the balloon now deflated.

FIG. 6A shows the balloon in an unexpanded state; and FIG. 6B shows the balloon in an expanded state, with the cuff expanded radially and shrunken axially.

FIGS. 13A-13C illustrate side wall patterns for three main vessel stents useful in combination with the prosthesis of the present invention.

FIG. 22 is a fourth step in a deployment sequence, in which the stepped balloon has been removed following deployment of the prosthesis across the Os.

FIG. 23 is a side elevational schematic view of a distal portion of a catheter in accordance with the present invention.

FIG. 23A is a cross sectional view taken along the lines 23A-23A in FIG. 23.

FIG. 23B is a cross sectional view taken along the lines 23B-23B in FIG. 23.

FIG. 24 is a side elevational view as in FIG. 23, with a modified catheter in accordance with the present invention.

FIG. 24A is a cross sectional view taken along the line 24A-24A of FIG. 24.

FIG. 24B is a cross sectional view taken along the line 24B-24B in FIG. 24.

DETAILED DESCRIPTION OF THE PREFERRED EMBODIMENT

Figure 1:
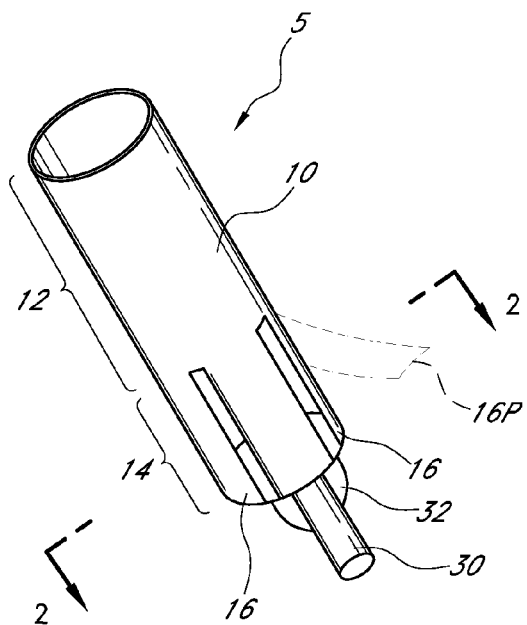
FIG. 1 is a schematic illustration of a prosthesis constructed in accordance with the principles of the present invention.

Embodiments of the present invention provide improved prostheses and delivery systems for their placement within a body lumen, particularly within a bifurcated body lumen and more particularly at an Os opening from a main body lumen to a branch body lumen. The prostheses and delivery systems will be principally useful in the vasculature, most typically the arterial vasculature, including the coronary, carotid and peripheral vasculature; vascular grafts including arterial, venous, and prosthetic grafts such as a bifurcated abdominal aortic aneurysm graft, and A-V fistulae. In addition to vascular applications, embodiments of the present invention can also be configured to be used in the treatment of other body lumens including those in the gastrointestinal systems (e.g., esophagus, large and small intestines, biliary system and pancreatic ducts) and the genital-urinary system (e.g., ureter, urethra, fallopian tubes, vas deferens), and the like.

The prosthesis in accordance with the present invention generally comprises three basic components: a stent or other support, at least one frond extending from the support, and a transition zone between the support and the frond. These components may be integrally formed such as by molding, or by laser or other cutting from tubular stock, or may be separately formed and secured together.

The term "fronds" as used herein will refer to any of a variety of structures including anchors, filaments, petals or other independently multiaxially deflectable elements extending from the stent or other support structure, to engage an adjacent main vessel stent or other associated structure. These fronds can expandably conform to and at least partially circumscribe the wall of the main body vessel to selectively and stably position the prosthesis within the side branch lumen and/or optimize wall coverage in the vicinity of the ostium. Further description of exemplary frond structures and prostheses is found in co-pending application Ser. No. 10/807,643, the full disclosure of which has previously been incorporated herein by reference. Various embodiments of the present invention provide means for capturing or otherwise radially constraining the fronds during advancement of the prosthesis through the vasculature (or other body lumen) to a target site and then releasing the fronds at the desired deployment site.

The prostheses of the present invention are particularly advantageous since they permit substantially complete coverage of the wall of the branch body lumen up to and including the lumen ostium or Os. Additionally, the prostheses have integrated fronds which expandably conform to and at least partially circumscribe the wall of the main body vessel to selectively and stably link the prosthesis to the main vessel stent. The fronds may be fully expanded to open the luminal passage through the main branch lumen. Such complete opening is an advantage since it provides patency through the main branch lumen. Moreover, the open main vessel lumen permits optional placement of a second prosthesis within the main branch lumen using conventional techniques.

In a first aspect of the present invention, a prosthesis comprises a radially expansible support and at least one or often two or more fronds extending axially from an end of the support. The fronds are adapted to extend around, or "expandably circumscribe" a portion of, usually at least one-half of the circumference of the main vessel wall at or near the Os when the support is implanted in the branch lumen with the fronds extending into the main lumen. By "expandably circumscribe," it is meant that the fronds will extend into the main body lumen after initial placement of the support within the branch body lumen. The fronds will be adapted to then be partially or fully radially expanded, typically by expansion of a balloon or other expandable structure therein, so that the fronds deform outwardly and conform to the interior surface of the main lumen.

The fronds will usually extend axially within the main vessel lumen for some distance after complete deployment. In certain embodiments, the contact between the fronds and the main vessel wall will usually extend both circumferentially (typically at least one frond may cover an arc equal to one-half or more of the circumference of the main vessel) and axially.

Deformation of the fronds to conform to at least a portion of the wall of the main body lumen provides a generally continuous coverage of the Os from the side branch lumen to the main vessel lumen. Further and/or complete expansion of the fronds within the main body lumen may press the fronds firmly against the main body lumen wall and open up the fronds so that they do not obstruct flow through the main body lumen, while maintaining patency and coverage of the side branch and os.

Usually, the prosthesis will include at least two or three fronds extending axially from the end of the support. The prosthesis could include four, five, or even a greater number of fronds, but the use of three such fronds is presently contemplated for a coronary artery embodiment. The fronds will have an initial length (i.e., prior to radial expansion of the prosthesis) which is at least about 1.5 times the width of the prosthesis prior to expansion, typically at least about 2 times the width, more typically at least about 5 times the width, and often about 7 times the width or greater. The lengths will typically be at least about 2 mm, preferably at least about 3 mm, and more preferably at least about 6 mm. The frond length may also be considered relative to the diameter of the corresponding main vessel. For example, a prosthesis configured for use in a branch vessel from a main vessel having a 3 mm lumen will preferably have a frond length of at least about 7 mm and in some embodiments at least about 9 mm.

Embodiments of the present invention incorporating only a single frond are also contemplated. The single frond may extend axially from the branch vessel support as has been described in connection with multi frond embodiments. Alternatively, the single frond (or two or three or more fronds) may extend in a helical or spiral pattern, such that it wraps in a helical winding about the longitudinal axis extending through the branch vessel support.

The fronds may have a fixed width or a width which is expandable to accommodate the expansion of the support, and the fronds may be "hinged" at their point of connection to the support to permit freedom to adapt to the geometry of the main vessel lumen as the prosthesis is expanded. As used herein, "hinged" does not refer to a specific structure such as a conventional hinge, but rather to any combination of structures, materials and dimensions that permit multiaxial flexibility of the frond relative to the support so that the frond can bend in any direction and/or rotate about any axis to conform to the ablumenal surface of the expanded main vessel stent under normal use conditions. It is also possible that the fronds could be attached at a single point to the support, thus reducing the need for such expandability. The fronds may be congruent, i.e., have identical geometries and dimensions, or may have different geometries and/or dimensions. In particular, in some instances, it may be desirable to provide fronds having different lengths and/or different widths.

In another aspect of the invention, at least one of the of fronds has a loop or filament shape and includes a first expandable strut configured to be positioned at the Os in an expanded state and provide radial support to an interior portion of the main body lumen. The fronds can be fabricated from flexible metal wire, molded, laser cut or otherwise formed from tube stock in accordance with known techniques. The strut can be configured to be substantially triangular in the expanded state. Also, at least one of the fronds may be configured to be expandably deployed proximate a vessel wall by an expandable device such as an expandable balloon catheter.

In another aspect of the invention, a prosthesis delivery system comprises a delivery catheter having an expandable member and a prosthesis carried over the expandable member. The prosthesis has a radially expandable support such as a tubular stent and at least two fronds extending axially from the support. The system also includes a retainer for capturing the fronds to prevent them from divaricating from the expandable member as the catheter is advanced through a patient's vasculature. "Divarication" as used herein means the separation or branching of the fronds away from the delivery catheter. Various embodiments of the capture means prevent divarication by constraining and/or imparting sufficient hoop strength to the fronds to prevent them from branching from the expandable member during catheter advancement in the vasculature.

In one embodiment, the capturing means comprises a portion of the expandable member that is folded over the fronds where the folds protrude through axial gaps between adjacent fronds. In another embodiment, the capturing means comprises a cuff that extends over at least a portion of the fronds to hold them during catheter advancement. The cuff can be positioned at the proximal end of the prosthesis and can be removed by expansion of the expandable member to either plastically or elastically deform the cuff, break the cuff, or reduce the cuff in length axially as the cuff expands circumferentially. The cuff is then withdrawn from the target vessel. In yet another embodiment, the capturing means can comprise a tether which ties together the fronds. The tether can be configured to be detached from the fronds prior to expansion of the expandable member. In alternative embodiments, the tether can be configured to break or release upon expansion of the expandable member so as to release the fronds.

In an exemplary deployment protocol using the prosthesis delivery system, the delivery catheter is advanced to position the prosthesis at a target location in a body lumen. During advancement, at least a portion of the fronds are radially constrained to prevent divarication of the fronds from the delivery catheter. When the target location is reached, the radial constraint is released and the prosthesis is deployed within the lumen.

In various embodiments, the release of the fronds and expansion of the prosthesis can occur simultaneously or alternatively, the radial constraint can be released prior to, during, or after expanding/deploying the prosthesis. In embodiments where the radial constraint comprises balloon folds covering the fronds or a cuff or tether, the constraint can be released as the balloon is inflated. In alternative embodiments using a cuff or tether, the cuff/tether can be withdrawn from the fronds prior to expansion of the support.

Embodiments of the above protocol can be used to deploy the prosthesis across the Os of a branch body lumen and trailing into the main body lumen. In such applications, the prosthesis can be positioned so that the stent lies within the branch body and at least two fronds extend into the main body lumen. The fronds are then circumferentially deformed to conform to at least a portion of the main vessel wall to define a main vessel passage through the fronds. At least two and preferably at least three fronds extend into the main body lumen.

Radiopaque or other medical imaging visible markers can be placed on the prostheses and/or delivery balloon at desired locations. In particular, it may be desirable to provide radiopaque markers at or near the location on the prosthesis where the stent is joined to the fronds. Such markers will allow a transition region of the prosthesis between the stent and the fronds to be properly located near the Os prior to stent expansion. The radiopaque or other markers for locating the transition region on the prosthesis can also be positioned at a corresponding location on a balloon catheter or other delivery catheter. Accordingly, in one embodiment of the deployment protocol, positioning the prosthesis can include aligning a visible marker on at least one of the prosthesis, on the radial constraint, and the delivery balloon with the Os.

In various embodiments for deploying the prosthesis, the support is expanded with a balloon catheter expanded within the support. In some instances, the support and the fronds may be expanded and deformed using the same balloon, e.g., the balloon is first used to expand the support, partially withdrawn, and then advanced transversely through the fronds where it is expanded for a second time to deform the fronds. A balloon the length of the support (shorter than the total prosthesis length) can be used to expand the support, and then be proximally retracted and expanded in the fronds. Alternatively, separate balloon catheters may be employed for expanding the support within the side branch and for deforming the fronds against the wall of the main body lumen.

The fronds may expand radially in parallel with the support section of the prosthesis. Then, in a second step, the fronds may be folded out of plane as the main vessel stent or balloon is deployed. Deformation of the fronds at least partially within the main body lumen provides a generally continuous coverage of the Os from the side body lumen to the main body lumen. Further and/or complete expansion of the fronds within the main body lumen may press the fronds firmly against the main body lumen wall and open up the fronds so that they do not obstruct flow through the main body lumen.

The prosthesis may include at least one and in some embodiments at least three fronds extending axially from the end of the support. The fronds will have an initial length (i.e., prior to radial expansion of the stent) which is at least about 1.5 times the cross sectional width of the support prior to expansion, typically at least about 2 times the width, more typically at least about 5 times the width, and often about 7 times the width or greater. The lengths of the fronds will typically be at least about 2 mm, preferably at least about 3 mm, and more preferably at least about 6 mm, as discussed elsewhere herein additional detail. The fronds will usually have a width which is expandable to accommodate the expansion of the stent, and the fronds may be "hinged" or otherwise flexibly connected at their point of connection to the prosthesis to permit freedom to adapt to the geometry of the main vessel lumen as the stent is expanded. It is also possible that the fronds could be attached to the single point to the prosthesis, thus reducing the need for such expandability. Fronds may be optimized for particular bifurcation angles and orientations, such as by making the fronds for positioning closer to the "toe" of the bifurcation longer than the fronds for positioning closer to the carina or "heel" of the bifurcation.

The fronds are configured such that during deployment and main vessel stent passage and placement, the fronds allow for longitudinal elongation or compression. In particular, the fronds may elongate axially during main vessel stent deployment, in order to fully accommodate the main vessel stent as will be apparent from the disclosure herein. The longitudinal adjustability of the fronds enables the implant to axially elongate or contract by at least about 5%, and often at least about 10% of the total length of the implant, based upon its predeployed length. In some cases, the longitudinal adjustability of the fronds enables the implant to axially elongate or contract by at least about 20% to about 30% of the total length of the implant, based upon its predeployed length. In some cases, the longitudinal adjustability of the fronds enables the implant to axially elongate or contract by at least about 30% to about 50% or more of the total length of the implant, based upon its predeployed length. Thus, in an implant having an overall length of about 19 mm prior to deployment, the axial length of the implant as measured along the outside surface of the longest frond post-deployment may achieve an elongation of at least about 1.9 mm under normal deployment conditions.

Figure 2:
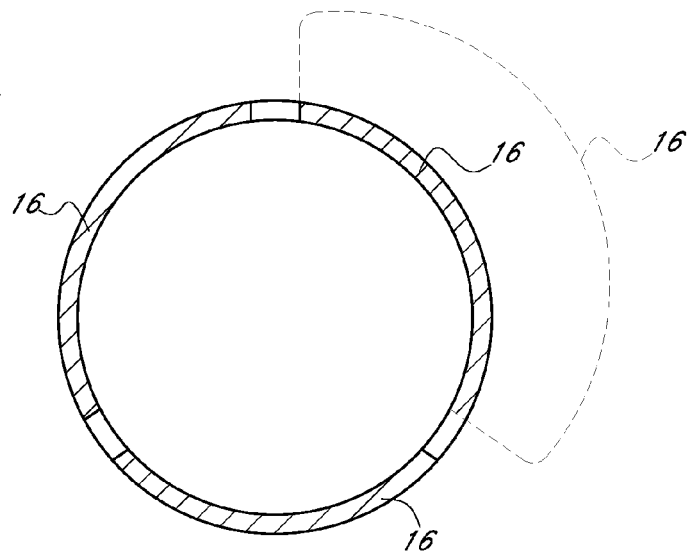
FIG. 2 is a cross-sectional view taken along line 2-2 of FIG. 1.

Referring now to FIGS. 1 and 2, an embodiment of a prosthesis and delivery system 5 of the present invention for the delivery of a prosthesis to a bifurcated vessel can include a prosthesis 10 and a delivery catheter 30. Prosthesis 10 can include at least a radially expansible support section 12 and a frond section 14 with one or more fronds 16. The base of the fronds resides in a transition zone, described below. In various embodiments, the frond section 14 includes at least two axially extending fronds 16, with three being illustrated.

Balloon catheters suitable for use with the prosthesis of the present invention are well understood in the art, and will not be described in great detail herein. In general, a catheter suitable for use for deployment of the prosthesis of the present invention will comprise an elongate tubular body extending between a proximal end and a distal end. The length of the (catheter) tubular body depends upon the desired application. For example, lengths in the area of from about 120 cm to about 140 cm are typical for use in a percutaneous transluminal coronary application intended for accessing the coronary arteries via the femoral artery. Other anatomic spaces including renal, iliac, femoral and other peripheral applications may call for a different catheter shaft length and balloon dimensions, depending upon the vascular access site as will be apparent to those of skill in the art.

The catheter shaft is provided with at least one central lumen, for an inflation media for inflating an inflatable balloon carried by the distal end of the catheter shaft. In an over the wire embodiment, the catheter shaft is additionally provided with a guidewire lumen extending throughout the entire length thereof. Alternatively, the prosthesis of the present invention may be deployed from a rapid exchange or monorail system, in which a proximal access port for the guidewire lumen is provided along the side wall of the catheter shaft distally of the proximal manifold, such as within about the distal most 20 cm of the length of the balloon catheter, or from a convertible system as is known in the art.

The catheter shaft for most applications will be provided with an approximately circular cross sectional configuration, having an external diameter within the range of from about 0.025 inches to about 0.065 inches depending upon, among other things, whether the target bifurcation is in the coronary or peripheral vasculature. Systems may have diameters in excess of about 0.25 inches and up to as much as about 0.35 inches in certain applications. Diameters of from about 1.5 mm up to as large as about 7 mm are contemplated for coronary indications. Additional features and characteristics may be included in the deployment catheter design, such frond retention structures discussed below, depending upon the desired functionality and clinical performance as will be apparent to those of skill in the art.

The radially expansible support section 12 will typically be expandable by an expansion device such as a balloon catheter, but alternatively it can be self expandable. The support section 12 may be formed using any of a variety of conventional patterns and fabrication techniques as are well-described in the prior art.

Depending upon the desired clinical result, the support section or stent 12 may be provided with sufficient radial force to maintain patency of a diseased portion of the branch lumen. This may be desirable in an instance were vascular disease is present in the branch vessel. Alternatively, the support section 12 may be simply called upon to retain the fronds in position during deployment of the primary vascular implant. In this instance, a greater degree of flexibility is afforded for the configuration of the wall pattern of the support section 12. For example, support section 12 may comprise a helical spiral, such as a Nitinol or other memory metal which is deployable from an elongate deployment lumen, but which reverts to its helical configuration within the branch vessel. Alternative self expandable structures may be used such as a zig-zag series of struts, connected by a plurality of proximal apexes and a plurality of distal apexes and rolled into a cylindrical configuration. This configuration is well understood in the vascular graft and stent arts, as a common foundation for a self expandable tubular support.

In one implementation of the present invention, the prosthesis comprises an overall length of about 19 mm, which is made up of a stent having a length of about 9.6 mm, a targeted expanded diameter of about 2.5 mm and a plurality of fronds having a length of about 9.3 mm.

The fronds will usually have a width measured in a circumferential direction in the transition zone which is expandable from a first, delivery width to a second, implanted width to accommodate the expansion of the support, while maintaining optimal wall coverage by the fronds. Thus, although each of the fronds may comprise a single axially extending ribbon or strut, fronds are preferably configured to permit expansion in a circumferential direction at least in the transition zone with radial expansion of the support structure. For this purpose, each frond may comprise a single axially extending element, but often comprises at least two axially extending elements 66A and 66D, and optimally three or more axially extending elements, which can be spaced laterally apart from each other upon radial expansion of the prosthesis, to increase in width in the circumferential direction. The increased width referred to herein will differ on a given frond depending upon where along the length of the frond the measurement is taken. Fronds of the type illustrated herein will increase in width the most at the end attached to the support, and the least (or none) at the free apex end as will be appreciated by those of skill in the art. Circumferentially expanding at least the base of the frond enables optimal wall coverage in the vicinity of the ostium, following deployment of the prosthesis at the treatment site. In addition, multiple elements results in a greater surface area as a biological substrate or increased delivery of pharma agents.

In the illustrated embodiments, each of the fronds 16 has an equal width with the other fronds 16. However, a first frond or set of fronds may be provided with a first width (measured in a circumferential direction) and a second frond or set of fronds may be provided with a second, different width. Dissimilar width fronds may be provided, such as alternating fronds having a first width with fronds having a second width.

In each of the foregoing constructions, radially symmetry may exist such that the rotational orientation of the prosthesis upon deployment is unimportant. This can simplify the deployment procedure for the prosthesis. Alternatively, prostheses of the present invention exhibiting radial asymmetry may be provided, depending upon the desired clinical performance. For example, a first frond or set of fronds may be centered around 0° while a second frond or set of fronds is centered around 180° when the prosthesis is viewed in a proximal end elevational view. This may be useful if the fronds are intended to extend around first and second opposing sides of the main vessel stent. Asymmetry in the length of the fronds may also be accomplished, such as by providing fronds at a 0° location with a first length, and fronds at 180° location with a second length. As will become apparent below, such as by reference to FIG. 9A, certain fronds in the deployed prosthesis will extend along an arc which aligns with the axis of the branch vessel at a distal end, and aligns with the axis of the main vessel at a proximal end. The proximal ends of fronds of equal length will be positioned axially apart along the main vessel lumen. If it is desired that the proximal ends of any of the fronds align within the same transverse cross section through the main vessel lumen, or achieve another desired configuration, fronds of different axial lengths will be required as will become apparent to those of skill in the art.

Certain additional features may be desirable in the prosthesis and/or deployment system of the present invention, in an embodiment in which the rotational orientation of the prosthesis is important. For example, the catheter shaft of the deployment system preferably exhibits sufficient torque transmission that rotation of the proximal end of the catheter by the clinician produces an approximately equal rotation at the distal end of the catheter. The torque transmission characteristics of the catheter shaft may be optimized using any of a variety of structures which are known in the art. For example, a helical winding may be incorporated into the wall of the catheter shaft, using any of a variety of embedding techniques, or by winding a filament around an inner tube and positioning an outer tube over the winding, subsequently heat shrinking or otherwise fusing the tubes together. Bi-directional torque transmission characteristics can be optimized by providing a first winding in a first (e.g. clockwise) direction, and also a second winding in a second (e.g. counter clockwise) direction. The winding may comprise any of a variety of materials, such as metal ribbon, or a polymeric ribbon. Various tubular meshes and braids may also be incorporated into the catheter wall.

In addition, the rotational orientation of the prosthesis is preferably observable fluoroscopically, or using other medical imaging techniques. For this purpose, one or more markers is preferably provided on either the prosthesis, the restraint or the deployment catheter, to enable visualization of the rotational orientation.

The sum of the widths measured in the circumferential direction of the fronds 16 when the prosthesis is in either the first, transluminal navigation configuration or the second, deployed configuration will preferably add up to no more than one circumference of the stent portion of the prosthesis. In this manner, the width of the frond 16s at the level of attachment may be maximized, but without requiring overlap especially in the first configuration. The width of each frond 16 may generally increase upon deployment of the prosthesis to at least about 125%, often at least about 200%, and in some instances up to about 300% or more of its initial width, at least at the distal end (base) of the frond 16. The proximal free end of each frond 16 may not increase in circumferential width at all, with a resulting gradation of increase in circumferential width throughout the axial length from the proximal end to the distal end of the frond. While portions of the fronds may expand as described above, in alternate constructions, the fronds may have a width that remains constant or substantially constant throughout the length of the frond as the prosthesis is deployed.

The fronds may be "hinged" as has been described at their point of connection to the support to permit freedom to adapt to the geometry of the main vessel lumen as the prosthesis is expanded. It is also possible that each frond is attached at a single point to the support, thus reducing the need for such expandability at the junction between the frond and the support. The fronds may be congruent, i.e., have identical geometries and dimensions, or may have different geometries and/or dimensions. Again, further description of the fronds may be found in co-pending application Ser. No. 10/807,643.

Fronds 16, will usually extend axially from the support section 12, as illustrated, but in some circumstances the fronds can be configured to extend helically, spirally, in a serpentine pattern, or other configurations as long as the configuration permits placement of the stent in a vessel such that the fronds extend across the Os. It is desirable, however, that the individual fronds be radially separable so that they can be independently, displaced, folded, bent, rotated about their longitudinal axes, and otherwise positioned within the main body lumen after the support section 12 has been expanded within the branch body lumen. In the schematic embodiment of FIG. 1, the fronds 16 may be independently folded out in a "petal-like" configuration, forming petals 16p, as generally shown in broken line for one of the fronds in FIGS. 1 and 2.

Figure 1A:
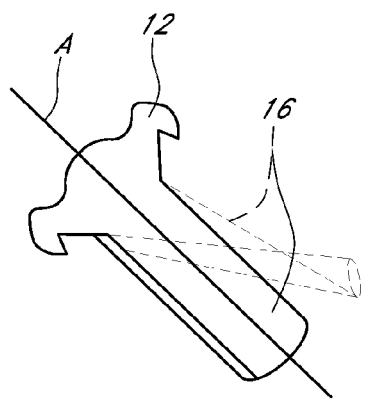
FIG. 1A is a detailed view of the fronds of the prosthesis of FIG. 1, shown with the fronds deployed in broken line.

In preferred embodiments, fronds 16 will be attached to the support section 12 such that they can both bend and rotate relative to an axis A thereof, as shown in broken line in FIG. 1A. Bending can occur radially outwardly and rotation or twisting can occur about the axis A or a parallel to the axis A as the fronds are bent outwardly. Such freedom of motion can be provided by single point attachment joints as well as two point attachments or three or more point attachments.

Figure 2A:
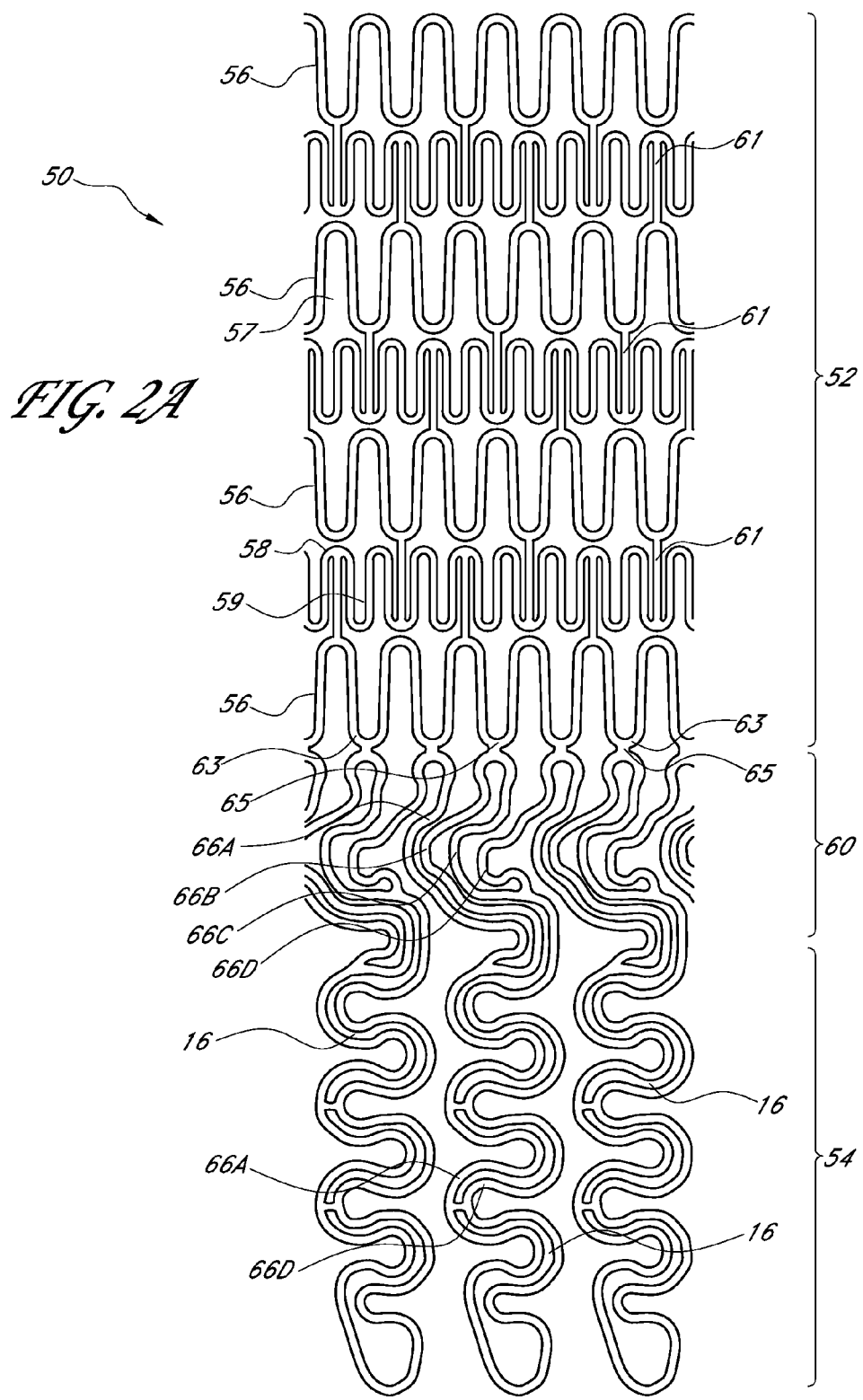

Referring now to FIG. 2A, an exemplary embodiment of a prosthesis 50 (shown in a "rolled out" pattern) comprises a support or stent section 52 and a frond section 54. Support section 52 comprises a first plurality of radially expansible serpentine elements 56 which extend circumferentially to form a cylindrical ring having a plurality of open areas or cells 57 therein. The cylindrical rings formed by serpentine elements 56 are coaxially aligned along the longitudinal axis of the support section 52, and, in the illustrated embodiment, alternate with a second plurality of cylindrical rings formed by radially expandable serpentine elements 58 defining a second set of smaller cells 59. Strut coverage in the range of from about 10% to about 20%, and in some embodiments between about 16%-18% by area is contemplated. A plurality of spaced apart, axially extending struts 61 connect adjacent rings. The particular pattern illustrated for this structure is well-known and chosen to be exemplary of a useful prosthesis. It will be appreciated that a wide variety of other conventional stent structures and patterns may be equally useful as the support section of the prostheses of the present invention. See, for example, FIGS. 2B-2F.

The wall patterns can be varied widely as desired to provide additional coverage, transition in axial stiffness, and accommodate various side branch angles with respect to the main vessel long axis as well as ostial geometries, i.e., diameter and shape.

The support section 52 is joined to the frond section 54 at a plurality of points 65 along a transition line or zone 60. Individual fronds 16, comprise a circumferentially expandable wall pattern. In the embodiment illustrated in FIG. 2A, each frond comprises four curving elements 66 at the distal end of the transition zone 60, which reduce in number to three and then to two in the axial (proximal) direction away from the stent 52. The particular structures shown illustrate one example of a way to achieve circumferential expansion of the individual fronds as the prosthesis is expanded. This is accomplished since each frond is attached to three adjacent serpentine ring apexes 63 in the proximal most serpentine ring 56. Thus, as these serpentine rings 56 are expanded, the circumferential distance between adjacent apexes 63 will increase, thereby causing each frond to "widen" by expanding in a circumferential direction. It would be possible, of course, to join each of the fronds 16 only at a single location to the prosthesis 52, thus allowing the anchors to be deployed without radial expansion. Two or four or more points of attachment may also be used, depending upon the wall pattern and desired performance of the resulting prosthesis. The struts in the transition section are designed to "cup" with adjacent struts such that the gap formed within and between fronds in the expanded prosthesis is minimized.

The circumferentially expandable fronds are curved about the longitudinal axis of the prosthesis and have a number of hinge regions which increase their conformability upon circumferential expansion by a balloon, as described hereinafter. Such conformability is desirable since the fronds will be expanded under a wide variety of differing anatomical conditions which will result in different final geometries for the fronds in use. The final configuration of the fronds in the main vessel lumen will depend on a number of factors, including length of the fronds and geometry of the vasculature and will vary greatly from deployment to deployment. While the fronds together will cover at least a portion of the main vessel wall circumference, most fronds will also be deformed to cover an axial length component of the main vessel wall as well. Such coverage is schematically illustrated in the figures discussed below.

In other embodiments, prosthesis structure 50 can include four or five or six or more fronds 16. Increasing the number of fronds provides an increased number of anchor points between a branch vessel stent and a main vessel stent. This may serve to increase the mechanical linkage between stent 10 and another stent deployed in an adjacent vessel. In various embodiments, fronds 16 can be narrower (in width) than embodiments having few fronds so as to increase the flexibility of the fronds. The increased flexibility can facilitate the bending of the fronds during stent deployment including bending from the branch body lumen into the main body lumen.

Figure 2B:
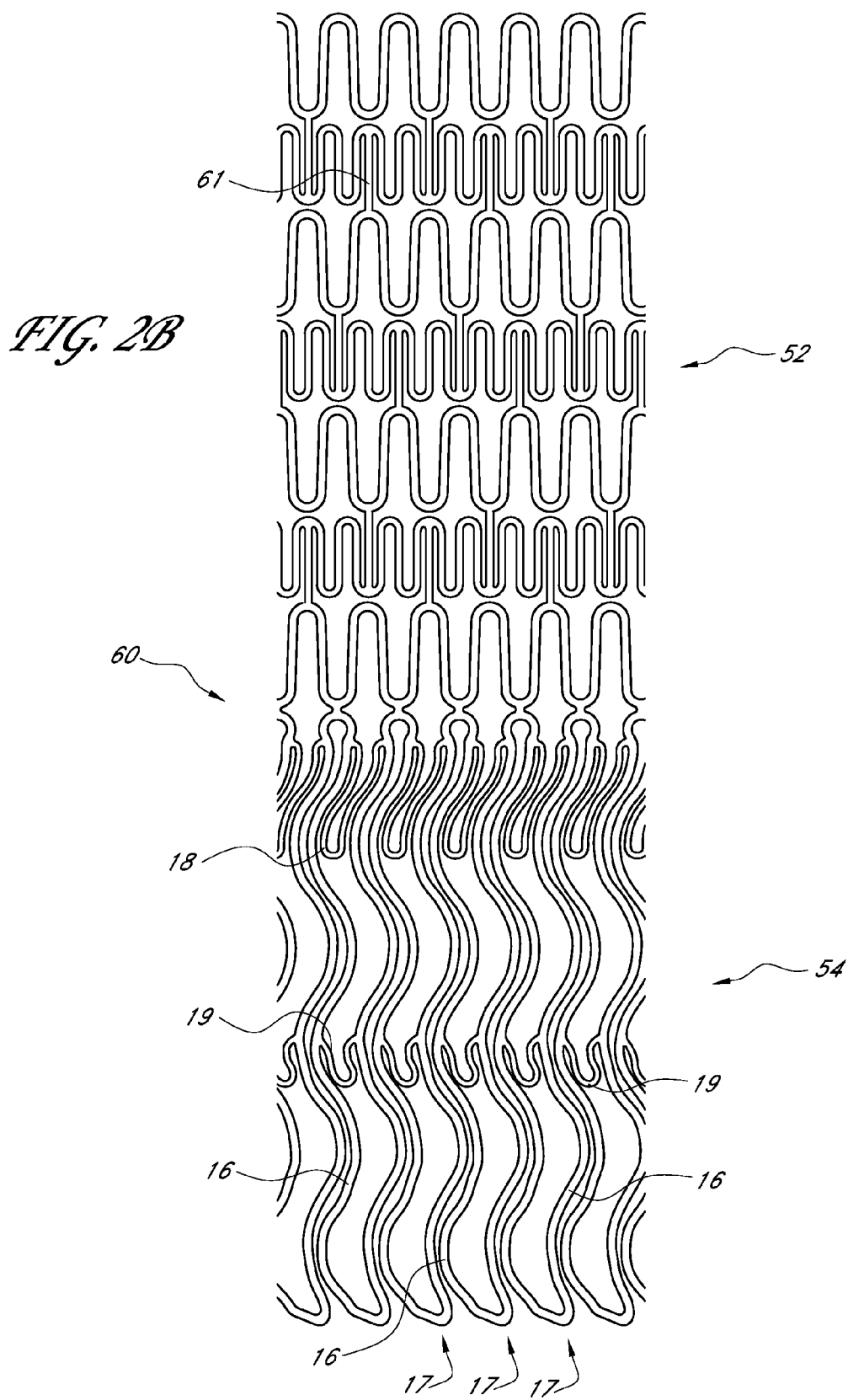

Referring now to FIG. 2B, in various embodiments, fronds 16 can comprise thin filaments formed into loops 17. An exemplary embodiment of a prosthesis structure 50 having a plurality of filament loops 17 is shown in FIG. 2B in a rolled out pattern. In various embodiments filament loops 17 can have at least one or two or more intra-filament connectors 18, 19 which extend in a circumferential direction to connect two adjacent filaments defining a filament loop 17. Connectors

18, 19 preferably include at least one nonlinear undulation such as a "U", "V" or "W" or "S" shape to permit radial expansion of the prosthesis in the vicinity of the fronds. (The intra-filament space may be crossed with a balloon catheter and dilated to larger diameters).

The illustrated embodiment includes a first intra-filament connector 18 in the transition area 60 for each frond 16, and a second connector 19 positioned proximally from the first connector 18. One or both of the first and second connectors 18, 19 can be configured to expand or otherwise assume a different shape when the fronds are deployed. At least five or ten or 20 or more connectors 18, 19 may be provided between any two adjacent filaments 66 depending upon the desired clinical performance. Also connectors 18, 19 can be continuous with frond loops 17 and have substantially the same cross sectional thickness and/or mechanical properties. Alternatively, connectors 18, 19 can have different diameters and/or mechanical properties (e.g, one or more of increased elasticity, elastic limit, elongation, stiffness etc.) and/or biological properties (surface finish, passivation, coatings, etc.). In one embodiment the distal connector 18 can be stiffer than the proximal connector 19 so as to allow more flexibility at the proximal tip of the fronds.

Connectors 18 and 19 can be further configured to perform several functions. First, to act as mechanical struts to increase the stiffness (e.g. longitudinal, torsional, etc) of the filament fronds 16. Second, when the fronds are deployed, connectors 18 and 19 can be designed to assume a deployed shape which provides radial mechanical support (e.g. act as prosthesis) to the target vessel including at the OS. This is particularly the case for first connector 18 which can be configured to unfurl in the circumferential direction and assume a semi-triangular shape in its deployed state with an expansion axis (of the connected points of the triangle to fronds) substantially parallel to the radial axis of the vessel. This configuration of connector 18 serves to provide radial mechanical support as well as coverage at the OS in particular. Connector 18 can also be configured to assume other deployed shapes as well, such as semi-circular etc. The number and spacing and deployed shape of the connectors 18 can be configured to provide the same amount or density at the OS (e.g. number of struts per axial or radial length of tissue) as the stent region 52 of the prosthesis provides to the rest of the vessel. In general, by varying the dimensions and number of the filaments 66 and connectors 18 any of a variety of physical properties can be achieved. The connectors 18 and 19 and filaments 66 may be selected and designed to cooperate to provide maximum area coverage, and/or maximum mechanical radial force, or either objective without the other. The number of filaments can be in the range of from about 3 to about 30, with specific embodiments of 4, 6, 10, 20 and 25.

In various embodiments, the arrangement of the filaments fronds can be configured to provide several functions. First, as described above they can be configured to provide increased coverage and hence patency of the Os by having an increased number of mechanical support points in the Os and hence a more even distribution of force (e.g. radial force) on the fronds. Also, for embodiments of drug coated stents, including drug eluting stents they provide an increased amount of surface area for the elution of the drug. This in turn, serves to provide increased and/or more constant local concentration of the selected drug at the vessel wall and/or other target site. Other pharmacokinetic benefits can be obtained as well, such as a more constant drug release rate. For stents coated with anti-cell proliferative, anti-inflammatory and/or anti-cell migration drugs such as Taxol (paclitaxel), Rapamycin and their derivatives, the use of high filament type fronds serve as a means to reduce the incidence and rate of hyperplasia and restenosis. Similar results can be obtained with other drugs known in the art for reducing restenosis (e.g. anti-neo-plastics, anti-inflammatory drugs, etc.). Also in a related embodiment the filament fronds can be coated with a different drug and/or a different concentration of drug as the remainder of the stent. In use, such embodiment can be configured to provide one or more of the following: i) a more constant release rate of drug; ii) bimodal release of drug; iii) multi drug therapies; and iv) titration of drug delivery/concentration for specific vessels and/or release rates. As disclosed in additional detail below, the drug may be incorporated into a biostable, biodegradable, or bioerodable polymer matrix, and may be optimized for long-term pharma release (prophylactic local drug delivery).

In general, in any of the embodiments herein, the prosthesis of the present invention can be adapted to release an agent for prophylactic or active treatment from all or from portions of its surface. The active agents (therapy drug or gene) carried by the prosthesis may include any of a variety of compounds or biological materials which provide the desired therapy or desired modification of the local biological environment. Depending upon the clinical objective in a given implementation of the invention, the active agent may include immunosuppressant compounds, anti-thrombogenic agents, anti-cancer agents, hormones, or other anti-stenosis drugs. Suitable immunosuppressants may include ciclosporin A (CsA), FK506, DSG(15-deoxyspergualin, 15-dos), MMF, rapamycin and its derivatives, CCI-779, FR 900520, FR 900523, NK86-1086, daclizumab, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, and steroids. Suitable anti-thrombogenic drugs may include anti-platelet agents (GP IIb/IIIa, thienopyridine, GPIb-IX, ASA, etc and inhibitors for the coagulation cascade (heparin, hirudin, thrombin inhibitors, Xa inhibitors, VIIa Inhibitors, Tissue Factor Inhibitors and the like). Suitable anti-cancer (anti proliferative) agents may include methotrexate, purine, pyridine, and botanical (e.g, paclitaxel, colchicines and triptolide), epothilone, antibiotics, and antibodies. Suitable additional anti-stenosis agents include batimastat, NO donor, 2-chlorodeoxyadenosine, 2-deoxycoformycin, FTY720, Myfortic, ISA (TX) 247, AGI-1096, OKT3, Medimmune, ATG, Zenapax, Simulect, DAB486-IL-2, Anti-ICAM-1, Thymoglobulin, Everolimus, Neoral, Azathioprine (AZA), Cyclophosphamide, Methotrexate, Brequinar Sodium, Leflunomide, or Mizoribine. Gene therapy formulations include Keratin 8, VEGF, and EGF, PTEN, Pro-UK, NOS, or C-myc may also be used.

Any of the coatings described herein may be provided on either the lumenal surface, the ablumenal surface, or both, on the prosthesis disclosed herein. In addition, coatings may be provided on only the support portion, only the frond portion, only the transition portion, or any combination thereof, depending upon the desired clinical performance. In addition to the coatings described above, at least a portion of the prosthesis may be provided with a coating which renders the implant compatible for in vivo attachment and proliferation of cells on the surface thereof. This coating is preferably provided on the ablumenal surface of the implant, and may be omitted from the lumenal surface of the implant. In general, the coating may comprise a therapeutically effective amount of an antibody which reacts with an endothelial cell surface antigen, to facilitate cellular proliferation on the surface of the implant. Additional details of antibody coatings to promote endothelial cell adherence may be found in U.S. Pat. No.

7,037,332, entitled Medical Device with Coating that Promotes Endothelial Cell Adherence, issued May 2, 2006 to Kutryk, et al., the disclosure of which is incorporated in its entirety herein by reference.

Methods of preventing restenosis include inhibiting VSMC hyperplasia or migration, promoting endothelial cell growth, or inhibiting cell matrix proliferation with the delivery of suitable compounds from the prosthesis. Radiation, systemic drug therapy and combinations of the foregoing may also be used. The desired dose delivery profiles for the foregoing are in some cases reported in the literature, or may be optimized for use with the prosthesis of the present invention through routine experimentation by those of skill in the art in view of the disclosure herein.

Binding systems (e.g., chemical binding, absorbable and non absorbable polymeric coatings) for releasably carrying the active agent with the prosthesis are well known in the art and can be selected to cooperate with the desired drug elution profile and other characteristics of a particular active agent as will be appreciated by those of skill in the art.

In general, the drug(s) may be incorporated into or affixed to the stent in a number of ways and utilizing any biocompatible materials; it may be incorporated into e.g. a polymer or a polymeric matrix and sprayed onto the outer surface of the stent. A mixture of the drug(s) and the polymeric material may be prepared in a solvent or a mixture of solvents and applied to the surfaces of the stents also by dip-coating, brush coating and/or dip/spin coating, the solvent (s) being allowed to evaporate to leave a film with entrapped drug(s). In the case of stents where the drug(s) is delivered from micropores, struts or channels, a solution of a polymer may additionally be applied as an outlayer to control the drug(s) release; alternatively, the active agent may be comprised in the micropores, struts or channels and the active co-agent may be incorporated in the outlayer, or vice versa. The active agent may also be affixed in an inner layer of the stent and the active co-agent in an outer layer, or vice versa. The drug(s) may also be attached by a covalent bond, e.g. esters, amides or anhydrides, to the stent surface, involving chemical derivatization. The drug(s) may also be incorporated into a biocompatible porous ceramic coating, e.g. a nanoporous ceramic coating. The medical device of the invention is configured to release the active co-agent concurrent with or subsequent to the release of the active agent.

Examples of polymeric materials known for this purpose include hydrophilic, hydrophobic or biocompatible biodegradable materials, e.g., polycarboxylic acids; cellulosic polymers; starch; collagen; hyaluronic acid; gelatin; lactone-based polyesters or copolyesters, e.g., polylactide; polyglycolide; polylactide-glycolide; polycaprolactone; polycaprolactone-glycolide; poly(hydroxybutyrate); poly(hydroxyvalerate); polyhydroxy (butyrate-co-valerate); polyglycolide-co-trimethylene carbonate; poly(dioxanone); polyorthoesters; polyanhydrides; polyaminoacids; polysaccharides; polyphosphoesters; polyphosphoester-urethane; polycyanoacrylates; polyphosphazenes; poly(ether-ester) copolymers, e.g. PEO-PLLA, fibrin; fibrinogen; or mixtures thereof; and biocompatible non-degrading materials, e.g, polyurethane; polyolefins; polyesters; polyamides; polycaprolactam; polyimide; polyvinyl chloride; polyvinyl methyl ether; polyvinyl alcohol or vinyl alcohol/olefin copolymers, e.g, vinyl alcohol/ethylene copolymers; polyacrylonitrile; polystyrene copolymers of vinyl monomers with olefins, e.g., styrene acrylonitrile copolymers, ethylene methyl methacrylate copolymers; polydimethylsiloxane; poly(ethylene-vinylacetate); acrylate based polymers or copolymers, e.g, polybutylmethacrylate, poly(hydroxyethyl methylmethacrylate); polyvinyl pyrrolidinone; fluorinated polymers such as polytetrafluoroethylene; cellulose esters e.g. cellulose acetate, cellulose nitrate or cellulose propionate; or mixtures thereof.

When a polymeric matrix is used, it may comprise multiple layers, e.g. a base layer in which the drug(s) is/are incorporated, e.g. ethylene-co-vinylacetate and polybutylmethacrylate, and a top coat, e.g. polybutylmethacrylate, which is drug(s)-free and acts as a diffusion-control of the drug(s). Alternatively, the active agent may be comprised in the base layer and the active co-agent may be incorporated in the outlayer, or vice versa. Total thickness of the polymeric matrix may be from about 1 to 20μ or greater.

The drug(s) elutes from the polymeric material or the stent over time and enters the surrounding tissue, e.g. up to ca. 1 month to 10 years. The local delivery according to the present invention allows for high concentration of the drug(s) at the disease site with low concentration of circulating compound. The amount of drug(s) used for local delivery applications will vary depending on the compounds used, the condition to be treated and the desired effect. For purposes of the invention, a therapeutically effective amount will be administered; for example, the drug delivery device or system is configured to release the active agent and/or the active co-agent at a rate of 0.001 to 200 μg/day. By therapeutically effective amount is intended an amount sufficient to inhibit cellular proliferation and resulting in the prevention and treatment of the disease state. Specifically, for the prevention or treatment of restenosis e.g. after revascularization, or antitumor treatment, local delivery may require less compound than systemic administration. The drug(s) may elute passively, actively or under activation, e.g. light-activation.

A possible alternative to a coated stent is a stent containing wells or reservoirs that are loaded with a drug, as discussed by Wright et al., in "Modified Stent Useful for Delivery of Drugs Along Stent Strut," U.S. Pat. No. 6,273,913, issued Aug. 14, 2001; and Wright et al., in "Stent with Therapeutically Active Dosage of Rapamycin Coated Thereon," US patent publication US 2001/0027340, published Oct. 4, 2001, the disclosures of both of which are incorporated in their entireties herein by reference.

Wright et al. in U.S. Pat. No. 6,273,913, describes the delivery of rapamycin from an intravascular stent and directly from micropores formed in the stent body to inhibit neointimal tissue proliferation and restenosis. The stent, which has been modified to contain micropores, is dipped into a solution of rapamycin and an organic solvent, and the solution is allowed to permeate into the micropores. After the solvent has been allowed to dry, a polymer layer may be applied as an outer layer for a controlled release of the drug.

U.S. Pat. No. 5,843,172 by Yan, which is entitled "Porous Medicated Stent", discloses a metallic stent that has a plurality of pores in the metal that are loaded with medication. The drug loaded into the pores is a first medication, and an outer layer or coating may contain a second medication. The porous cavities of the stent can be formed by sintering the stent material from metallic particles, filaments, fibers, wires or other materials such as sheets of sintered materials.

Leone et al. in U.S. Pat. No. 5,891,108 entitled "Drug Delivery Stent" describes a retrievable drug delivery stent, which is made of a hollow tubular wire. The tubular wire or tubing has holes in its body for delivering a liquid solution or drug to a stenotic lesion. Brown et al. in "Directional Drug Delivery Stent and Method of Use," U.S. Pat. No. 6,071,305 issued Jun. 6, 2000, discloses a tube with an eccentric inner diameter and holes or channels along the periphery that house drugs and can deliver them preferentially to one side of the tube. Scheerder et al. in US patent publication US 2002/

0007209, discloses a series of holes or perforations cut into the struts on a stent that are able to house therapeutic agents for local delivery.

Referring to the patent literature, Heparin, as well as other anti-platelet or anti-thrombolytic surface coatings, have been reported to reduce thrombosis when carried by the stent surface. Stents including both a heparin surface and an active agent stored inside of a coating are disclosed, for example, in U.S. Pat. Nos. 6,231,600 and 5,288,711.

A variety of agents specifically identified as inhibiting smooth muscle-cell proliferation, and thus inhibit restenosis, have also been proposed for release from endovascular stents. As examples, U.S. Pat. No. 6,159,488 describes the use of a quinazolinone derivative; U.S. Pat. No. 6,171,609, describes the use of taxol, and U.S. Pat. No. 5,716,981, the use of paclitaxel, a cytotoxic agent thought to be the active ingredient in the agent taxol. The metal silver is cited in U.S. Pat. No. 5,873,904. Tranilast, a membrane stabilizing agent thought to have anti-inflammatory properties is disclosed in U.S. Pat. No. 5,733,327.

More recently, rapamycin, an immunosuppressant reported to suppress both smooth muscle cell and endothelial cell growth, has been shown to have improved effectiveness against restenosis, when delivered from a stent. See, for example, U.S. Pat. Nos. 5,288,711 and 6,153,252. Also, in PCT Publication No. WO 97/35575, the monocyclic triene immunosuppressive compound everolimus and related compounds have been proposed for treating restenosis, via systemic delivery.

Any one or a combination of the frond section, support section and transition may comprise a bioabsorbable material, which will degrade or otherwise dissipate over time. The bioabsorbable implant may be a convenient platform for the elution of any of a variety of biologically active agents, such as those identified above.

Prostheses in accordance with the present invention may comprise any of a variety of bioabsorbable polymers, depending upon the desired performance. These may include poly (alpha-hydroxy acid) such as polylactide [poly-L-lactide (PLLA), poly-D-lactide (PDLA)], polyglycolide (PGA), polydioxanone, polycaprolactone, polygluconate, polylactic acid-polyethylene oxide copolymers, poly(hydroxybutyrate), polyanhydride, polyphosphoester, poly(amino acids), or related copolymers materials, each of which have a characteristic degradation rate in the body. For example, PGA and polydioxanone are relatively fast-bioabsorbing materials (weeks to months) and PLA and polycaprolactone are relatively slow-bioabsorbing material (months to years).

Bioabsorbable PLLA and PGA material are degraded in vivo through hydrolytic chain scission to lactic acid and glycolic acid, respectively, which in turn is converted to $CO_2$ and then eliminated from the body by respiration. Heterogeneous degradation of semicrystalline polymers occurs due to the fact that such materials have amorphous and crystalline regions. Degradation occurs more rapidly at amorphous regions than at crystalline regions. This results in the product decreasing in strength faster than it decreases in mass. Totally amorphous, cross-linked polyesters show a more linear decrease in strength with mass over time as compared to a material with crystalline and amorphous regions. Degradation time may be affected by variations in chemical composition and polymer chain structures, and material processing.

Controlled release of a drug, via a bioabsorbable polymer, offers to maintain the drug level within the desired therapeutic range for the duration of the treatment. In the case of stents, the prosthesis materials may be selected to maintain vessel support for at least about two weeks or until incorporated into the vessel wall even with bioabsorbable, biodegradable polymer constructions.

Several polymeric compounds that are known to be bioabsorbable and hypothetically have the ability to be drug impregnated may be useful in prosthesis formation herein. These compounds include: poly-1-lactic acid/polyglycolic acid, polyanhydride, and polyphosphate ester. A brief description is provided below.

Poly-1-lactic acid/polyglycolic acid has been used for many years in the area of bioabsorbable sutures. It is currently available in many forms, i.e., crystals, fibers, blocks, plates, etc. These compounds degrade into non-toxic lactic and glycolic acids. There may, however, be several problems with this compound. The degradation artifacts (lactic acid and glycolic acid) are slightly acidic. The acidity can cause minor inflammation in the tissues as the polymer degrades. This same inflammation could be detrimental in coronary and peripheral arteries, i.e., vessel occlusion. Another potential problem associated with this polymer is the ability to control and predict the degradation behavior. It does not appear possible for the biochemist to accurately predict degradation time, which could be detrimental for a drug delivery device if dosing parameters need to be tightly controlled.

Other compounds which could be used are the polyanhydrides. They are currently being used with several chemotherapy drugs for the treatment of cancerous tumors. These drugs are compounded into the polymer which is molded into a cube-like structure and surgically implanted at the tumor site.

Polyanhydrides have weaknesses in their mechanical properties, due to low molecular weights. This drawback may make them difficult to process into a filament form such as for the fronds or transition section of the prostheses disclosed herein. Also, polyanhydrides have relatively poor solubility, making characterization and fabrication difficult.

A third class of compounds which may be preferred includes polyphosphate esters. Polyphosphate ester is a compound such as that disclosed in U.S. Pat. Nos. 5,176,907; 5,194,581; and 5,656,765 issued to Leong which are incorporated herein by reference. The polyphosphate esters have high molecular weights (600,000 average), yielding attractive mechanical properties. This high molecular weight leads to transparency, and film and fiber properties. It has also been observed that the phosphorous-carbon-oxygen plasticizing effect, which lowers the glass transition temperature, makes the polymer desirable for fabrication.

The basic structure of polyphosphate ester monomer is shown below.

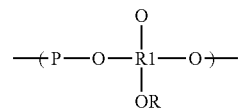

where

P corresponds to Phosphorous,

O corresponds to Oxygen, and R and R1 are functional groups.

Reaction with water leads to the breakdown of this compound into monomeric phosphates (phosphoric acid) and diols (see below).

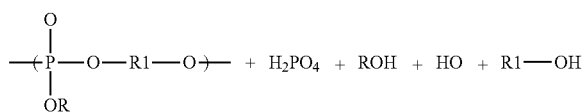

It is the hydrolytic instability of the phosphorous ester bond which makes this polymer attractive for controlled drug release applications. A wide range of controllable degradation rates can be obtained by adjusting the hydrophobicities of the backbones of the polymers and yet assure biodegradability.

The functional side groups allow for the chemical linkage of drug molecules to the polymer. This is shown below.

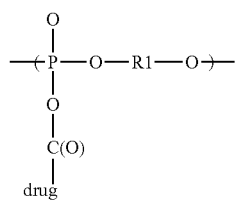

The drug may also be incorporated into the backbone of the polymer.

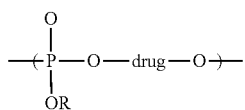

The highly hydrolytically reactive phosphorous ester bond, the favorable physical properties, and the versatile chemical structure may make the polyphosphate esters a superior drug delivery system for a prosthesis. See U.S. Pat. No. 5,545,208 to Wolff, the disclosure of which is incorporated in its entirety herein by reference.

Use of multiple filaments per frond also provides for a more open structure of the fronds section 54 of the prosthesis to allow for an easier and less obstructed passage of a guide wire and/or the deployment balloon by and/or through the fronds (e.g., during un-jailing procedures known in the art). Similarly, use of the flexible filaments also allows the main vessel to track between fronds and engage the main vessel stent. In particular, the thinner frond filaments facilitate advancement of the fronds over the circumference and/or the length of a main vessel stent during deployment of the fronds or the main vessel stent. Moreover, the filaments can be configured to be easily withdrawn and then re-advanced again to allow for repositioning of either of the branch vessel stent. Other means for facilitating advancement of the main vessel stent between the fronds can include tapering the fronds and/ or coating the fronds with a lubricous coating such as PTFE or silicone (this also facilitates release of the fronds from constraining means described herein). Finally, by having an increased number of filaments, the mechanical support of the Os is not compromised if one or more filaments should become pushed aside during the stent deployment. That is, the remaining filaments provide sufficient support of the Os to maintain it patency. In these and related embodiments, it may be desirable to have at least six loops 17 each comprising at least one filament looped back upon itself at its proximal limit to provide at least two elements per frond.

Various embodiments of the fronds can be configured to provide an increased amount of mechanical linkage between the fronds and the main vessel stent. In general, the frond design seeks to 1) track to site, 2) allow for advancement of MV Stent 3) increase frond-MV stent interaction and 4) frond MV wall interactions. Another means includes increasing the number of fronds to provide an increased number of anchor points between a branch vessel stent and a main vessel stent. This in turn provides an increased amount of mechanical linkage between the two stents such that they increasingly operate mechanically as one structure rather than two after deployment. This also serves to improve the spatial stability of the deployed stents within both vessels. That is, there is reduced movement (e.g., axial or radial) or reduced possibility of movement of one or both stents within their respective vessels. In particular, the linkage serves to provide radial strength of the structure in the ostium.

Figure 2C:
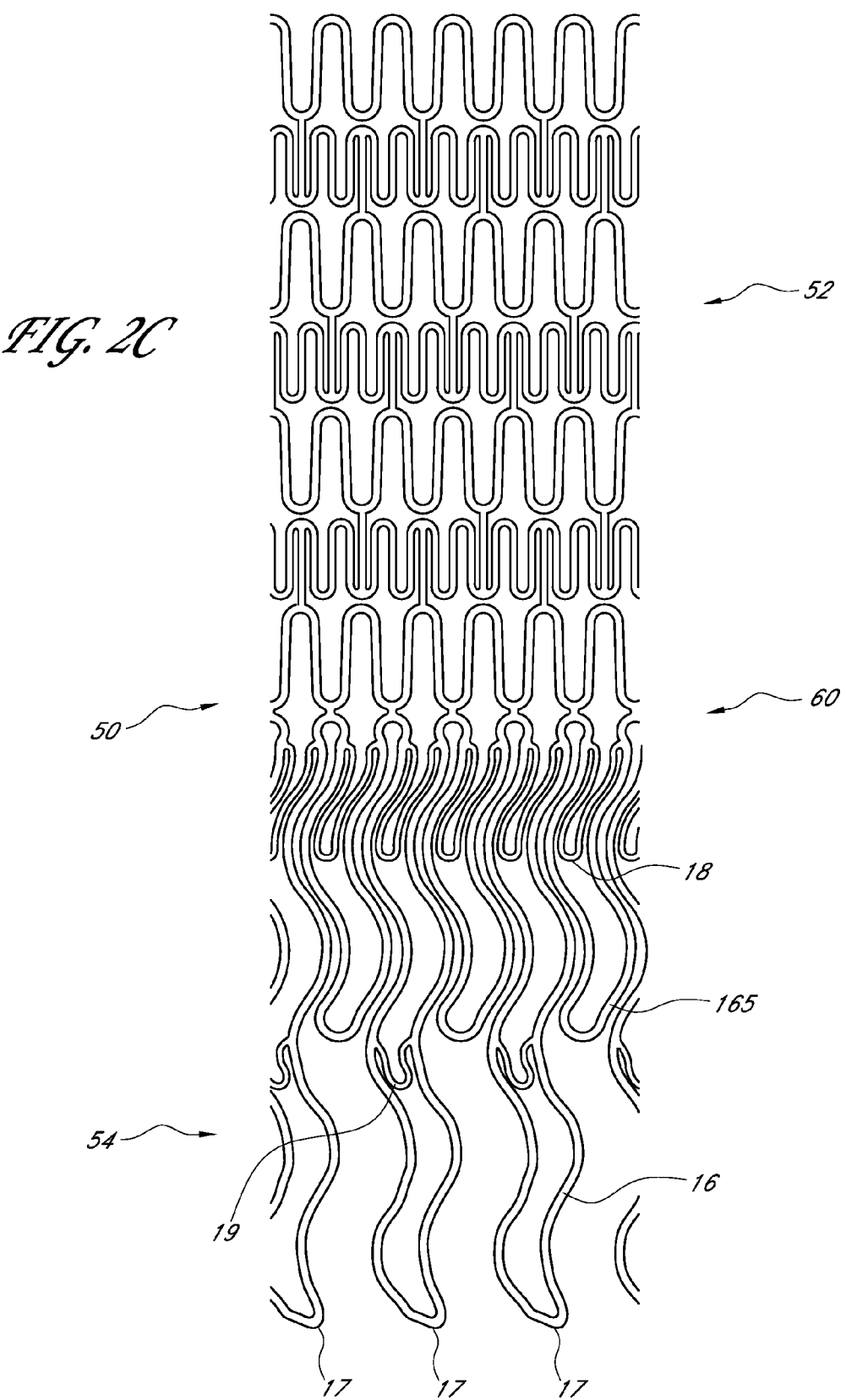

Referring now to FIG. 2C in an alternative embodiment of a prosthesis 50 having filament fronds 17, one or two or more frond can be a shortened frond 16s. That is a frond that is shortened in the longitudinal direction. In the illustrated embodiment, shortened fronds 16s and full length fronds 16 alternate around the circumference of the stent. The amount of shortening can range from 10% to 99%. In a preferred embodiment, fronds 16s are shortened by approximately slightly less than 50% in length from the length of un-shortened fronds 16. Embodiments having shortened fronds, reduce the likelihood of resistance when the main vessel stent 150 is positioned. Shortened fronds 16s also can be configured to act more like point contacts on the main vessel stent 150 and should therefore be less likely to be swept towards the Os by deployment and/or misalignment of the main vessel stent and deployment balloon. Also, use of less material in the fronds tends to produce less displacement of the fronds even if the main vessel stent or balloon catches multiple fronds, and may produce a lower biological reaction (less foreign material).

Figure 2E:
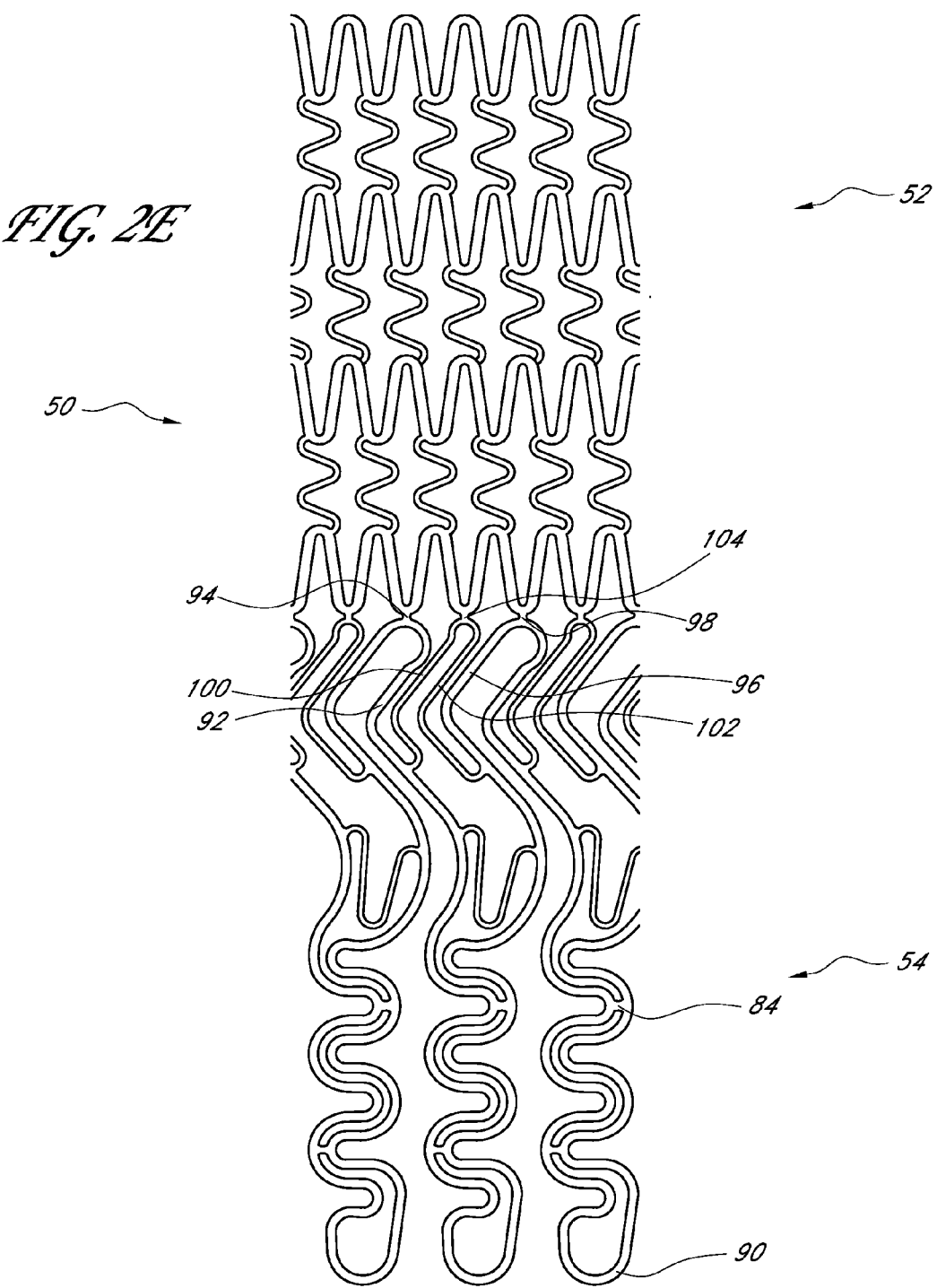

FIGS. 2D and 2E illustrate an alternative side wall patterns for the transition portion of the prosthesis of the present invention, on stents having two different side wall patterns. As described previously, the specific stent or other support structure configuration may be varied considerably within the context of the present invention.

In each of the embodiments of FIGS. 2D and 2E, the struts 70 at the frond root (e.g. transition zone) are provided with an interdigitating or nesting configuration. In this configuration, as viewed in the flat, laid out view as in FIGS. 2D and 2E, a plurality of struts 70 extend across the transition zone. A distal segment 72 of each strut 70 inclines laterally in a first direction, to an apex 74, and then inclines laterally in a second direction to a point that may be approximately axially aligned with a distal limit of the distal segment 72. The extent of lateral displacement of the strut between its origin and the apex 74 is greater than the distance between adjacent struts, when in the unexpanded configuration. In this manner, adjacent struts stack up or nest within each other, each having a concavity 78 facing in a first lateral direction and a corresponding convexity 80 in a second lateral direction. This configuration seeks to optimize vessel wall coverage at the ostium, when the stent is expanded.

The axial length of each frond is at least about 10%, often at least about 20%, and in some embodiments at least about 35% or 75% or more of the length of the overall prosthesis. Within this length, adjacent fronds may be constructed without any lateral interconnection, to optimize the independent flexibility. The axially extending component of the frond may be provided with an undulating or serpentine structure 82, which helps enable the fronds to rotate out of the plane when the main vessel stent is deployed. Circumferential portions of the undulating fronds structure make the frond very flexible out of the plane of the frond for trackability. A plurality of connectors 84 are provided between parallel undulating filaments 86, 88 of each frond, to keep the frond from being overly floppy and prone to undesirable deformation. Each of the fronds in the illustrated embodiment has a broad (i.e. relatively large radius) frond tip 90, to provide an atraumatic tip to minimize the risk of perforating the arterial or other vascular wall.

The interdigitating construction in the transition zone, as well as the undulating pattern of the frond sections both provides optimal coverage at the ostium, and provides additional strut length extension or elongation capabilities, which may be desirable during the implantation process.

It may also be desirable to vary the physical properties of the filaments 86, 88, or elsewhere in the prosthesis, to achieve desired expansion results. For example, referring to FIG. 2E, each frond 16 includes a first filament 92, attached at a first attachment point 94 and a second filament 96 attached at a second attachment point 98 to the stent. A third filament 100 and a fourth filament 102 are connected to the stent at an intermediate attachment point 104. As illustrated, the transverse width of the third and fourth filaments 100 and 102 are less than the transverse width of the first and second filaments 92, 96. The thinner filaments 100, 102 provide less resistance to expansion, and help maintain optimal coverage in the vicinity of the ostium upon expansion of the prosthesis.

In any of the embodiments described herein, the fronds may be considered to have a lumenal surface at least a portion of which will be in contact with an outside surface of the main vessel stent, and an ablumenal surface which will be pressed into contact with the vascular wall by the main vessel stent. The lumenal and ablumenal surfaces of the fronds may be provided with similar or dissimilar characteristics, depending upon the desired performance. For example, as described elsewhere herein, the frond and particularly the ablumenal surface may be provided with a drug eluting characteristic.

It may also be desirable to modify the lumenal surface of the frond, to enhance the physical interaction with the main vessel stent. For this purpose, the lumenal surface of the frond may be provided with any of a variety of friction enhancing surface characteristics, or engagement structures for engaging the main vessel stent. Friction enhancing surfaces may comprise the use of polymeric coatings, or mechanical roughening such as laser etching, chemical etching, sputtering, or other processes. Alternatively, any of a variety of radially inwardly extending hooks or barbs may be provided, for engaging the main vessel stent. Preferably, any radially inwardly extending hooks or barbs will have an axial length in the radial direction of no greater than approximately the wall thickness of the main vessel stent strut, to minimize the introduction of blood flow turbulence. Although a variety of main vessel stents are available, the inventors presently contemplate wall thicknesses for the struts of such main vessel stents to be on the order of about 0.003 to 0.0055 inches for native coronary indications. Any of the foregoing surfaces textures or structures may also be provided on the ablumenal surface of the main vessel stent, to cooperate with corresponding textures or structures on the fronds, to enhance the physical integrity of the junction between the two, and potentially reduce the risk for vessel perforation by fronds.

As will be described in additional detail in connection with the method, below, proper positioning of the prosthesis with respect to the bifurcation may be important. To facilitate positioning of the transition zone relative to the carina or other anatomical feature of the bifurcation, the prosthesis is preferably provided with a first radiopaque marker at a distal end of the transition zone and a second radiopaque marker at the proximal end of the transition zone. The proximal and distal radiopaque markers may take the form of radiopaque bands of material, or discreet markers which are attached to the prosthesis structure. This will enable centering of the transition zone on a desired anatomical target, relative to the ostium of the bifurcation. In general, it is desirable to avoid positioning the stent or other support such that it extends into the main vessel. A single marker may be used to denote the placement location of the transition zone.

Alternatively, the marker band or bands or other markers may be carried by the deployment catheter beneath the prosthesis, and axially aligned with, for example, the proximal and distal ends of the transition zone in addition to markers delineating the proximal and distal end of the prosthesis.

Although the prosthesis has been disclosed herein primarily in the context of a distal branch vessel stent carrying a plurality of proximally extending fronds, other configurations may be constructed within the scope of the present invention. For example, the orientations may be reversed such that the fronds extend in a distal direction from the support structure. Alternatively, a support structure such as a stent may be provided at each of the proximal and distal ends of a plurality of frond like connectors. This structure may be deployed, for example, with a distal stent in the branch lumen, a plurality of connectors extending across the ostium into the main vessel, and the proximal stent deployed in the main vessel proximal to the ostium. A separate main vessel stent may thereafter be positioned through the proximal stent of the prosthesis, across the ostium and into the main vessel on the distal side of the bifurcation.

In addition, the prosthesis has been primarily described herein as a unitary structure, such as might be produced by laser cutting the prosthesis from a tubular stock. Alternatively, the prosthesis may be constructed such as by welding, brazing, or other attachment techniques to secure a plurality of fronds onto a separately constructed support. This permits the use of dissimilar materials, having a variety of hybrid characteristics, such as a self expandable plurality of fronds connected to a balloon expandable support. Once released from a restraint on the deployment catheter, self expandable fronds will tend to bias radially outwardly against the vascular wall, which may be desirable during the process of implanting the main vessel stent. Alternatively, the entire structure can be self expandable or balloon expandable, or the support can be self expandable as is described elsewhere herein. In general, the proximal end of the fronds will contribute no incremental radial force to the prosthesis. The distal end of the fronds may contribute radial force only to the extent that it is transmitted down the frond from the support structure.

In each of the embodiments illustrated in FIGS. 2A-2E, the fronds have been illustrated as extending between a first end which is attached to the support 52, and a second, free end. In any of the frond designs disclosed herein, it may be desirable to provide a connection between the fronds in the vicinity of the free end. The connection may be accomplished in any of a variety of ways, such as providing a series of interfrond segments or connections, which, when deployed and expanded, form a circumferential ring which links the fronds. Alternatively, the circumferential link may be frangible, such that it maintains the spatial orientation of the fronds prior to a final expansion step, but is severed or otherwise releases the fronds upon final expansion.

The provision of a circumferential link at the proximal end of the fronds may provide a variety of benefits. For example, in an embodiment intended for balloon expansion at the treatment site, the circumferential link will assist in maintaining the crimped profile of the fronds on the balloon during transluminal navigation. The circumferential link may be configured with sufficient holding force that an outer sleeve such as those discussed in connection with FIGS. 5 and 6 may be omitted. In addition, the provision of a circumferential link may provide sufficient radiopacity either by itself or by carrying separate radiopaque markers to permit visualization of the ends of the fronds.

Once at the treatment site, the circumferential link will assist in maintaining the spacing of the fronds and also in holding the proximal ends of the fronds open to facilitate advancement of the main vessel stent therethrough. The circumferential link may additionally assist in controlling the fronds if, during the procedure, it is determined to crush the fronds against a wall of the vessel. The circumferential link will assist in maintaining the fronds against the wall while a secondary strategy is employed.

The circumferential link may be provided by any of a variety of techniques which will be understood to those in the stent manufacturing arts. For example, the circumferential link may be formed integrally with the stent and fronds such as by laser cutting from tube stock. Alternatively, the circumferential link may be attached to previously formed fronds, using any of a variety of bonding techniques such as welding, brazing, adhesives or others depending upon the materials of the fronds and circumferential link. Although it may add to the wall thickness, the circumferential link may be interlocked with or crimped to the fronds.

The circumferential link may alternatively be a polymeric band or tubular sleeve. For example, a radially expandable tubular sleeve may be positioned around the outside surface of the fronds, or adjacent the lumenal surface of the fronds. A polymeric circumferential link may also be formed such as by dipping the fronds or spraying the fronds with a suitable polymeric precursor or molten material. Polymeric circumferential links may be permanent, severable, or may be bioabsorbable or bioerodeable over time.

Figure 2F:
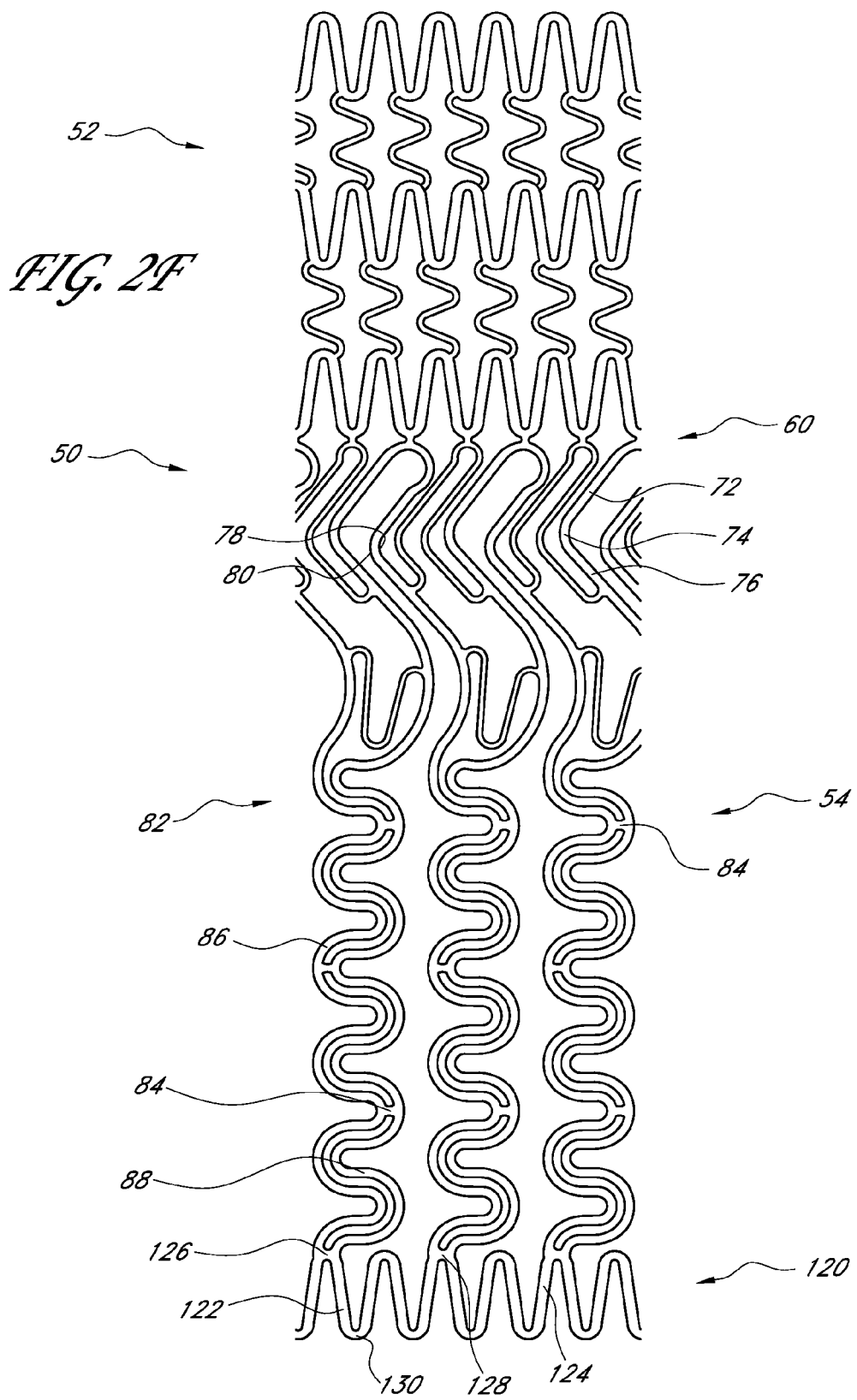
FIG. 2F is a lateral view as in FIG. 2D, with the added feature of a circumferential link to assist in maintaining the spatial orientation of the fronds.

One embodiment of a circumferential link is illustrated schematically in FIG. 2F. In this embodiment, a circumferential link 120 is provided, which connects each adjacent pair of fronds together, to produce a circumferential link 120 which extends completely around the axis of the prosthesis. In this illustration, the circumferential link 120 thus comprises a discrete transverse connection between each adjacent pair of fronds. Thus, for example, a first segment 122 is provided between a first and a second frond. The first segment 122 is expandable or enlargeable in a circumferential direction. A first segment 122 has a first end 126 at the point of attachment of the first segment 122 to a first frond, and a second end 128 at a point of attachment between the first segment 122 and a second frond. The arc distance or the linear distance between the first end 126 and second end 128 measured in a plane transverse to the longitudinal axis of the prosthesis is enlargeable from a first distance for transluminal navigation, to a second distance following expansion of the fronds within the main vessel. To accommodate the radial expansion of the circumferential link 120, the first segment 122 is provided with an undulating configuration having at least one and optionally 2 or three or more apex 130, as will be understood in the art. In one embodiment, each adjacent pair of fronds is connected by a transverse segment (e.g., 122, 124 etc.) and each of the transverse segments is identical to each other transverse segments.

Although the first segment 122 and second segment 124 are each illustrated in FIG. 2F as comprising only a single transversely extending filament, two or three or more filaments may be provided between each adjacent pair of fronds, depending upon the desired performance. As used herein, the term "circumferential link" does not limit the link 120 to only a single filament between adjacent fronds. For example, the circumferential link may comprise a stent or other support structure which is similar to the support structure 52.

Figure 2G:
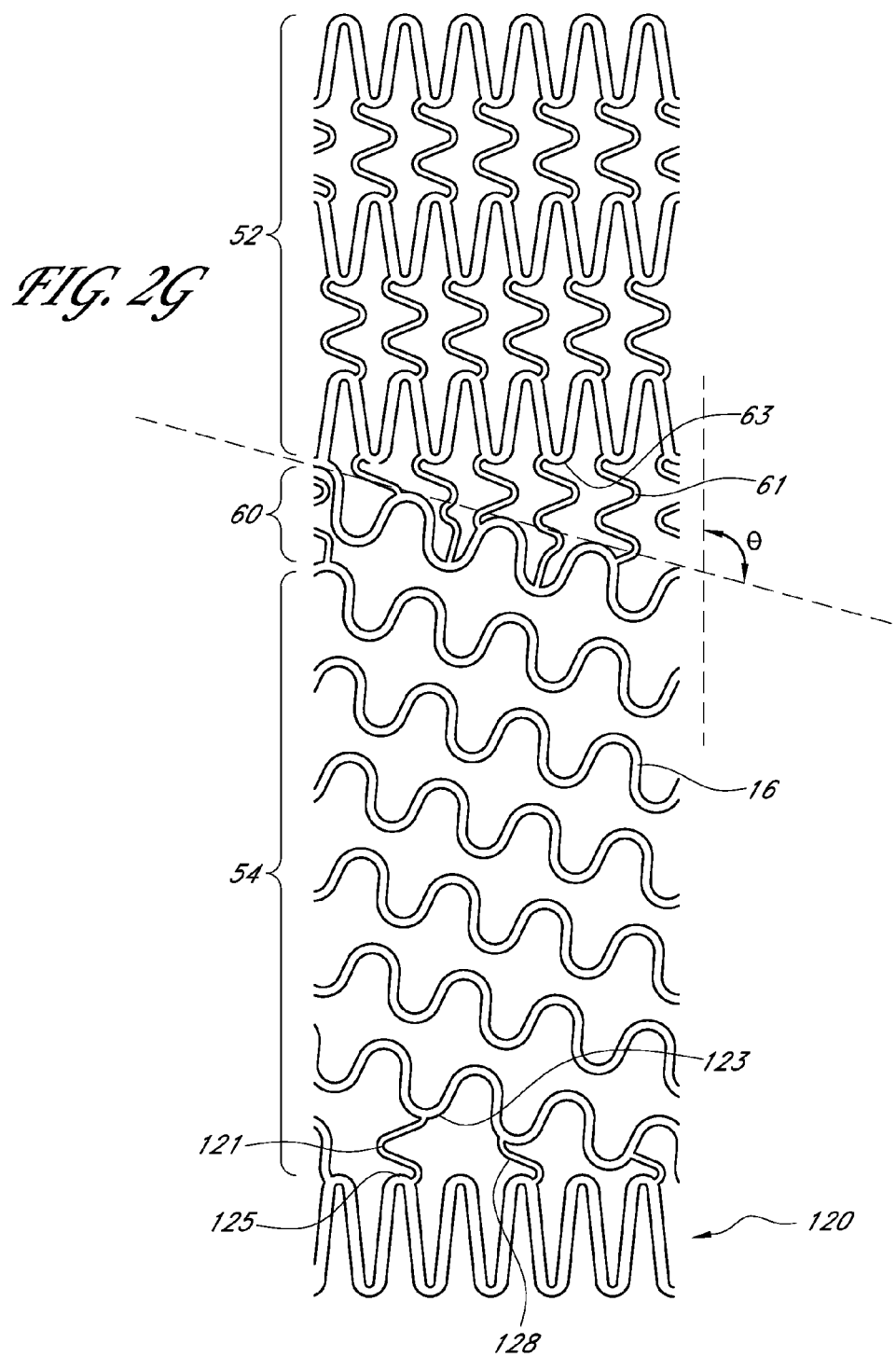
FIG. 2G is a lateral view as in FIG. 2F, having a helical frond.

Referring to FIG. 2G, there is illustrated a prosthesis in accordance with the present invention illustrating a spiral frond configuration. In general, the prosthesis 50 comprises a support section 52 and a frond section 54 generally as has been discussed previously. Depending upon the desired performance characteristics, a transition section 60 may be provided between the support section 52 and the frond section 54. In the illustrated embodiment, the proximal end of the frond section 54 is provided with a circumferential link 120 as has been discussed.

The frond section 54 comprises a single frond 16, in the illustrated embodiment in the form of a single wire or filament, which extends in a spiral configuration about the longitudinal axis of the prosthesis. The frond 16 may comprise a single filament as illustrated, or may comprise a more complex, fenestrated or multi-filament configuration as has been discussed herein.

The frond 16 is additionally formed into a sinusoidal configuration, alternately having concavities facing in a proximal direction and concavities facing distally. In the illustrated embodiment, the frond 16 is provided with a sinusoidal pattern having a plurality of generally oppositely facing substantially constant radius curves. The fronds 16 may alternatively comprise a plurality of "U" shaped or "V" shaped undulations, or other configuration depending upon the desired clinical performance.

In the illustrated embodiment, a single frond 16 extends in a spiral about the longitudinal axis of the prosthesis 50. Alternatively, two fronds 16 or three fronds 16 or more may be utilized, each spiraling about the longitudinal axis, as will be apparent to those of skill in the art in view of the disclosure herein.

The spiral frond 16 will generally extend for at least two complete revolutions about the longitudinal axis of the prosthesis. The frond 16 will often extend through at least about 4 complete revolutions, and, in some embodiments, at least about 6 complete revolutions about the longitudinal axis of the prosthesis. The axial length of the frond section 54 in a helical frond embodiment will often be at least about 25% of the overall, unstretched length of the prosthesis. In certain embodiments, the axial length of the frond section 54 will be at least about 30% of the overall unstretched length of the prosthesis.

At the distal end of the frond section 54, a connection is made to the support section 52. In the illustrated embodiment, a plurality of connectors 61 is provided. Connectors 61 may conveniently be formed integrally with or attached to the support section 52 at any of a variety of locations, such as on one or more apexes 63. The connectors 61 extend from the apex 63 to the frond 16, such as on a distally convex curve or a distally concave curve of the frond 16. One or two or three or four or more connectors 61 may be utilized to connect the frond 16 to the support section 52. In the illustrated embodiment, each apex 63 on the proximal end of the support section 52 is provided with a unique connector 61, for connection to the frond 16. As can be appreciated by those of skill in the art, the axial length of the connectors 61 will enlarge progressively at progressive circumferential positions about the axis of the support section 52, to accommodate the inclined angle of the distal most loop of frond 16, which, due to its spiral configuration, resides on a transverse plane which is inclined at an angle θ with respect to the longitudinal axis of the prosthesis 50. In spiral frond embodiments, the angle θ can be within the range of from about 95° to about 170°. In spiral frond embodiments, the angle θ can be within the range of from about 95° to about 135°. In spiral frond embodiments, the angle θ can be about 110°.

In the embodiment illustrated in FIG. 2G, the proximal end of the frond 16 is provided with a circumferential link 120. Circumferential link 120 may be connected to the frond 16 in a variety of ways, such as by providing one or more connectors 121. Connector 121 is illustrated as connected to or formed with an apex 123 on the sinusoidal frond 16, and also to a distally facing apex 125 on the circumferential link 120. A second connector 128 is illustrated, similarly connected between a proximally facing convexity on the frond 16 and a distally facing convexity on the circumferential link 120. In the illustrated embodiment, every other apex 125 on the circumferential link 120 is provided with a connector for connection to the frond 16. Alternatively, every third apex 125 or every apex 125 may be connected to the frond 16 by a connector 121.

In many ways the prosthesis illustrated in FIG. 2G may be utilized in a manner similar to other prostheses disclosed herein. However, the spiral configuration of fronds 16 provides a greater level of radial support than many of the other frond configurations disclosed herein. As a consequence, the spiral frond configuration may also be utilized as a provisional side branch stent while other configurations may lack sufficient radial force to be used in this manner. In a provisional stenting, the stent is placed in the side branch and then evaluated for whether a second stent is desirable. The spiral wound frond exhibits sufficient radial force that it may be used either alone or with a second stent. If a second stent is desired, it may be advanced through the side wall of the spiral frond 16 and into the main vessel as has been discussed. Alternatively, the spiral frond prosthesis may be left as a single stent, depending upon the desired clinical performance.

In addition, the spiral fronds support the cantilevered transition zone 60 such that radial strength is provided within the ostium of the bifurcation.

Figure 2H:
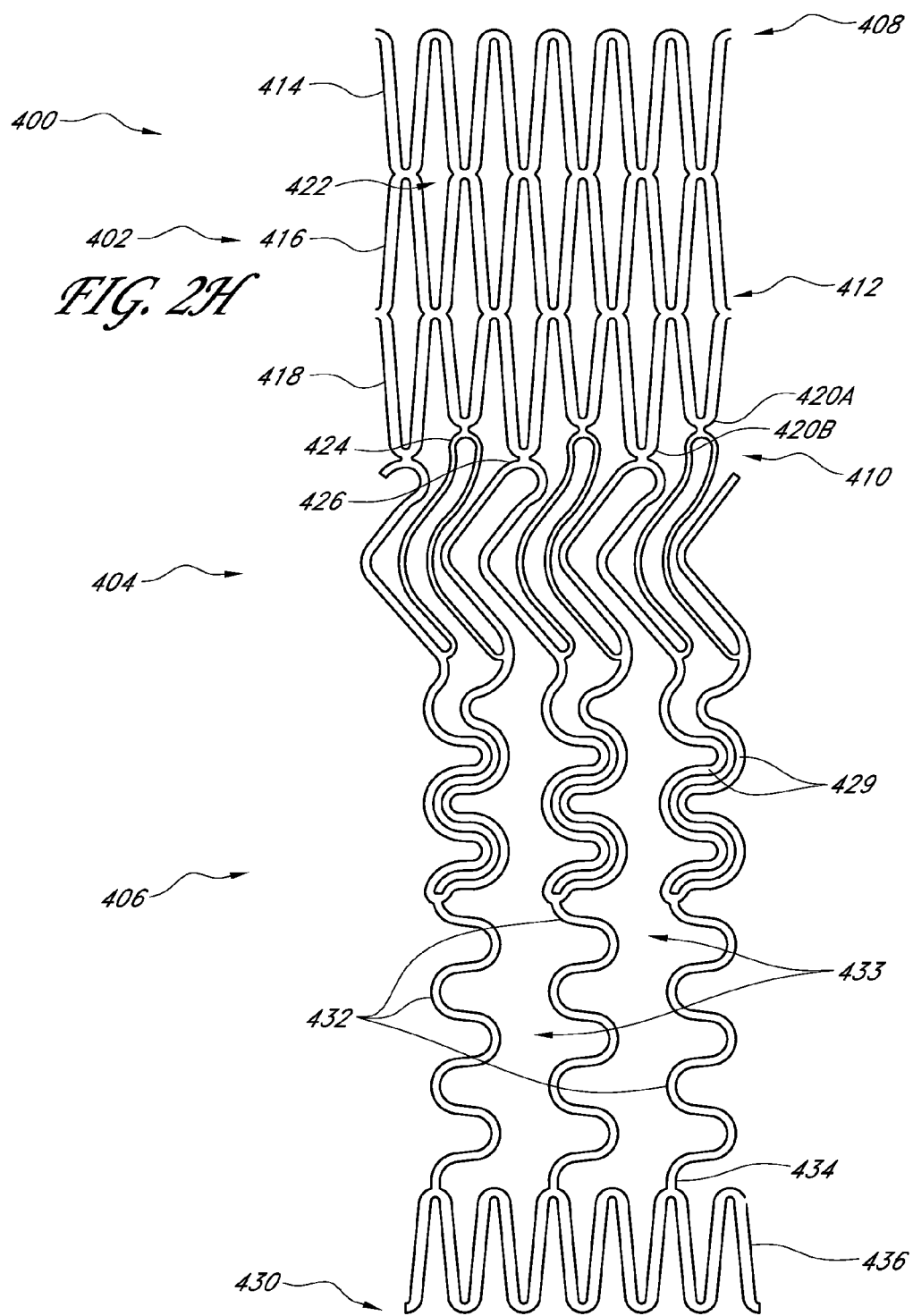
FIG. 2H is a lateral view as in FIG. 2F, with the fronds modified to enhance crossing of a secondary stent while maintaining robust scaffolding in the ostium.

FIGS. 2H-2I shows other embodiment of prostheses 400, 440 (in "rolled out" patterns) that include support or stent sections having a closed cell structure. The prostheses 400, 440 have frond sections that have been modified to enhance to performance and interaction thereof with a main vessel stent to be deployed therewith. The prostheses 400, 440 may be configured in some respects similar to those described hereinabove.

The prosthesis 400 is adapted for placement at an ostium opening from a main body lumen to a branch body lumen and, as shown in FIG. 2H, includes a stent section 402, transition section 404, and a frond section 406. The stent section 402 is generally tubular and is disposed on a distal portion of the prosthesis.

The stent section 402 comprises a distal end of 408, a proximal and 410, and a wall surface 412 extending therebetween. The wall surface 412 is formed of a plurality of circumferentially arranged undulating members 414, 416, 418. In one construction, each trough of the undulating number 414 is fixedly coupled with a corresponding crest of the undulating number 416. In one construction each trough of the undulating number 416 is fixedly coupled with corresponding crest of the undulating member 418. Although additional undulating members can be provided between the undulating number 416 and the proximal end 410 of the stent section 402, in one embodiment the undulating number 418 is coupled with the transition section 404 of the prosthesis 400. In one arrangement, the undulating number 418 includes alternating shallow and deep troughs 420A, 420B that are coupled with a distal portion of the transition section 404, as discussed below. The deep and shallow trough's 420A, 420B comprise proximal apices of the stent section 402.

Adjacent undulating members 414, 416 define closed cells 422 therebetween. The closed cells 422 are defined between distal and proximal apices. The distal apices correspond to crest of the undulating number 414. The proximal apices correspond to troughs of the undulating number 416. When expanded, lateral aspects of the closed cells 422 move apart circumferentially, such that a greater distance is defined between the central portion of the lateral members forming the circumferential sides of the cells 422. This movement produces expansion of the cells and also moves apart adjacent troughs of the undulate number 414 and adjacent crests of undulating number 416. The crests and troughs are directly coupled with one another in the embodiment of FIG. 2H. In the expanded state, the wall surface 412 comprises a plurality of substantially diamond shaped cells 422.

The stent section 402 provides a radially expansible support that is configured to be deployed in at least a portion of the branch body lumen as part of a treatment to maintain flow through the branch body lumen.

The transition section 404 can take any suitable form, but preferably is configured to support the carina or ostium at the bifurcation when deployed. The transition section 404 is similar to those hereinbefore described, e.g., in connection with FIGS. 2D-2F. In one embodiment the transition section 404 includes alternating filament sections 424, 426. The filament sections 424 are generally thinner than the filament sections 426. The filament sections 424 are configured to extend distally farther than the filament sections 426 in one embodiment. The filament sections 424 can be couple with the shallow troughs 420A and the filament sections 426 can be couple with the deep troughs 420B of the undulating number 418 in one embodiment. By configuring the undulating member 418 with shallow and deep troughs 420A, 420B, a greater amount of material can be incorporated into the transition section 404. This is because the filaments coupled with the shallow troughs 402A can be lengthened compared to an embodiment where all of the proximal apices extend to a same axial location corresponding to the location of the deep troughs 402B. By providing a greater amount of material, the transition section 404 is able to provide a greater degree of scaffolding in the area of the ostium. This enhances the ability of the prosthesis 400 to effectively maintain the ostium open after implantation.

In one embodiment, the transition section 404 has a distal section with four side-by-side filaments. In one embodiment, the distal section of the transition section 404 includes two filaments of the relatively thin filament sections 424 and two filaments of relatively thicker filaments sections 426 located on opposite sides of the filament section 424. The transition section 404 can be configured with a proximal section having only two side-by-side filaments 429. The two side-by-side filaments 429 can take any suitable form, but preferably comprise an undulating pattern. For example, the two side-by-side filaments 429 can comprise a generally sinusoidal pattern wherein the filaments are in-phase. In one embodiment, the transition portion 404 includes a dual serpentine section as shown in FIG. 2H.

The transition section 404 can be configured to optimally scaffold the anatomy at a bifurcation. For example, the proximal portion of the transition section 404 can be configured to provide sufficient support at the bifurcation for a treatment. In some applications using a second, main vessel stent deployed in conjunction with the prosthesis 400, at least a portion of the bifurcation may be supported primarily (or only) by the transition portion. Therefore, it may be desirable to increase the amount of material or stiffness of the material at the transition portion. In some embodiments, this can be achieved by maximizing the amount of coverage at the bifurcation. Also, optimal coverage of the carina may depend upon the geometry of the bifurcation. Where the angle of the branch vessel to the main vessel is high (e.g., approaching)90°, a shorter transition portion is suitable. However, when the angle of the branch vessel to the main vessel is low (e.g., 45° or less), a longer transition portion is beneficial to provide sufficient coverage at the bifurcation. A shorter transition portion is described below in connection with FIG. 2L.

The frond section 406 includes a plurality of fronds 432 that extend axially proximally of the proximal end 410 of the stent section 402. The fronds 432 extend between the transition section 404 and a proximal end 430 of the prosthesis in one embodiment. In the expanded state, the fronds 432 define lateral (circumferential) boundaries of windows 433 through which a main vessel stent can be deployed, as discussed herein. In one arrangement, each of the fronds 432 comprises a single filament that extends from the proximal section of the transition section 404 to a proximal end 434 of the fronds 432. The fronds 432 are configured to be deformably deployed in at least a portion of the main body lumen and to apply less radial force to adjacent tissue than the expanded support applies in the branch body lumen.

The length of the fronds 432 can be selected based on a number of factors. In some embodiments, the length of the fronds is a function of the size of the vessel into which the prostheses described herein are to be deployed. For example, if the prosthesis 400 is to be deployed in a small vessel and if the main vessel at which the bifurcation is formed is also small, than the windows between the fronds will be relatively small, even in the expanded state. As a result, there is a greater need for a high degree of alignment of the main vessel stent with the window 433 formed in the branch vessel stent. By providing longer windows, there can be greater assurance of proper alignment through the windows 433.

In the embodiment of FIG. 2H, a circumferential link 436 is provided that has an undulating configuration comprising a plurality of apices. The circumferential link 436 connects each of the proximal ends 434 of the fronds 432. The proximal end 434 of each frond 432 is connected to a distal apex of the circumferential link. The circumferential link 436 forms a proximal boundary of the windows 433 in one embodiment.

In one embodiment, some of the apices of the circumferential link are not connected from adjacent fronds 432. For example, in one embodiment, every other apex of the circumferential link 436 is not connected to a frond. Providing a greater number of unconnected apices on the circumferential link enables a greater amount of expansion of the circumferential link 436 while maintaining a relatively short axial zone in which the circumferential link 436 is located in the unexpanded state.

FIG. 2I shows that that the prosthesis 440 has a stent section 442 that is configured as a closed cell structure, in which a plurality of cells 444 are provided. As used herein, a closed cell structure is one in which all or substantially all of the peaks and troughs of a cell are connected to longitudinally adjacent cells.

Each of the cells 444 comprises a distal apex 446, a proximal apex 448, a first lateral deformable section 450, and a second lateral deformable section 452. In the embodiment of FIG. 2I, the distal and proximal apices 446, 448 correspond to crests and troughs of adjacent sinusoidal members 454, 456. The sinusoidal members 454, 456 extend circumferentially around the stent 440 in a formed (e.g., a tubular) configuration and are spaced apart along the length of the prosthesis 440 by the deformable sections 450, 452. The deformable sections 450, 452 can take any suitable form, but preferably are more flexible than the sinusoidal members 454, 456 such that the sections 450, 452 can deform upon application of a bending load (e.g., applied at the ends of stent section 442). This arrangement increases the flexibility of the stent section 442 for delivery and conformance to tortuous vasculature. The sections 450, 452 also enable the stent to lengthen somewhat such that adjacent sinusoidal members 454, 456 can move closer to each other or farther apart to accommodate curvature of the anatomy, for example.

In the illustrated embodiment, a distal end 460 of the deformable section 450 connects to a trough 462 of a distal sinusoidal member 454 and a proximal end 464 of the deformable section 450 connects to a crest 466 of a proximal sinusoidal member 456. Across the cell 444, a distal end of the deformable section 452 connects to a trough of the distal sinusoidal member 454 and a proximal end of the deformable section 452 connects to a crest of the proximal sinusoidal member 456. In one embodiment, each of the distal ends of the deformable sections 450, 452 is coupled with corresponding troughs of the sinusoidal member 454 at a location latterly offset from the center of the troughs. In one embodiment, each of the proximal ends of the deformable sections 450, 452 is coupled with corresponding crest of the sinusoidal member 456 at a location latterly offset from the center of the crests. In one embodiment, the crests and troughs of adjacent sinusoidal members 454, 456 are circumferentially aligned, and the deformable sections 450, 452 are connected on opposite sides of the centerline $C_L$ of the aligned crests and troughs 462, 466.

The deformable sections 450, 452 can take any suitable form. For example, the deformable sections 450, 452 can be generally N-shaped. Various embodiments, the deformable sections 450, 452 can comprise at least one, e.g., two, generally circumferentially oriented undulations. The generally circumferentially oriented undulations are configured to become at least partially straightened during expansion of the stent section 442 such that the adjacent sinusoidal members 454, 456 can have a different separation distance therebetween in an expanded state compared to a non-expanded state. Also, the undulations permit corresponding side of the adjacent sinusoidal members 454, 456 to move toward each other while opposite corresponding side of the adjacent sinusoidal members 472, 456 move away from each other. This feature can enable the stent section 442 to flexibly obtain an appropriate shape upon expansion based upon the anatomy of the patient.

The prosthesis 440 has a transition section 470 that can be similar to those hereinbefore described. In the embodiment of FIG. 2I, a plurality of filaments is provided that are coupled with a proximal most sinusoidal member 472. The sinusoidal member 472 can be similar to the sinusoidal members 454, 456 or it can be modified to couple with the filaments in the transition section 470. In one modification, the sinusoidal member 472 comprises alternating deep troughs 474 and shallow troughs 476. In one embodiment, every other trough is a deep trough 474 and every other trough is in shallow trough 476. In one embodiment a plurality of fronds 478 extend proximally within the transition section 470 from the proximal most sinusoidal member 472. The transition section 470 is otherwise similar to those hereinbefore described.

In one embodiment, each of the fronds 478 has a greater number of filaments within the transition zone 470 than it does proximal thereof. For example, the construction of the transition zone 470 and the fronds 476 can be similar to that of FIG. 2H. In one embodiment, it may be desirable to interconnect adjacent dual serpentine portion of the transition portion distal of the fronds 478. For example one or more connectors 480 can be provided between parallel undulating filaments or filamentous portions of a frond 478. In one arrangement the connector 480 prevents the frond 478 for being overly floppy and prone to undesirable deformation.

FIGS. 2J and 2K illustrate various embodiments of prostheses in which an open cell configuration is provided in a stent section. In one aspect and open cell configuration provides a plurality of undulating members that are circumferentially oriented and space apart along the length of the prosthesis. In the open cell configuration at least some of the peaks of the undulating members are not directly connected to other undulating members.

FIG. 2J illustrates a first in a prosthesis 500 with an open cell configuration that is adapted for placement at an ostium opening from a main body lumen to a branch body lumen and. The prosthesis 500 includes a stent section 502, a transition section 504, and a frond section 506. The stent section 502 is generally tubular when formed and is disposed on a distal portion of the prosthesis 500.

The stent section 502 comprises a distal end 508, a proximal end 510, and a wall surface 512 extending therebetween. The wall surface 512 is formed of a plurality of circumferentially arranged undulating members 514, 516, 518, 520, 521. In one construction, the undulating number 514 is only periodically connected with the adjacent undulating member 516 by a connector 522. For example, the undulating number 514 can include a repeating pattern of two unconnected proximally oriented troughs 524 followed by a connected peak 526.

They connected peak 526 of the undulating member 514 can be connected to a peak of to the adjacent undulating number 516 by the connector 522. In one embodiment the connected peak 526 forms a proximally-facing bight within which the connector 522 extends. The distal end 530 of the connector 522 connects to the inside portion of the bight. A proximal end 532 of the connector 522 connects with a peak of the adjacent undulating number 516. The connector 522 can take any suitable form, but preferably includes at least one circumferentially oriented undulation 534 that permits relative axial movement of the undulating members 514, 516. The connector 522 enables the stent section 502 to elongate between one or more of the circumferentially arranged undulating members 514, 516, 518, 520, 521.

Undulating members 516, 518, 520 are disposed internally within the structure of this stent section 502. These undulating members 516, 518, 520 are within the structure in that they are not located at the proximal or distal end of the stent section 502. In other embodiments, there can be more internally disposed undulating members or these members can be eliminated entirely. The internally disposed undulating members 516, 518, 520 are coupled with adjacent undulating members along their distal ends at internal bight locations, as describe above, and also at external peak locations. For example, a connector 522 connects the undulating members 518, 520 from a location within a proximally facing bight of the undulating member 518 to a distal aspect 519 of a peak of the undulating member 520.

FIG. 2J shows that two proximal peaks of the undulating member 518 are disposed between the connector 522 and an adjacent connector 522 and that these proximal peaks are not connected to distal aspects of the undulating member 520. These unconnected peaks provide flexibility such that the stent can be delivered more easily and can better conform to the vasculature, compared to a closed cell structure. A distal peak of the undulating member 518 is connected by a connector 522 to a proximally oriented bight of the undulating member 516.

The undulating member 521 is located at the proximal end of the stent section 502. The undulating number 521 is coupled with the adjacent undulating number 520 along the distal portion of the undulating number 521 at every other peak (as is true of all undulating members except the distal-most in this embodiment). In particular, connectors 522 extend distally from distal peaks 536 of the undulating member 521. FIG. 2J shows that in some embodiments, the proximal end 510 of the stent section 502 includes distal peaks which are free of connection to adjacent structures. In particular, the peaks 526' are disposed between the distal peaks 536 and have proximally facing bights that are free from connectors.

The transition section 504 connects to the stent section 502 in a manner similar to those hereinbefore described. Each proximally oriented peak 538 of the undulating member 521 is coupled with a filament section. Filament section 540 comprises two relatively thin filaments that extend distally to and connect with every other peak of the undulating number 521. Filament section 542 comprises relatively thick filaments that extend distally to a location that is proximal of a location where the filament section 542 couples with the stent section 502. In one embodiment a generally axially oriented connector 544 extends between the proximal end of every other peak 538 of the undulating number 521 and the distal-most aspect of the filament section 542.

The transition section 504 and the frond section 506 are similar to those described in connection with FIG. 2H. The frond section 506 can include a plurality of serpentine shaped fronds that are coupled with a circumferential link. These fronds form windows, as discussed above, for delivery of a main vessel stent in some techniques.

FIG. 2K illustrates another embodiment of a prosthesis 580 that is similar to the prosthesis 500. The prosthesis 580 includes a stent section 582, a transition section 584, and a frond section 586. The stent section 582 comprises a distal end 588, proximal end 590, and a wall surface 592 extending therebetween.

The wall surface 592 includes a plurality of adjacent circumferential bands 594 that share one or more members 596 in common. One or more peaks 598 of one circumferential band 594 are longer than the other peaks 600. In some embodiments, one or more troughs 602 of the adjacent circumferential band 594 are longer than the remaining troughs 604. In one embodiment, both the peaks 598 and the troughs 602 are longer than the peaks 600 and troughs 604. The longer peaks 598 intersect with the longer troughs 602 in one embodiment and share a member 596 in common forming an X-shaped structure 608.

The resulting X-shaped structure 608 in the embodiment of FIG. 2K can have one or more orientations in various embodiments. For example, in a distal-most circumferential band, the X-shaped structure 608 can be inclined toward in a first circumferential direction such that a distal portion of the X-shaped structure 608 is to the right of a distal projection of the proximal portion of the X-shaped structure. In one embodiment, the second-most distal circumferential band has an X-shaped structure 608' that is inclined in a second circumferential direction opposite of the first circumferential direction such that a distal portion of the X-shaped structure 608' is to the left of a distal projection of the proximal portion of the X-shaped structure. In one embodiment, every other circumferential band has X-shaped portions that are inclined in opposite directions. In one embodiment, each circumferential band has an X-shaped portion that is a mirror image of the X-shaped portions disposed on one or more immediately adjacent bands.

In the embodiment of FIG. 2K, there are three overlapping regions 610 between adjacent circumferential bands 594. The distal end of each cell 612 comprises two peaks 600 and two troughs 604 and the proximal end of each cell 612 is defined by two peaks 600 and two troughs 604. There can be fewer or more overlapping regions 610 between adjacent circumferential bands 594. The X-shaped structures 608, 608' extend in oblique directions relative to the longitudinal axis of the stent section.

In one embodiment, the distal-most circumferential band 594 comprises distal peaks 600 and the proximal-most circumferential band 594 comprises proximal troughs 604. The filament sections 614 comprise relatively thin filaments and filament sections 616 comprise relatively thick filaments. The transition section 584 is similar to that of FIGS. 2H-2J except that the filament sections 614, 616 connect to alternating troughs of the proximal-most band 594 of the stent section 582 at substantially the same longitudinal position, e.g., at the proximal end 590 of the stent section 582.

The frond section 586 can be similar to those hereinbefore described, e.g., including a serpentine member that is coupled with a circumferential link.

FIG. 2L illustrates a prosthesis 640 having a stent section 642, a transition section 644, and frond section 646. The stent section 642 includes a distal end 648, a proximal end 650, and a wall pattern 652 extending therebetween. The wall pattern 652 is similar to that discussed above in connection with the stent section 402 of FIG. 2H and will not be described further here. Additionally, any of the stent sections or wall patterns described elsewhere in this application can be substituted for the stent section 642 in various embodiments.

The transition section 644 and frond section 646 are similar to those discussed above in connection with FIG. 2H. The transition section 644 includes a pair of relatively thin members 654 coupled with a proximal portion of the stent section 642 alternating with a pair of relatively thick members 656. Each frond extends proximally from the stent section 642. The prosthesis 640 transitions in the transition section 644 from four generally side-by-side filaments to two generally side-by-side filaments. The prosthesis 640 further transitions from two generally side-by-side filaments to a plurality of single filament fronds, which extend proximally to a circumferential link 658.

In one embodiment, the transition portion 644 comprises two generally side-by-side filaments that are relatively short. For example, the proximal portion of the transition portion 644 having two generally side-by-side filaments can be configured such that the two filaments include only one circumferential undulation 660. The single filament fronds are substantially longer than the side-by-side (e.g., dual serpentine) portion. In one embodiment the single filament fronds are about three times as long as the side-by-side portion of the transition portion 644.

Making the side-by-side (e.g., dual serpentine) portion relatively short is beneficial for branch vessels that are at or approaching 90° from the main vessel. In comparison, in connection with FIG. 2H, the portion of the frond 432 comprising to side-by-side filaments is much longer. In this embodiment, the single filament portion is about the same length as the portion of the frond comprising to side-by-side filaments. As discussed above, the prosthesis of FIG. 2H is optimized for low take-off angle bifurcations.

Figure 2M:
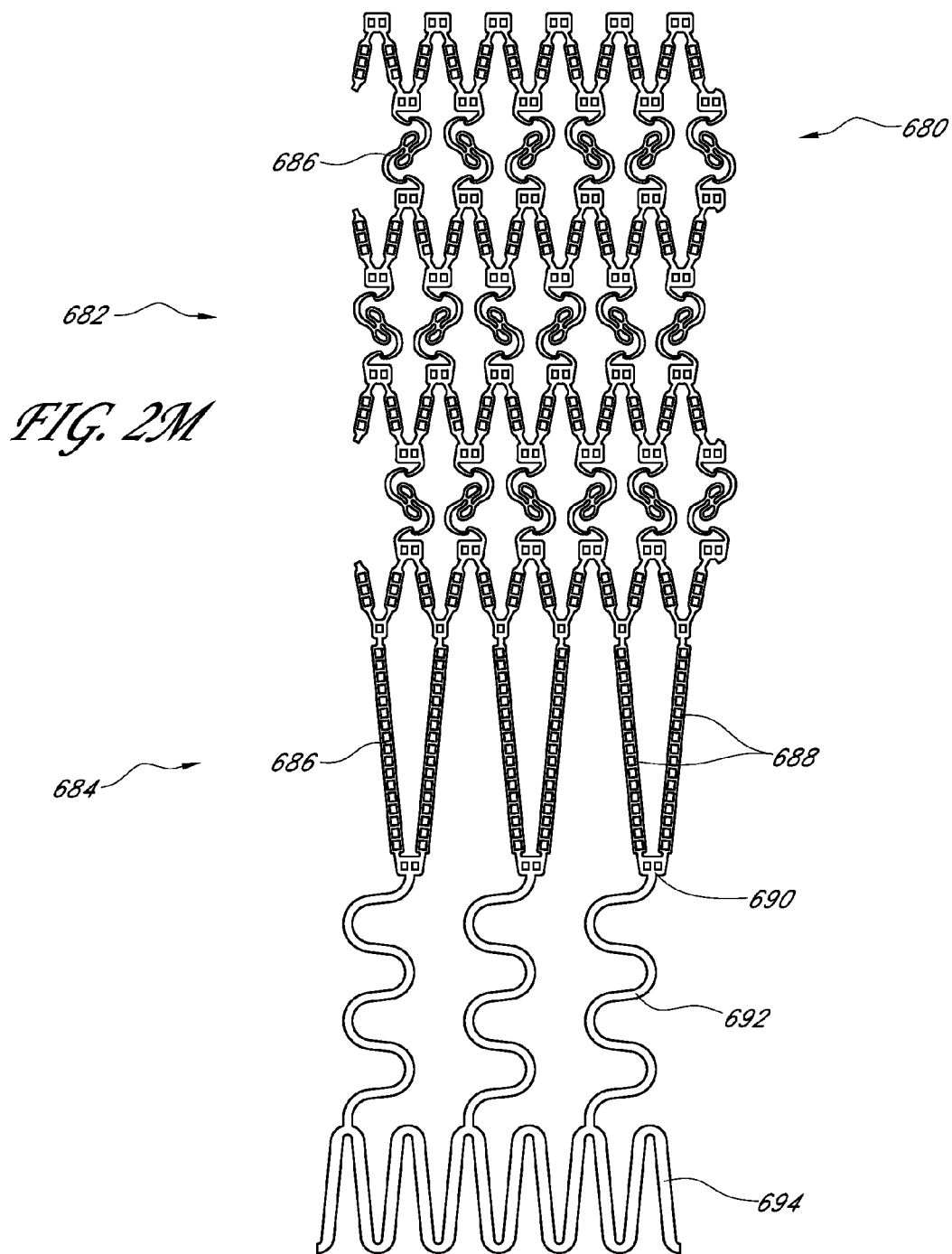
FIG. 2M shows a lateral view of another embodiment of a stent having fronds in a rolled out configuration, wherein reservoirs are provided for holding a drug to be eluted into the vasculature.

FIG. 2M illustrates a prosthesis 680 that is a modification of the prosthesis of FIG. 2I. In embodiment of FIG. 2M, the members defining the stent section 682 and the transition section 684 have been modified to include drug containing portions 686. In this embodiment, the members have been formed in a substantially flattened configuration. The drug containing portions 686 can take any suitable form, such as being well-shaped such that a drug can be deposited therein.

Additionally, the transition section 684 has been modified compared to that shown in FIG. 2I to include a plurality of substantially straight members 688 extending proximally from a proximal end of the stent section 682. The substantially straight members 688 comprised drug containing portions 686. In one embodiment, the drug containing portions 686 are formed by laser cutting depressions or through-holes in the structure of the stent section 682 or the members 688. Also, the substantially straight members 688 can take any suitable form. In the illustrated embodiment, the members 688 are angled proximally toward each other such that they can be joined by a short circumferential extending member 690. Drug containing portions 686 can also be formed on the circumferentially extending member 690.

A plurality of single undulating filament fronds 692 extends proximally from the circumferentially extending members 690 a circumferential link 694 located at the proximal end of the prosthesis 680. In another embodiment, the single filament fronds 692 are configured to be loaded with a drug for any suitable drug treatment, e.g., by including drug containing portions 686.

In some treatment techniques, portions of the prosthesis 680 that are deployed in the main vessel are configured not to have a drug eluting portion. For example, it may be advantageous to deploy the prosthesis 680 with a main vessel stent that has a drug eluting portion and for the main vessel portion of the prosthesis not to have a drug eluting portion. This can minimize interactions between drugs on the main vessel stent and any drugs that may be provided on the stent section 682, for example, to better control the treatment provided in the main and branch vessels.

In some embodiments, the single filament section 692 can be configured to be loaded with a drug such that the drug can be eluted into a main vessel or main passageway when the prosthesis 680 is deployed. In other embodiments, the circumferential link 694 can be configured to be loaded with a drug such that the drug can be eluted into a main vessel or main passageway when the prosthesis 680 is deployed. In other embodiments, the single filament section 692 and the circumferential link 694 can be configured to be loaded with a drug such that the drug can be eluted into a main vessel or main passageway when the prosthesis 680 is deployed. Any suitable technique can be used to load a drug in the single filament section 692 and/or in the circumferential link 694. For example, these portions can be provided with well-shaped portions as discussed above. Embodiments where the single filament section 692 and/or the circumferential link 694 are coated can be used, for example, with a main vessel stent that is not drug eluting.

FIGS. 2N-2O show another embodiment of a wall pattern for a prosthesis 700, in a "rolled-out" format. The prosthesis 700 includes a stent section 704, a transition section 708, a frond section 712, and a link system 714. The prosthesis 700 has similar features to some of the embodiments set forth above, for example, incorporating a similar transition section and a similar frond section to those described above. For example, the prosthesis 700 is not limited to the particular pattern of the stent section 704 illustrated in FIG. 2N-2O, but can have any other pattern including any of the patterns described herein or conventional designs. The link system 714 is configured to enhance the securement of the prosthesis 700 to a deployment device, as discussed in greater detail below.

The stent section 704 serves to hold open a vascular region, e.g., a branch vessel distal a bifurcation, after being deployed. The stent section 704 can be formed from an elongated tubular member such that undulating components of radially expandable cylindrical elements 716 thereof can be relatively flat in transverse cross-section. As such, when the stent section 704 is expanded, the cylindrical elements 716 are pressed into the wall of a vessel and as a result do not interfere with the blood flow through the vessel. The cylindrical elements 716 of stent section 704, which are pressed into the wall of the vessel, may in some cases be covered with endothelial cell growth which may further minimize blood flow interference.

Undulating portions of the cylindrical sections 716 provide secure engagement with an inner surface of the vessel to prevent stent movement within the vessel. Furthermore, the cylindrical elements 716 are closely spaced at regular intervals to provide uniform support for the wall of the vessel. The stent section 704 thus is well adapted to hold in place small flaps or dissections in the wall of the vessel.

FIGS. 2N-2O illustrate that the stent portion 704 includes interconnecting elements 720 disposed between adjacent cylindrical elements 716. The interconnecting elements 720 on both sides of a cylindrical element 716 can be placed to enhance the flexibility for the stent portion 704. In the embodiment shown in FIGS. 2N-2O, the stent portion 704 has four interconnecting elements 720, with a single element 720 being located between adjacent cylindrical elements 716. The interconnecting elements 720 are positioned to be more than one complete undulation apart. In one embodiment, the interconnecting elements 720 are spaced apart by approximately 90 degrees about the circumference of the stent portion 704. The alternation of the interconnecting elements 720 results in a stent that is longitudinally flexible in all directions. Various configurations for the placement of interconnecting elements are possible, and several examples are illustrated schematically in U.S. Pat. No. 5,603,721, which is hereby incorporated by reference herein in its entirety.

In various embodiments, the interconnecting elements 720 can be secured to the cylindrical elements 716 in any suitable manner. For example, the interconnecting elements 720 can be coupled with the peaks or valleys of the cylindrical elements 716. The arrangement of the interconnecting elements can be used to tailor shortening of the stent during the expansion thereof.

The properties of the stent portion 704 may also be varied by alteration of the undulating pattern of the cylindrical elements 716. FIGS. 2N-2O illustrate an example stent structure in which the cylindrical elements are in serpentine patterns but out of phase with adjacent cylindrical elements. The particular pattern and how many undulations per unit of length around the circumference of the cylindrical element 716, or the amplitude of the undulations, are optimized for different aspects of performance, such as radial stiffness or other mechanical requirements, optimal scaffolding, or other characteristics.

The link system 714 is configured to provide a secure connection between a proximal portion of the prosthesis 700 and a delivery device, which can be a balloon as described below in connection with FIGS. 28 and 29. The link system 714 preferably includes a frond engagement portion 744 located adjacent to a proximal end 748 of the frond section 712 and a catheter securement portion 752. Preferably the link system 714 is configured to at least partially isolate the frond engagement portion 744 from the catheter securement portion 752. For example, as discussed below in connection with FIGS. 28 and 29, the frond section 712 can transmit a significant amount of torque to the link system 714 during advancement and deployment. The frond engagement portion 744 can absorb such a torque and prevent significant disruption of the catheter securement portion 752.

In one embodiment, the frond engagement portion 744 comprises an undulating circumferentially expandable structure 756. The circumferentially expandable structure 756 can be configured similar to the circumferential links hereinbefore described. In one embodiment, the circumferentially expandable structure 756 includes a plurality of peaks and valleys that are axially arranged, with alternating peaks being coupled with the proximal ends 748 of each frond section 712.

The catheter securement portion 752 can take any suitable form, but preferably is a circumferentially extending structure 760. The catheter securement portion 752 can be configured to surround a space that can be occupied by a portion of a catheter, such as a balloon or other expansion device that can be used to expand the prosthesis 700 from a low-profile state for delivery to an expanded state. FIGS. 2N-2O illustrate that the catheter securement portion 752 can include a circumferentially expandable structure 760 that has an undulating configuration. The circumferentially expandable structure 760 can have a generally sinusoidal pattern that is out-of-phase with a generally sinusoidal pattern of the circumferentially expandable structure 760.

The link system 714 can include an axial coupling 764 disposed between the frond engagement portion 744 and the catheter securement portion 752. The axial coupling 764 can take any suitable form, but preferably provides sufficient connection between the frond engagement portion 744 and the catheter securement portion 752 to resist premature expansion of a proximal portion of the frond engagement portion 744 from a low profile configuration. The frond engagement portion 744 has sufficient flexibility to absorb torque from the frond section 712 while at the same time isolating distal portions of the catheter securement portion 752 from such torque. Thus, the link system 714 is well adapted to prevent fronds in the frond section 712 from divaricating from a delivery device, such as a balloon catheter.

In one embodiment, the axial coupling 764 includes at least one but preferably a plurality of axially extending connectors. In the illustrated embodiment, each of the connectors connects a peak 768 of the catheter securement portion 752 with a valley 772 of the frond engagement portion 744. The coupling 764 can be a generally straight member or can have one or more undulations that can be provided to enhance the mechanical isolation of the frond engagement portion 744 and the catheter securement portion 752.

FIG. 2O illustrates the transition of various structures of the prosthesis 700 from a collapsed state corresponding to FIG. 2N to an expanded state FIG. 2O. The frond section 712 includes a plurality of side-by-side filaments 780 that extend proximally from the transition section 708. Preferably the side-by-side filaments 780 extend through a plurality of axially oriented undulations within a distal portion of the frond section 712 to a central portion of the frond section 712. From the low profile state of FIG. 2N to the expanded state of FIG. 2O, the side-by-side filaments 780 open up to a generally V-shaped configuration. For example, distal portions of the side-by-side filaments 780 become spaced apart by a greater amount in the expanded state than in the unexpanded state. Also, the spacing of the side-by-side filaments 780 is altered upon expansion from being generally constant between the transition section 708 and the central portion of the frond section 712 to being distally increasing in expanded states. FIG. 2O shows that the increase in spacing between adjacent filaments of the side-by-side filaments 780 need not be continuously increasing along the entire length of the frond section 712. A greater spacing can be provided at a forward location 784 adjacent to the transition section 708 compared to a central portion 788 of the frond section 712.

FIG. 2P illustrates another embodiment of a prosthesis 800 that is modified to provide for improved trackability within vessels. The prosthesis 800 is similar to those hereinbefore described, for example having a stent section 804, a transition section 808, and a link system 814 similar to those of FIG. 2N-2O. The prosthesis 800 has a frond section 812 that is modified to minimize adverse interactions within the vasculature when the prosthesis 800 is moved therein.

The frond section 812 includes a distal portion 822 and a proximal portion 826. The distal portion 822 is similar to the distal portion of the frond section 712, including a plurality of side-by-side members extending between the transition section 808 and a central portion 830 of the frond section 812. The proximal portion 826 is configured to provide a larger angle of approach to structures disposed within vasculature to reduce the effect of impact therebetween. For example, in one embodiment, the proximal portion 826 includes a single filament portion 834 that extends from the central portion 830 to the link system 814. The single filament portion 834 can have an undulating configuration in some embodiments. The undulations can be elongated to reduce the greatest angle of approach between distal facing edges 838 of the filament and vascular structures that may be located distal of the prostheses 800 as it is being advanced. For example, the single filament portion 834 preferably is arranged to minimize an angle relative to a longitudinal axis of the prosthesis 800. In one embodiment, the single filament portion 834 preferably is arranged have an angle of approach that does not exceed 45 degrees relative to a longitudinal axis of the prosthesis 800. In one embodiment, the single filament portion 834 preferably is arranged have an angle of approach is less than about 35 degrees relative to a longitudinal axis of the prosthesis 800. In one embodiment, the single filament portion 834 preferably is arranged have an angle of approach is about 20 degrees or less. In one embodiment, the single filament portion 834 preferably is arranged have an angle of approach is less between about 5 degrees and about 20 degrees relative to a longitudinal axis of the prosthesis 800. In one embodiment, the single filament portion 834 has a substantially straight configuration.

Any of the prosthesis described herein, including those described in connection with FIGS. 2H-2P, can be configured as bioerodable structures. In certain embodiments, bioerodable structures are structures that are absorbed into the body and eventually disappear, but which maintain structural integrity during substantially the entire life of the structure. In other embodiments, any of the prosthesis described herein, including those described in connection with FIGS. 2H-2P, can be configured as biodegradable structures. In certain embodiments, biodegradable structures are structures that are absorbed into the body and eventually disappear, but that also lose a substantial amount of their structural integrity more rapidly than a bioerodable structure. In general terms, the prosthesis 50 may be considered to be a tubular structure which comprises a plurality of axially extending fronds having a first radially expandable structure on a first end and a second radially expandable structure on a second end. The first radially expandable structure is a support structure 52 such as a stent, as has been described for positioning within the branch vessel. The second radially expandable structure comprises the circumferential link 120.

Typically, the circumferential link 120 will provide significantly less radial force than the first support structure 52, in view of its primary function to maintain the spacing and orientation of the fronds rather than providing support to the vessel wall. In a typical embodiment, the support structure 52 will have a first radial force, the circumferential link 120 will have a second, lesser radial force, and the fronds will contribute nothing or essentially nothing to the radial force of the structure. Alternatively, the circumferential link 120 may have a radial force which is approximately equal to the radial force of the support structure 52, and possibly even in excess of the radial force of the support structure 52, depending upon the desired clinical performance. The fronds may exhibit a radial force, which may be due mostly or entirely to the adjacent stent or circumferential link.

In an implementation of the invention intended for use in the coronary arteries, the stent portion may have a crush resistance or radial strength on the order of at least about 10 psi or 12 psi, and, often at least about 14 or 15 psi. The circumferential link may have a radial force or crush resistance of no greater than about 90%, often no greater than about 50%, and in some embodiments no greater than about 25% of the radial force or crush resistance of the branch vessel stent. Thus, in a prosthesis having a stent with a crush resistance of at least about 14 or 15 psi, the circumferential link might have a crush resistance of less than about 4 or 3 psi. The crush resistance in the fronds may be less than about 2 psi or less than about 1 psi, depending upon the length of the fronds, structure of the fronds, crush resistance of the adjacent structures, and other factors that may affect the cantilevered transfer of radial force from the adjacent stent or circumferential link.

Radial strength or crush resistance as used herein, may be determined in psi by constructing a radial strength test fixture. In general, the radial strength test fixture comprises a pressured chamber, adapted to allow the insertion of a flexible tube which can be sealed at each end to the walls of the chamber such that the exterior wall of the tubing is exposed to the pressure generated in the chamber while the central lumen of the tube is exposed to ambient atmospheric pressure. Any of a variety of thin walled flexible tubing may be utilized, such as a thin walled latex tubing, such that the inside diameter of the latex tubing may be approximately 10% less than the nominal expanded diameter of the stent. The stent is expanded within the tubing, such as by inflating an associated dilation balloon to its rated burst pressure or other pressure sufficient to expand the stent to its intended implanted diameter. The balloon may be deflated and the balloon catheter withdrawn. The tubing is mounted in the pressure chamber as described above. Air or other inflation media may be pumped into the pressure chamber to slowly increase the pressure within the chamber (for example at a rate of about 1 psi per second). Once any portion of the central lumen through the prosthesis has been reduced under pressure to less than or equal to 50% of its original lumen diameter, the pressure in the chamber is noted and considered to be the radial force or crush resistance of the prosthesis.

The second radially expandable structure (circumferential link) may also have a shorter axial length than the first radially expandable structure (stent). For example, in a coronary artery embodiment, the axial length of the stent may be at least 300% or 500% or more of the length of the circumferential link.

The fronds will have a length in the axial direction between the support 52 and the circumferential link 120 of generally in excess of about 2.5 mm or 3 mm, and in certain embodiments in excess of about 5 mm. At least some or all of the fronds may have a length in excess of about 8 mm, and, in one implementation of the invention intended for the coronary artery, the frond length is in the vicinity of about 9.4 mm.

The circumferential link may also have a smaller strut profile compared to the strut profile in the support 52. For example, the cross sectional dimensions of a strut in the support 52 and/or the fronds may be on the order of about 0.003 inches by about 0.055 inches in an embodiment intended for coronary artery applications. In the same embodiment, the cross sectional dimensions through a strut in the circumferential link may be on the order of about 0.001 inches by about 0.003 inches.

The frond length may also be evaluated relative to the main lumen diameter. For example, in the coronary artery environment, diameters in the range of from about 2 mm to about 5 mm are often encountered. Frond lengths of at least about equal to the main vessel diameter (e.g. at least about 2 mm or 3 mm or 4 mm or greater) are contemplated. Fronds lengths of as much as 2 times or 3 times or 4 times or more of the diameter of the associated main vessel are also contemplated.

Figure 14A:
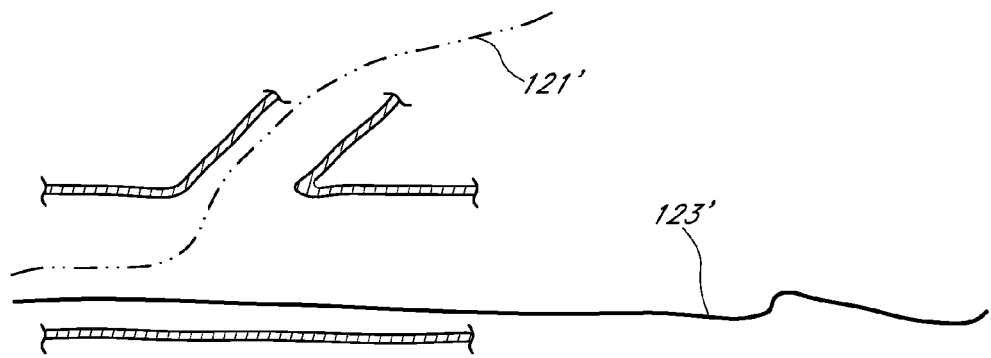
FIGS. 14A-14E are a sequence of schematic illustrations showing the deployment of a vascular bifurcation prosthesis with linked fronds.
Figure 14B:
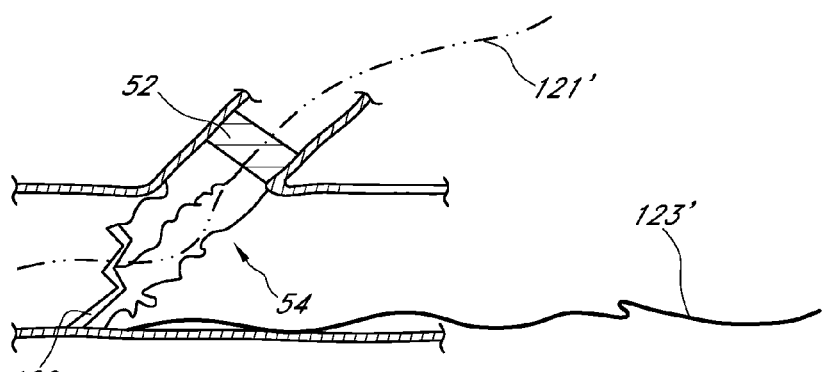

Deployment of the bifurcation prosthesis with linked fronds may be understood by reference to FIGS. 14A-14E. In FIG. 14A, the side branch guidewire 121' has been positioned in the side branch and the main vessel guidewire 123' has been positioned in the main vessel. The side branch stent is next deployed in the side branch, with the fronds extending across the ostium and into the main vessel. The circumferential link 120 may either self expand or be balloon expandable to provide a main vessel stent opening. See FIG. 14B.

Figure 14C:
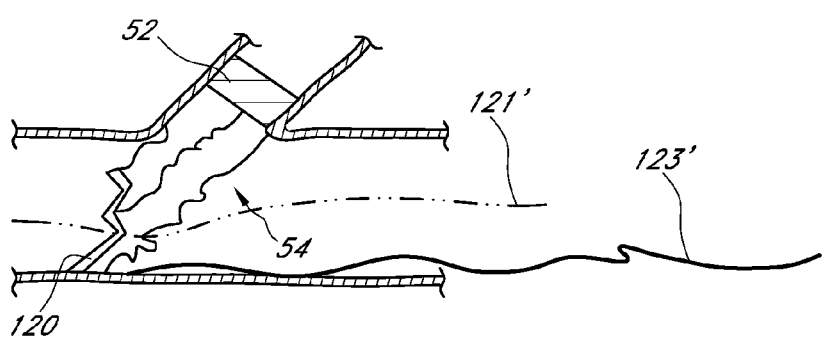

Referring to FIG. 14C, the side branch wire is retracted from the side branch and advanced between the fronds into the main vessel. The main vessel wire 123 may be retracted at this point in the procedure. The main vessel stent is then advanced over the wire through the opening formed by the circumferential link, and through a space between adjacent fronds into the desired position.

Figure 14D:
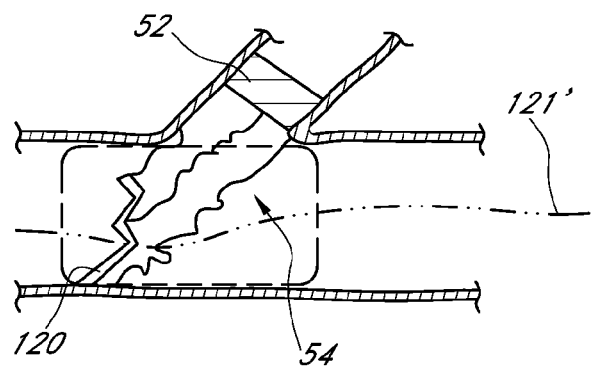
Figure 14E:
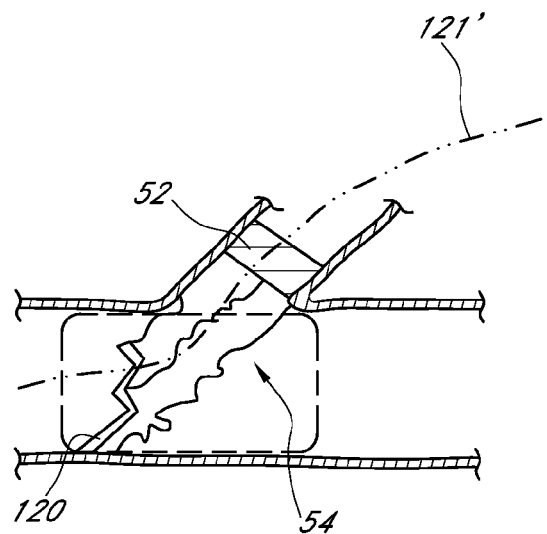

Referring to FIG. 14D, the main vessel stent is deployed to entrap the fronds against the vessel wall. The circumferential link is additionally trapped against the vessel wall. Post dilation to open the side wall opening into the branch vessel may optionally be accomplished, by retracting the side branch wire and readvancing it into the side branch. See FIG. 14E.

Based upon the foregoing description, it will be apparent to those of skill in the art that the prosthesis of the present invention may be implanted in a variety of alternative manners. For example, the first support structure (described above as a side branch stent) may be positioned in the main vessel, distally (from the perspective of the delivery catheter) of the bifurcation with the fronds extending proximally across the opening to the side branch. The second support structure (referred to above as a circumferential link), if present, is positioned in the main vessel proximally of the side branch opening. A standard stent may then be positioned such that the distal end of the stent is within the side branch, and a proximal end of the stent is within the main vessel, such as within the circumferential link.

Referring now to FIGS. 3A-8, in various embodiments prosthesis/delivery system 205 can include a prosthesis with stent 210 and fronds 220 which are configured to be captured or otherwise radially constrained by the delivery system during advancement of the stent through the vasculature or other body lumen. As shown in FIGS. 3A-3B, fronds 220 can be separated by axial gaps or splits 230 along the length of the frond structure. Splits 230 can have a variety of widths and in various embodiments, can have a width between 0.05 to 2 times the width of the fronds, with specific embodiments of no more than about 0.05, 0.25, 0.5, 1 and 2 times the width of the fronds. Fronds 220 can be configured to have sufficient flexibility to be advanced while in a captured mode through curved and/or tortuous vessels to reach the more distal portions of the vasculature such as distal portion of the coronary vasculature. This can be achieved through the selection of dimensions and/or material properties (e.g. flexural properties) of the fronds. For example, all or a portion of fronds 220 can comprise a resilient metal (e.g., stainless steel) or a superelastic material known in the art. Examples of suitable superelastic materials include various nickel titanium alloys known in the art such as Nitinol™.

Any of a variety of modifications or features may be provided on the fronds, to enhance flexibility or rotatability in one or more planes. For example, fronds may be provided with a reduced thickness throughout their length, compared to the thickness of the corresponding stent. The thickness of the frond may be tapered from relatively thicker at the distal (attachment) end to the proximal free end. Fronds may be provided with one or more grooves or recesses, or a plurality of wells or apertures, to affect flexibility. The specific configuration of any such flexibility modifying characteristic can be optimized through routine experimentation by those of skill in the art in view of the present disclosure, taking into account the desired clinical performance.

It is desirable to have the fronds captured and held against the delivery catheter or otherwise restrained as the stent is advanced through the vasculature in order to prevent the fronds from divaricating or separating from the prosthesis delivery system prosthesis. Capture of the fronds and prevention of divarication can be achieved through a variety of means. For example, in various embodiments the capture means can be configured to prevent divarication by imparting sufficient hoop strength to the fronds, or a structure including the fronds, to prevent the fronds from separating and branching from the deployment balloon as the balloon catheter is advanced through the vasculature including tortuous vasculature. In theses embodiments, the capture means is also configured to allow the fronds to have sufficient flexibility to be advanced through the vasculature as described above.

In an embodiment shown in FIGS. 3A-4B, the fronds can be captured under the flaps 242 of a deployment balloon 241 of a delivery balloon catheter 240. In this and related embodiments, the balloon 241 and stent 210 can be configured such that flaps 242 are substantially matched up or aligned with splits 230. This can be achieved using alignment techniques known in the art (e.g., use of alignment fixtures) when the stent 220 is positioned over balloon 241. The flap material will initially extend or protruded through the splits, but is then folded over onto one or more fronds 220 to capture those fronds. In an embodiment, this can be achieved by partially inflated and then deflated the balloon, with folding done after the inflation or deflation. Folding can be done by hand or using a capture tube or overlying sleeve known in the art. Also in an embodiment, folding can be facilitated by the use of one or more preformed folds 243, also known as fold lines 243. Folds 243 can be formed using medical balloon fabrication methods known in the art such as mold blowing methods known in the art. In an embodiment using folds 243, folding can be achieved by inflating the balloon with the overlying fronds in place, so as to have the balloon flaps 242 protrude through splits 230, then the balloon is deflated to have flaps 242 fold back over fronds 220 at fold lines 243.

Once stent 210 is properly positioned at the target vessel site, balloon 241 is at least partially inflated which unfurls flaps 242 covering fronds 220 so as to release the fronds. Once released, deployment balloon 241 can also be used to expand or otherwise deform the fronds 220 to deploy them in the selected vessel as is described herein. Alternatively, a second balloon can be used to expand and deploy the fronds as is also described herein.

To avoid pinching the balloon material of balloon 241 between layers of stent metal during the stent crimping process in one embodiment, fronds 220 can be configured such that they do not overlap when crimped down to a smaller diameter. This can be achieved by configuring the fronds to be sufficiently narrow so that crimping the stent to a smaller diameter does not cause them to overlap, or through the use of a crimping fixture or mandrel known in the art. In various embodiments, fronds 220 can be configured to have a selectable minimum split width 230w between spits 230 after crimping. This can be in the range of 0.001 to about 0.2 inches with specific embodiments of 0.002, 0.005, 0.010, 0.025, 0.050 or 0.1 inches.

In another embodiment for using the delivery balloon catheter to capture the fronds, a section of a balloon 241 (not shown) can be configured to evert or fold back over a proximal portion of the stent and thus overly and capture the fronds. When the balloon is inflated, the overlying section of balloon material unfolds, releasing the fronds. The everted section of balloon can over all or any selected portion of the fronds. Eversion can be facilitated through the use of preformed folds described herein, in the case, the folds having a circumferential configuration. The folded section of balloon can be held in place by a friction fit or through the use of releasable low-strength heat bond or adhesive known in the art for bonding the balloon to the fronds. In one embodiment for positioning the everted section, the balloon is positioned inside the scaffold section of the stent and then partially inflated to have an end of the balloon protrude outside of the scaffold section, then the balloon is partially deflated and everted section is rolled over the fronds and then the balloon is fully deflated to create a vacuum or shrink fit of the balloon onto the fronds.

Figure 5A:
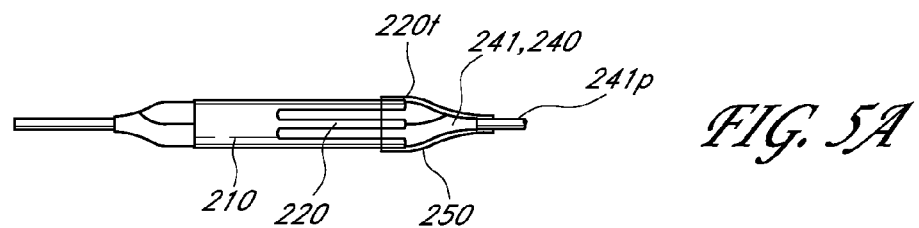
FIGS. 5A-5C are lateral views illustrating the deployment of stent fronds using an underlying deployment balloon and a retaining cuff positioned over the proximal portion of the balloon.
Figure 5B:
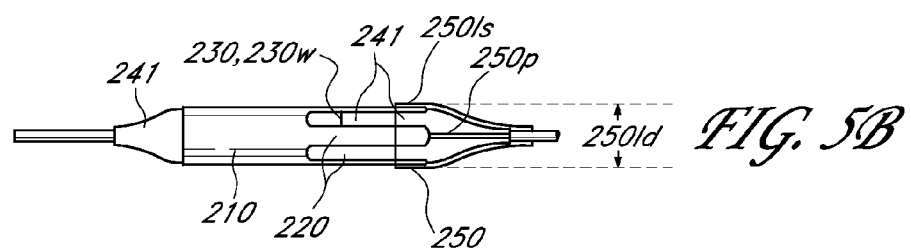
Figure 5C:
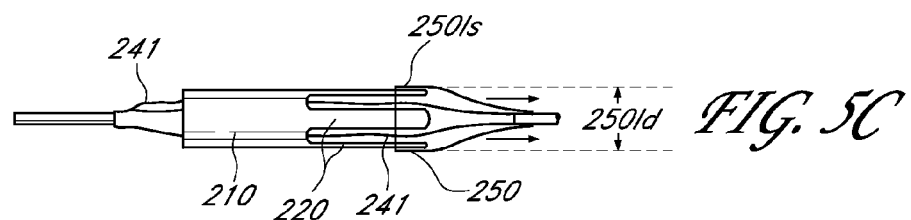

In various embodiments, fronds 210 can be captured by use of a tubular cuff 250 extending from the proximal end 241p of delivery balloon 241 as is shown in FIGS. 5A-5C. In one embodiment, the cuff is attached to the catheter at or proximal to the proximal end 241p of the delivery balloon. In alternative embodiments, the cuff can be attached to a more proximal section of the catheter shaft such that there is an exposed section of catheter shaft between balloon and the cuff attachment point with the attachment point selected to facilitate catheter flexibility. Alternatively, the cuff is axially movably carried by the catheter shaft, such as by attachment to a pull wire which extends axially along the outside of or through a pull wire lumen within the catheter shaft, or to a tubular sleeve concentrically carried over the catheter shaft. In either approach, the cuff is positionable during translumenal navigation such that it overlies at least a portion of the fronds 220.

After prosthesis 210 is positioned at the target vascular site, the stent region is deployed using the delivery balloon as described herein. The frond(s) can be released by withdrawal of the restraint. In most embodiments, the entire catheter assembly including the cuff or other restraint, balloon, and catheter shaft are withdrawn proximally to fully release the fronds. In alternative embodiment the cuff can be slidably withdrawn while maintaining position of the delivery balloon. This embodiment permits frond release prior to or after stent deployment.

Release of the fronds by the cuff can be achieved through a variety of means. In one embodiment, cuff 250 can be configured such that the proximal frond tips 220t, slip out from the cuff when the balloon is deployed. Alternatively, the cuff may be scored or perforated such that it breaks at least partially open upon balloon deployment so that it releases fronds 220. Accordingly, in such embodiments, cuff 250 can have one or more scored or perforated sections 250p. In such embodiments, portions of cuff 250 can be configured to break open at a selectable inflation pressure or at a selectable expanded diameter. In one embodiment, the cuff material can be fabricated from a polymer that it is more plastically deformable in a radial direction than axially. Such properties can be achieved by extrusion methods known in the polymer arts so as to stretch the material axially. In use, such materials allow the cuff to plastically deform in the radial when expanded by the deployment balloon, and then to stay at least partially deformed when the balloon is deflated so as to still cover the fronds. An example of such a material includes extruded Low density Polyethylene (LDPE). Further description of the use of the cuff 250 and other capture means may be found in U.S. patent application Ser. No. 10/965,230 which is fully incorporated by reference herein.

In various embodiments, cuff 250 can be configured such that it plastically deforms when the balloon is inflated and substantially retains its "inflated shape" 250is and "inflated diameter" 250id after the balloon is deflated is shown in FIGS. 5B and 5C. This can be achieved through the selection of plastically deformable materials for cuff 250 (e.g. plastically deformable polymers), the design of the cuff itself (e.g. cuff dimensions and shape) and combinations thereof. For example, a cuff fixed to a catheter shaft and having the same approximate internal diameter as the deployed stent may be folded over the stent fronds to constrain them (using conventional balloon folding techniques). That cuff may be unfolded when the stent deployment balloon is inflated and the fronds released. The cuff can be withdrawn along the balloon and catheter. In an alternative embodiment of a folded-over cuff, the cuff is relatively inelastic and has an internal diameter approximately that of the deployed stent.

Figure 6A:
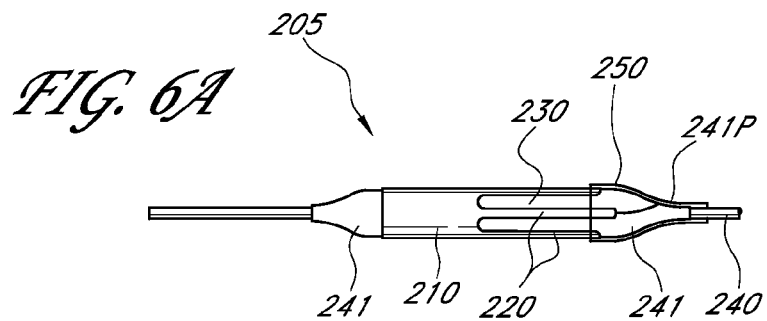
FIGS. 6A-6B are lateral views illustrating the change in shape of the cuff during deployment of a stent with fronds.
Figure 6B:
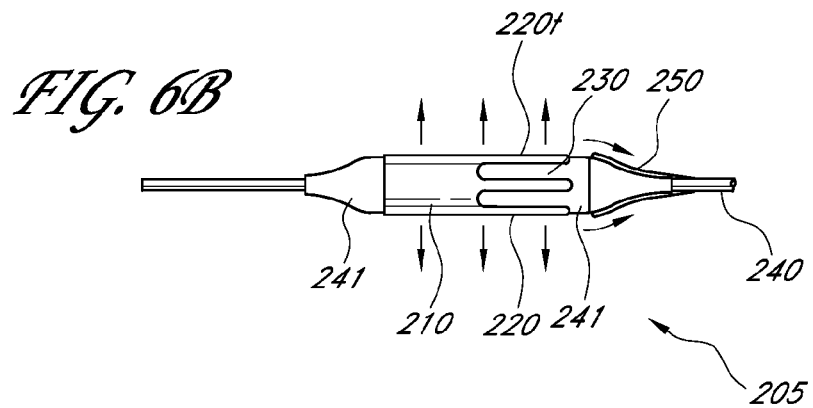

Also the cuff can be configured such that it shortens axially as it is expanded by the deployment balloon or other expansion device. This can be accomplished by selecting the materials for cuff 250 such that the cuff shrinks axially when it is stretched radially as is shown in FIGS. 6A and 6B. Accordingly, in one embodiment, the cuff can be made of elastomeric material configured to shrink axially when stretched radially.

Figure 6C:
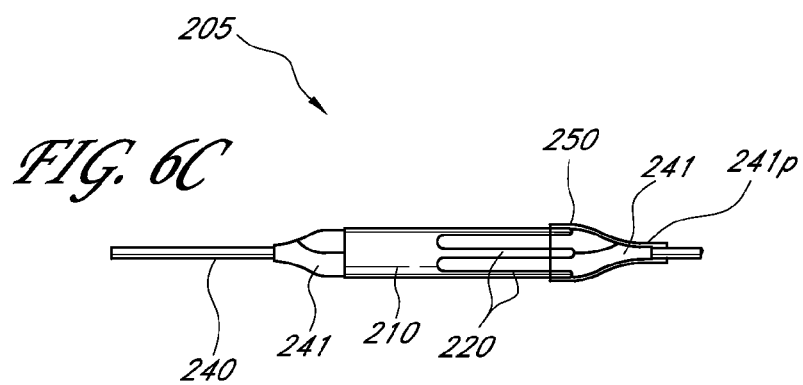
FIGS. 6C-6D are lateral views illustrating an embodiment of a cuff configured to evert upon balloon inflation to release the fronds.
Figure 6D:
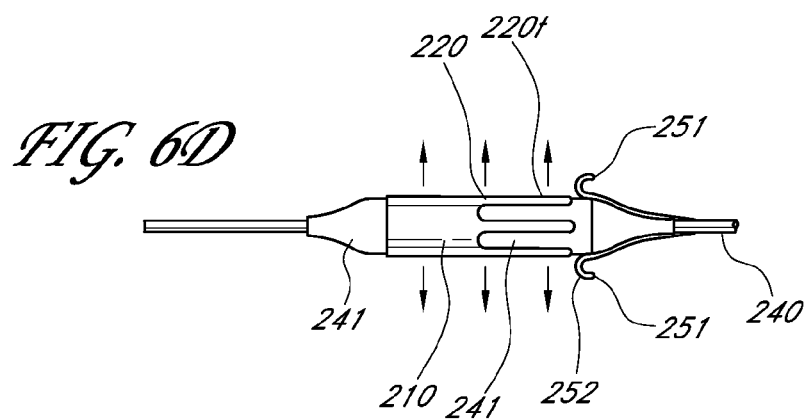

In another embodiment, all or a portion of the cuff can be configured to fold over or evert onto itself upon inflation of the balloon to produce an everted section 251 and so release the enveloped fronds as is shown in FIGS. 6C-6D. This can be facilitated by use of fold lines 252 described herein, as well as coupled the cuff to the balloon catheter. In one embodiment the cuff can be coaxially disposed over the proximal or distal end of the balloon catheter or even slightly in front of either end. This allows the cuff to disengage the fronds yet remain attached to the balloon catheter for easy removal from the vessel. In use, these and related embodiments allow the fronds to be held against the balloon to be radially constrained or captured during stent advancement and then easily released before, during or after balloon inflation to deploy the stent at the target site.

In various embodiments, all or a portion of cuff 250 can be fabricated from, silicones, polyurethanes (e.g., PEPAX) and other medical elastomers known in the art; polyethylenes; fluoropolymers; polyolefin; as well as other medical polymers known in the art. Cuff 250 can also be made of heat shrink tubing known in the art such as polyolefin and PTFE heat shrink tubing. These materials can be selected to produce a desired amount of plastic deformation for a selected stress (e.g. hoop stress from the inflation of deployment balloon). In particular embodiments, all or a portion of the materials comprising cuff 250 can be selected to have an elastic limit lower than forces exerted by inflation of the deployment balloon (e.g., the force exerted by 3 mm diameter balloon inflated to 10 atms). Combinations of materials may be employed such that different portions of the cuff (e.g., the proximal and distal sections or the inner and outer surfaces) have differing mechanical properties including, but not limited to, durometer, stiffness and coefficient of friction. For example, in one embodiment the distal portion of the cuff can high a higher durometer or stiffness than a proximal portion of the cuff. This can be achieved by constructing the proximal portion of the cuff from a first material (e.g., a first elastomer) and the distal portion out of a second material (e.g. a second elastomer). Embodiments of the cuff having a stiffer distal portion facilitate maintaining the fronds in a restrained state prior to deployment. In another embodiment, at least a portion of an interior surface of the cuff can include a lubricous material. Examples of suitable lubricious materials include fluoropolymers such as PTFE. In a related embodiment, a portion of the interior of the cuff, e.g., a distal portion, can be lined with lubricous material such as a fluoropolymer. Use of lubricous materials on the interior of the cuff aids in the fronds sliding out from under the cuff during balloon expansion.

Figure 7A:
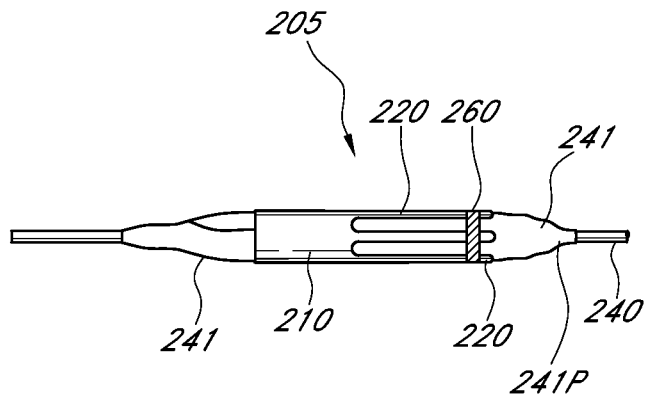
FIGS. 7A-7B are lateral views illustrating an embodiment of a tether for restraining the stent fronds.
Figure 7B:
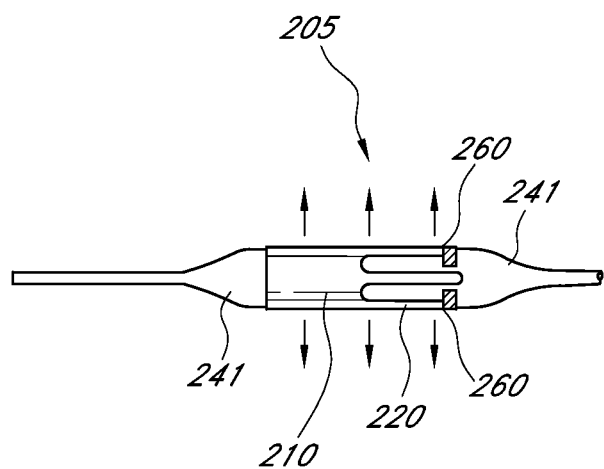

Referring now to FIGS. 7A-7B, in another embodiment for restraining the fronds, a tether 260 can be placed over all or portions of fronds 200 so as to tie the fronds together. Similar to the use of cuff 250, tether 260 can be released by the expansion of the balloon 241. Accordingly, all or a portion of the tether can be configured to plastically deform upon inflation of balloon 241 so as to release the fronds. Alternatively, the tether can be configured to be detached from the fronds prior to expansion of the balloon. In one embodiment, this can be achieved via a pull wire, catheter or other pulling means coupled to the tether directly or indirectly.

In various embodiments, the tether can be a filament, cord, ribbon, etc. which would simply extend around the fronds to capture them like a lasso. In one embodiment the tether can comprise a suture or suture-like material that is wrapped around the fronds. One or both ends of the suture tether can be attachable to a balloon catheter 241. In another embodiment, tether 260 can comprise a band or sleeve that fits over fronds 220 and then expands with expansion of balloon 241. In this and related embodiments, tether 260 can also be attached to balloon catheter 241. Also tether 260 can be scored or perforated so that a portion of the tether shears or otherwise breaks upon balloon inflation, thereby releasing the fronds. Further, the tether 260 can contain a radio-opaque other medical image visible marker 260m to allow the physician to visualize the position of the tether on the fronds, and/or determine if the tether is constraining the fronds.

Figure 8A:
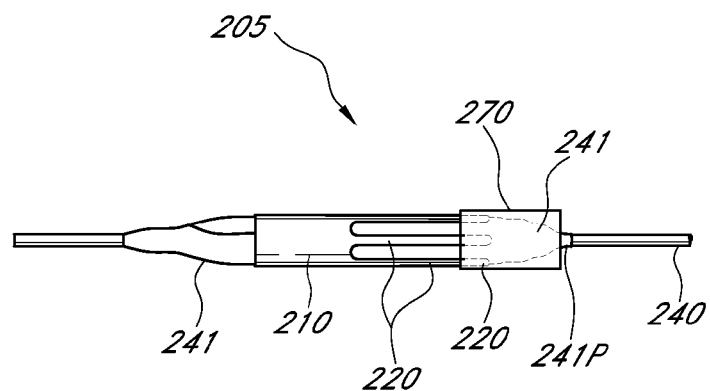
FIGS. 8A-8B are lateral views illustrating an embodiment of a proximally retractable sleeve for restraining the stent fronds.
Figure 8B:
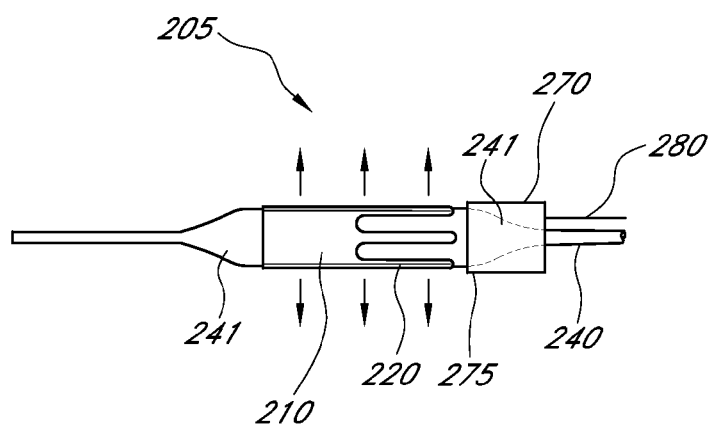

Referring now to FIGS. 8A-8B, in other embodiments of the delivery system 10, the fronds can be constrained through the use of a removable sleeve 270 that can be cover all or a portion of fronds 220 during positioning of the stent at the target tissue site and then be removed prior to deployment of the fronds. In one embodiment, sleeve 270 can be slidably advanced and retracted over stent 210 including fronds 220. Accordingly, all or portions of sleeve 270 can be made from lubricious materials such as PTFE or silicone. Sleeve 270 can also include one or more radio-opaque or other imaging markers 275 which can be positioned to allow the physician to determine to what extent the sleeve is covering the fronds. In various embodiments, sleeve 270 can be movably coupled to catheter 240 such that the sleeve slides over either the outer or inner surface (e.g., via an inner lumen) of catheter 240. The sleeve can be moved through the use of a pull ire, hypotube, stiff shaft or other retraction means 280 known in the medical device arts. In one embodiment, sleeve 270 can comprise a guiding catheter or overtube as is known in the medical device arts.

Figure 9A:
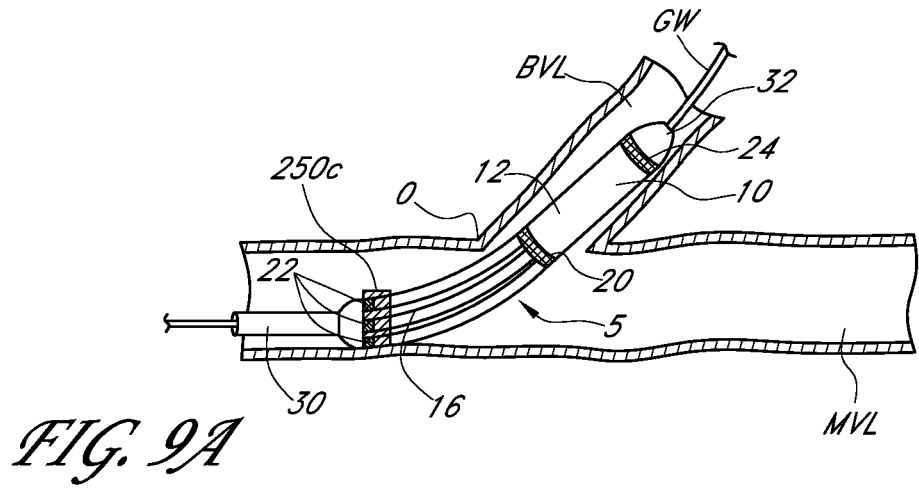
FIGS. 9A-9B, 10A-10B and 11A-11B illustrate deployment of a stent at an Os between a main blood vessel and a side branch blood vessel in accordance with the principles of the methods of the present invention.

Referring now to FIGS. 9A-11B, an exemplary deployment protocol for using delivery system 5 to deliver a prosthesis (10) having a stent region (12) and having one or more fronds (16) will be described. The order of acts in this protocol is exemplary and other orders and/or acts may be used. A delivery balloon catheter 30 is advanced within the vasculature to carry prosthesis 10 having and stent region (12) and fronds 16 to an Os O located between a main vessel lumen MVL and a branch vessel lumen BVL in the vasculature, as shown in FIGS. 9A and 9B. Balloon catheter 30 may be introduced over a single guidewire GW which passes from the main vessel lumen MVL through the Os O into the branch vessel BVL. Optionally, a second guidewire (not shown) which passes by the Os O in the main vessel lumen MVL may also be employed. Usually, the prosthesis 10 will include at least one radiopaque marker 20 on prosthesis 10 located near the transition region between the prosthesis section 12 and the fronds 16. In these embodiments, the radiopaque marker 20 can be aligned with the Os O, typically under fluoroscopic imaging.

Preferably, at least one proximal marker will be provided on the prosthesis at a proximal end of the transition zone, and at least one distal marker will be provided on the prosthesis at the distal end of the transition zone. Two or three or more markers may be provided within the transverse plane extending through each of the proximal and distal ends of the transition zone. This facilitates fluoroscopic visualization of the position of the transition zone with respect to the Os. Preferably, the transition zone is at least about 1 mm and may be at least about 2 mm in axial length, to accommodate different clinical skill levels and other procedural variations. Typically, the transition zone will have an axial length of no more than about 4 mm or 5 mm (for coronary artery applications).

Figure 10A:
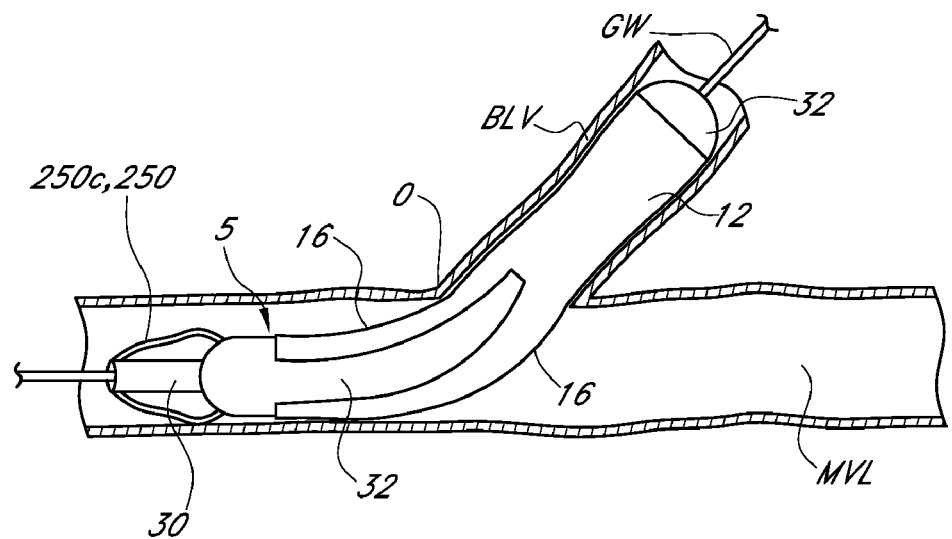
Figure 10B:
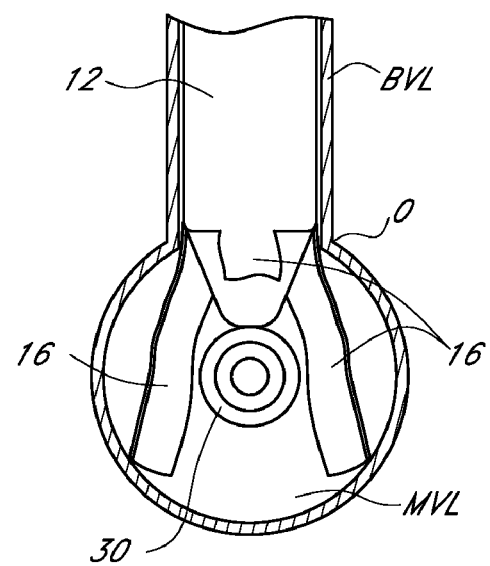

During advancement, the fronds are radially constrained by a constraining means 250c described herein (e.g., a cuff) to prevent divarication of the fronds from the delivery catheter. When the target location is reached at Os O or other selected location, the constraining means 250c is released by the expansion of balloon 32 or other constraint release means described herein (alternatively, the constraining means can be released prior to balloon expansion). Balloon 32 is then further expanded to expand and implant the support region 12 within the branch vessel lumen BVL, as shown in FIGS. 10A and 10B. Expansion of the balloon 32 also partially deploys the fronds 16, as shown in FIGS. 10A and 10B, typically extending both circumferentially and axially into the main vessel lumen MVL. The fronds 16, however, are not necessarily fully deployed and may remain at least partially within the central region of the main vessel lumen MVL. In another embodiment, the constraining means can be released after balloon expansion.

In another embodiment for stent deployment, after deploying stent 10, the cuff or other constraining means 250c need not be removed but can remain in position over at least a portion of the fronds so as to constrain at least the tip of the fronds. See, e.g., FIG. 12A, discussed in additional detail below. Then a main vessel stent 150 is advanced into the main vessel to at least partially overlap the fronds as described above. This method provides a reduced chance that the frond-tips will caught in or on the advancing main vessel stent 150 because the fronds are still captured under the cuff. After placement of stent 150 balloon 32 together the 12 stent portion of the side branch prosthesis is deployed by inflation of 30 balloon. Prosthesis delivery system including cuff 250*c* are removed (by pulling on catheter 30) to release the fronds which when released, spring outward to surround a substantial portion of the circumference of the main vessel stent 150 and the delivery procedures continues as described herein. This approach is also desirable in that by having the cuff left on over the fronds, the frond-tips are constrained together resulting in more advancement of the main vessel stent 150. This in turn can reduce procedure time and increase the accuracy and success rate in placement of the main vessel stent 150 particularly with severely narrowed, eccentric, or otherwise irregularly shaped lesions. In various embodiments, cuff 250*c* and/or proximal end of balloon 32 can have a selectable amount of taper relative to the body of the balloon to facilitate advancement of one or both of the main vessel stent 150 or stent 10 into the target tissue site when one device has already been positioned. Such embodiments also facilitate placement into severely narrowed vessels and/or vessels with irregularly shaped lesions.

Figure 11A:
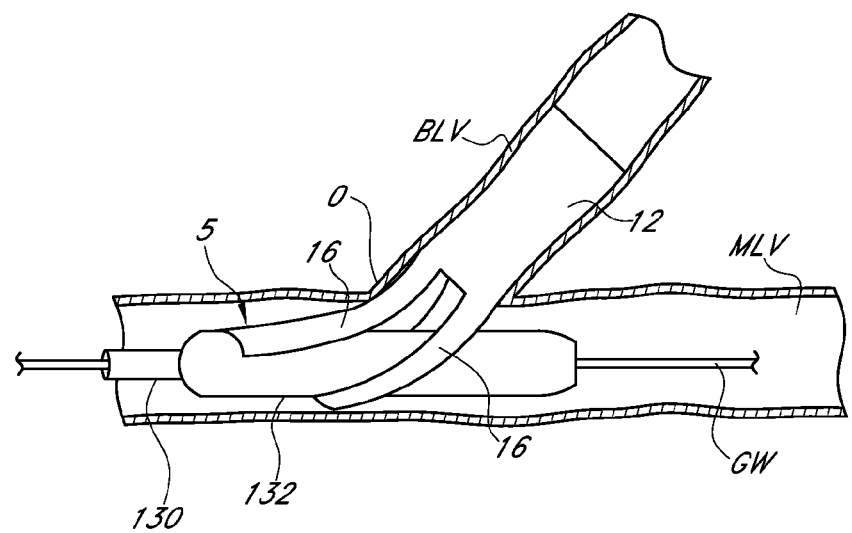
Figure 11B:
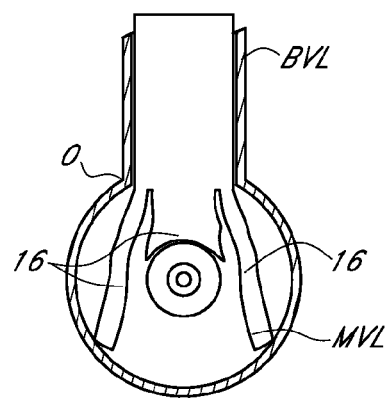

Various approaches can be used in order to fully open the fronds 16. In one embodiment, a second balloon catheter 130 can be introduced over a guidewire GW to position the second balloon 132 within the fronds, as shown in FIGS. 11A and 11B. Optionally, the first catheter 30 could be re-deployed, for example, by partially withdrawing the catheter, repositioning the guidewire GW, and then advancing the deflated first balloon 32 transversely through the fronds 16 and then re-inflating balloon 32 to fully open fronds 16. A balloon which has been inflated and deflated generally does not refold as nicely as an uninflated balloon and may be difficult to pass through the fronds. It will generally be preferable to use a second balloon catheter 130 for fully deforming fronds 16. When using the second balloon catheter 130, a second GW will usually be prepositioned in the main vessel lumen MVL past the Os O, as shown in FIGS. 11A and 11B. Further details of various protocols for deploying a prosthesis having a stent region (12) and fronds or anchors, such as prosthesis 10, are described in co-pending application Ser. No. 10/807,643.

Figure 9B:
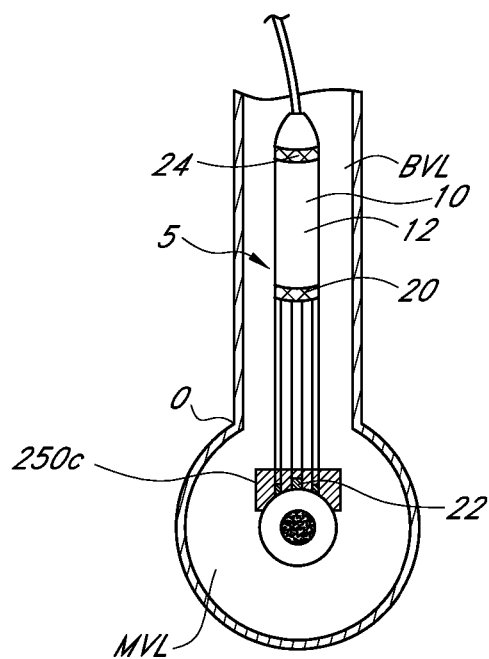

In various embodiments for methods of the invention using prosthesis/delivery system 5, the physician can also make use of additional markers 22 and 24 positioned at the proximal and distal ends of the prosthesis 10. In one embodiment, one or more markers 22 are positioned at the proximal ends of the fronds as is shown in FIGS. 9A and 9B. In this and related embodiments, the physician can utilize the markers to ascertain the axial position of the stent as well as the degree of deployment of the fronds (e.g., whether they are in captured, un-captured or deployed state). For example, in one embodiment of the deployment protocol, the physician could ascertain proper axial positioning of the stent by not only aligning the transition marker 20 with the Os opening O, but also look at the relative position of end markers 22 in the main vessel lumen MVL to establish that the fronds are positioned far enough into the main vessel, have not been inadvertently positioned into another branch vessel/lumen. In this way, markers 20 and 22 provide the physician with a more accurate indication of proper stent positioning in a target location in a bifurcated vessel or lumen.

In another embodiment of a deployment protocol utilizing markers 22, the physician could determine the constraint state of the fronds (e.g. capture or un-captured), by looking at the position of the markers relative to balloon 30 and/or the distance between opposing fronds. In this way, markers 22 can be used to allow the physician to evaluate whether the fronds were properly released from the constraining means prior to their deployment. In a related embodiment the physician could determine the degree of deployment of the fronds by looking at (e.g., visual estimation or using Quantitative Coronary Angiography (QCA)) the transverse distance between markers 22 on opposing fronds using one or medical imaging methods known in the art (e.g., fluoroscopy). If one or more fronds are not deployed to their proper extent, the physician could deploy them further by repositioning (if necessary) and re-expanding balloon catheters 30 or 130.

Figure 12A:
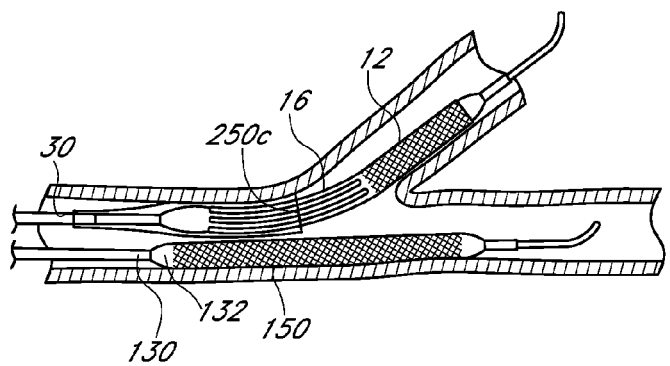
FIGS. 12A-12H are lateral and cross section views illustrating deployment of a stent having filament fronds an Os between a main blood vessel and a side branch blood vessel in accordance with the principles of the methods of the present invention.

Referring now to FIG. 12A-12I, an exemplary and embodiment of a deployment protocol using a deployment system 5 having a prosthesis 10 with fronds 16 will now be presented. As shown in FIG. 12A, prosthesis 10 is positioned at Os opening O with catheter 30 such that the stent section 12 is positioned substantially in branch vessel BV with the fronds 16 extending into the Os O and in the main vessel lumen MVL. In this embodiment a second delivery catheter 130 containing a stent 150 has been positioned in the MVL prior to positioning of catheter 30. Alternatively, catheter 130 can be positioned first and the branch vessel catheter 30 subsequently. In embodiments where catheter 130 has been positioned first, the proximal end of catheter 30 including fronds 16 can be positioned adjacent a proximal portion of balloon 132 of catheter 130 such that portions of captured fronds 16 and stent 150 are positioned side by side. Such alignment can be facilitated by lining up one or more radio-opaque markers (described herein) on the two catheters.

Figure 12B:
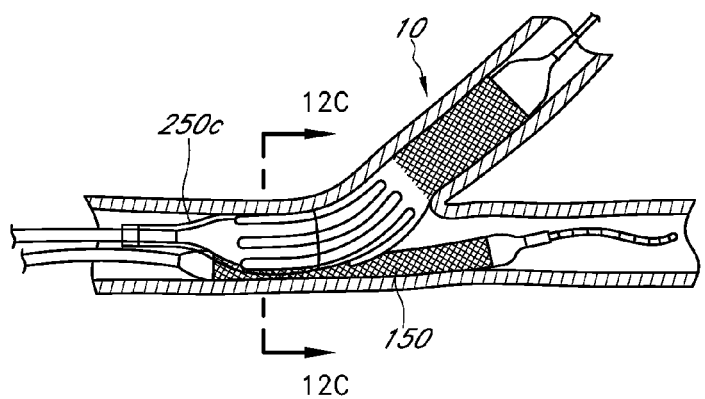
Figure 12C:
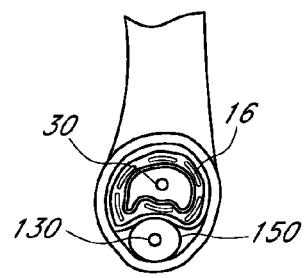
Figure 12D:
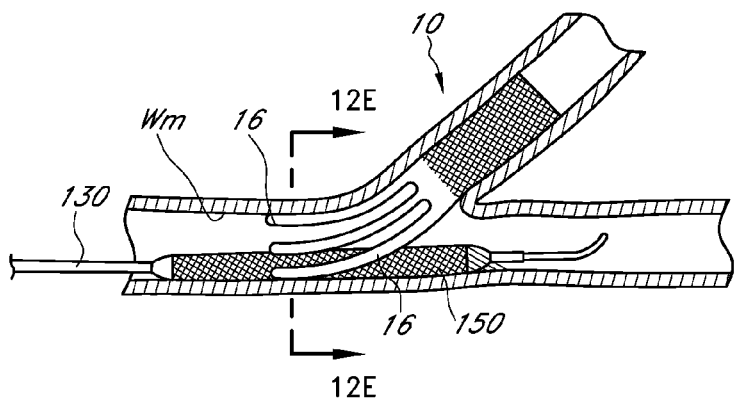
Figure 12E:
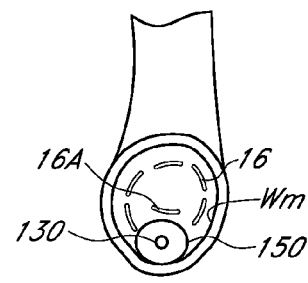

Next, as shown in FIGS. 12B-12C, balloon 32 of catheter 30 is expanded. Then as shown in FIGS. 12D-12E, catheter 30 together with cuff 250*c* is withdrawn from the vessel to uncover and release the fronds 16. When deployed, the fronds 16 are positioned between the vessel wall and stent 150 and substantially surround at least a portion of the circumference of the main vessel stent 150C/delivery system (130) as well as making contact with a substantial portion of inner wall Wm of main vessel lumen MVL. Preferably as shown in FIG. 12E, the fronds are distributed around the circumference of the Wall Wm. Also as shown in FIG. 12E one of the fronds 16A may bent back by stent 150, but may not be contacting the vessel wall.

Figure 12F:
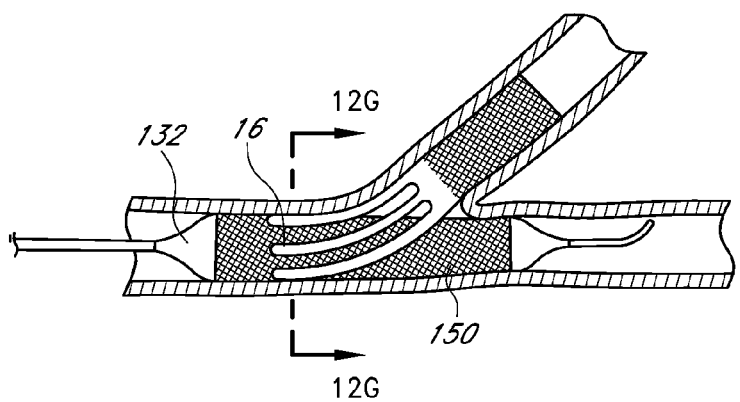
Figure 12G:
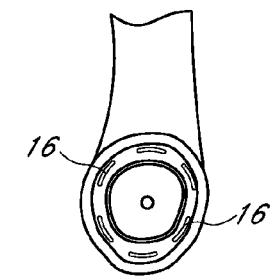
Figure 12H:
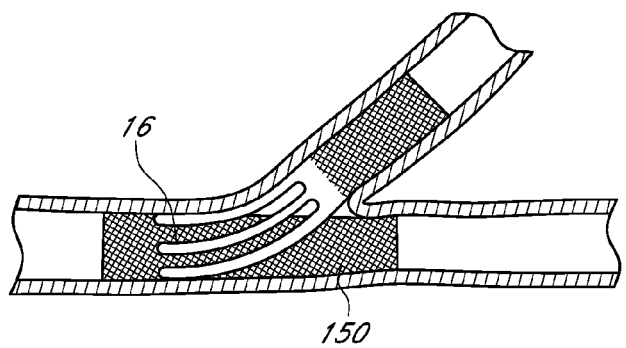

Then, as shown in FIGS. 12F-12H, balloon 132 is expanded to expand and deploy stent 150 after which the balloon is deflated and catheter 130 is withdrawn. Expansion of stent 150 serves to force and hold fronds 16 up against the vessel wall in a circumferential pattern as is shown in FIG. 12G. This essentially fixes the fronds in place between expanded stent 150 and the vessel wall. As such, the fronds may serve five functions, first, as an anchoring means to hold stent 12 in place in the branch vessel lumen BVL. Second they serve as a mechanical joining means to mechanically join stent 12 to stent 150. Third, to provide stent coverage to prevent prolapse of tissue into the lumen as well as in the case of a drug coated stent to deliver agent. Finally, they also provide additional mechanical prosthesising (hoop strength) to hold open Os of the branch vessel. More specifically, the now fixed fronds 16 can be configured to serve as longitudinal struts to more evenly distribute expansion forces over a length of the vessel wall as well as distribute compressive forces over a length of stent 12.

The prosthesis of the present invention, may be utilized in combination with either main vessel stents having a substantially uniform wall pattern throughout, or with main vessel stents which are provided with a wall pattern adapted to facilitate side branch entry by a guidewire, to enable opening the flow path between the main vessel and the branch vessel. Three examples of suitable customized stent designs are illustrated in FIG. 13A through 13C. In each of these constructions, a main vessel stent 110 contains a side wall 112 which includes one or more windows or ports 114. Upon radial expansion of the stent 110, the port 114 facilitates crossing of a guide wire into the branch lumen through the side wall 112 of the main vessel stent 110. A plurality of ports 114 may be provided along a circumferential band of the main vessel stent 110, in which instance the rotational orientation of the main vessel stent 110 is unimportant. Alternatively, as illustrated, a single window or port 114 may be provided on the side wall 112. In this instance, the deployment catheter and radiopaque markers should be configured to permit visualization of the rotational orientation of the main vessel stent 110, such that the port 114 may be aligned with the branch vessel.

In general, the port 114 comprises a window or potential window through the side wall which, when the main vessel stent 110 is expanded, will provide a larger window than the average window size throughout the rest of the stent 110. This is accomplished, for example, in FIG. 13A, by providing a first strut 116 and a second strut 118 which have a longer axial distance between interconnection than other struts in the stent 110. In addition, struts 116 and 118 are contoured to provide a first and second concavity facing each other, to provide the port 114.

Referring to FIG. 13B, the first strut 116 and second strut 118 extend substantially in parallel with the longitudinal axis of the stent 110. The length of the struts 116 and 118 is at least 2 times, and, as illustrated, is approximately 3 times the length of other struts in the stent. Referring to FIG. 13C, the first and second struts 116 and 118 are provided with facing concavities as in FIG. 13A, but which are compressed in an axial direction. Each of the foregoing configurations, upon expansion of the main vessel stent 110, provide an opening through which crossing of a guidewire may be enhanced. The prosthesis of the present invention may be provided in kits, which include a prosthesis mounted on a balloon catheter as well as a corresponding main vessel stent mounted on a balloon catheter, wherein the particular prosthesis and main vessel stent are configured to provide a working bifurcation lesion treatment system for a particular patient. Alternatively, prostheses in accordance with the present invention may be combined with separately packaged main vessel stents from the same or other supplier, as will be apparent to those of skill in the art.

Figure 13D:
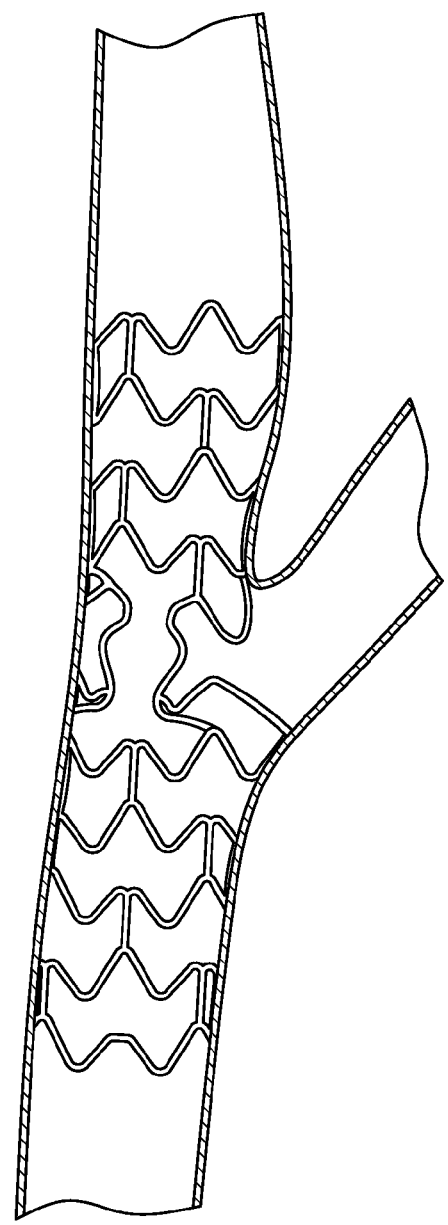
FIG. 13D is an image of a deployed main vessel stent having a side wall opening in alignment with a branch vessel.

FIG. 13D is an image of a main vessel stent having a side opening, deployed such that the side opening is aligned with the branch vessel lumen.

In accordance with a further aspect of the present invention, there is provided a stepped balloon for use with the prosthesis disclosed herein. The stepped balloon may be utilized for the initial implantation of the prosthesis, or for reconfiguring a previously implanted prosthesis as will be apparent to those of skill in the art.

Figure 15:
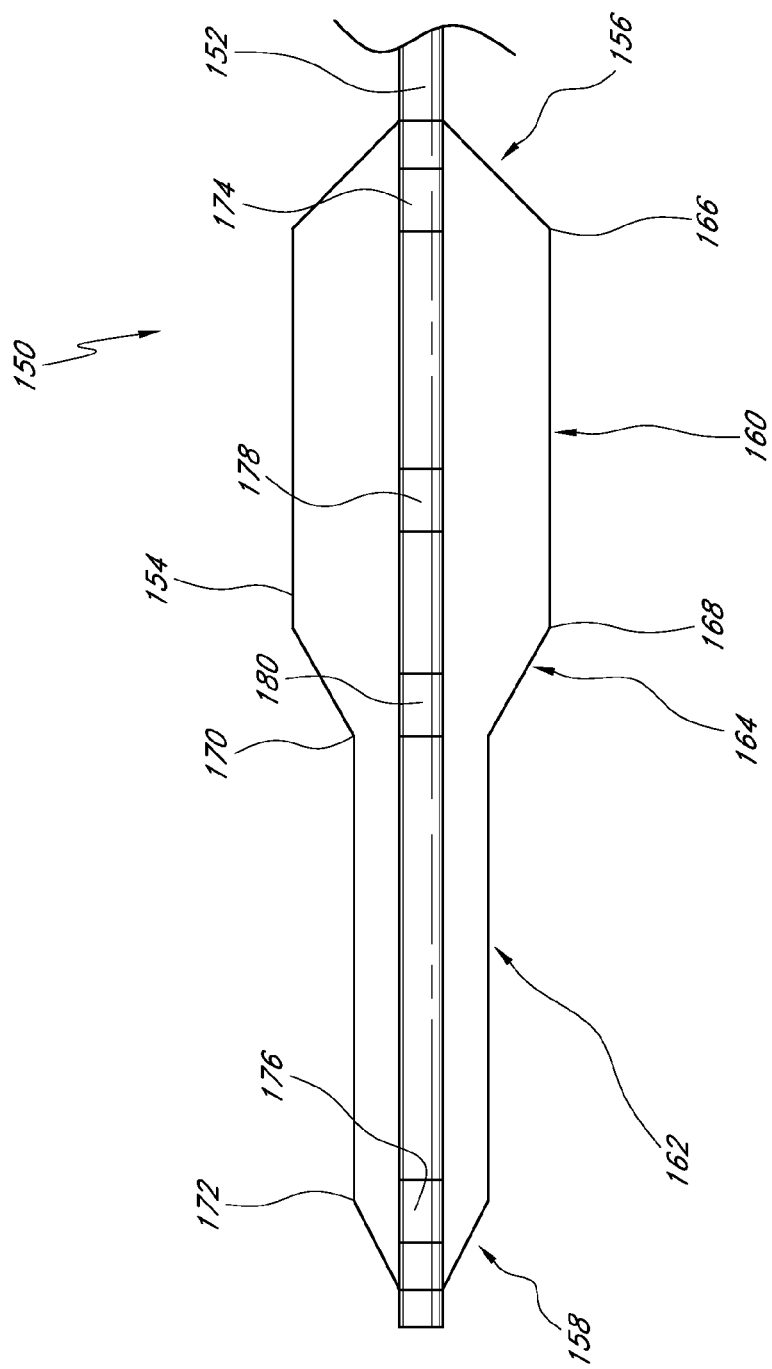
FIG. 15 is a schematic profile of a stepped balloon in accordance with one aspect of the present invention.

Referring to FIG. 15, there is illustrated a schematic side view of a distal end section of a catheter 150 having an elongate flexible tubular shaft 152 with a stepped balloon 154 mounted thereon. The dimensions, materials and construction techniques for the catheter shaft 152 are well understood in the art, and discussed briefly elsewhere herein. In general, shaft 152 has an axial length sufficient to reach from the desired percutaneous access point to the treatment site, and will typically include at least one inflation lumen for placing the stepped balloon 154 in fluid communication with a source of inflation media, as well as a guidewire lumen for either over the wire or rapid exchange guidewire tracking.

The stepped balloon 154 extends between a proximal end 156 and distal end 158. The balloon 154 is necked down to the catheter shaft 152 at each of the proximal and distal ends, and secured to the shaft 152 using any of a variety of adhesives, thermal bonding, or other techniques well known in the art.

The stepped balloon is provided with a proximal zone 160 and a distal zone 162, separated by a transition zone 164. In the illustrated embodiment, the proximal zone 160 has a greater inflated diameter than the distal zone 162. Alternatively, the relative dimensions may be reversed, such that the distal zone 162 has a greater inflated diameter than the proximal zone 160, such as for use in a retrograde catheterization from the branch vessel into the main vessel.

The diameters and lengths of the proximal zone 160 and distal zone 162 may be varied considerably, depending upon the intended target site. In an implementation of the invention designed for use in the coronary artery, a proximal zone 160 may be provided with a diameter in the range of from about 3 mm to about 4 mm, and the distal zone 162 may have an inflated diameter in the range of from about 2 mm to about 3 mm. In one implementation of the invention, the proximal zone 160 has an inflated diameter of about 3.5 mm and the distal zone 162 has an inflated diameter of about 2.5 mm. In general, the inflated diameter of the proximal zone 160 will be at least 110% of the inflated diameter of the distal zone 162. In certain implementations of the invention, the inflated diameter of the proximal zone 160 will be at least 125% of the inflated diameter of the distal zone 162.

The proximal zone 160 has a working length defined as the axial length between a proximal shoulder 166 and a distal shoulder 168. The working length of the proximal zone 160 is generally within the range of from about 5 to about 30 mm, and, in one embodiment, is about 9 mm. The working length of the distal zone 162 extends from a proximal shoulder 170 to a distal shoulder 172. The working length of the distal zone 162 is generally within the range of from about 5 to about 20 mm, and, in one embodiment, is about 6 mm. In the illustrated embodiment, each of the proximal zone 160 and distal zone 162 has a substantially cylindrical inflated profile. However, noncylindrical configurations may also be utilized, depending upon the desired clinical result.

The configuration and axial length of the transition zone 164 may be varied considerably, depending upon the desired frond configuration and ostium coverage characteristics of the implanted prosthesis. In the illustrated embodiment, the transition zone 164 comprises a generally frustoconical configuration, having an axial length between proximal shoulder 170 of the distal zone 162 and distal shoulder 168 of the proximal zone 160 within the range of from about 1 to about 10 mm, and, in one embodiment, about 2.5 mm.

The transition zone of this balloon delineates the transition from one diameter to another. In one embodiment this transition zone may be 4 mm in length and ramp from 2.5 to 3.5 mm in diameter. This conical surface is used to mold or flare the ostium of the bifurcation from the smaller side branch to the larger main vessel. In this configuration this stepped balloon may be utilized for deploying the prosthesis. Used in this manner the leading and trailing surfaces are utilized to expand the device in the side branch and main vessel and the transition zone is used to flare the transition zone of the stent against the wall of the ostium.

The wall of the stepped balloon 154 may comprise any of a variety of conventional materials known in the angioplasty balloon arts, such as any of a variety of nylons, polyethylene terephthalate, various densities of polyethylene, and others known in the art. Material selection will be influenced by the desired compliancy and burst strength of the balloon, as well as certain manufacturing considerations.

The stepped balloon may be formed in accordance with techniques well known in the angioplasty arts. For example, stock tubing of the desired balloon material may be inflated under the application of heat within a Teflon lined capture tube having the desired stepped configuration. The proximal and distal ends may thereafter be axially stretched with the application of heat to neck down to a diameter which relatively closely fits the outside diameter of the elongate shaft 152.

Figure 16:
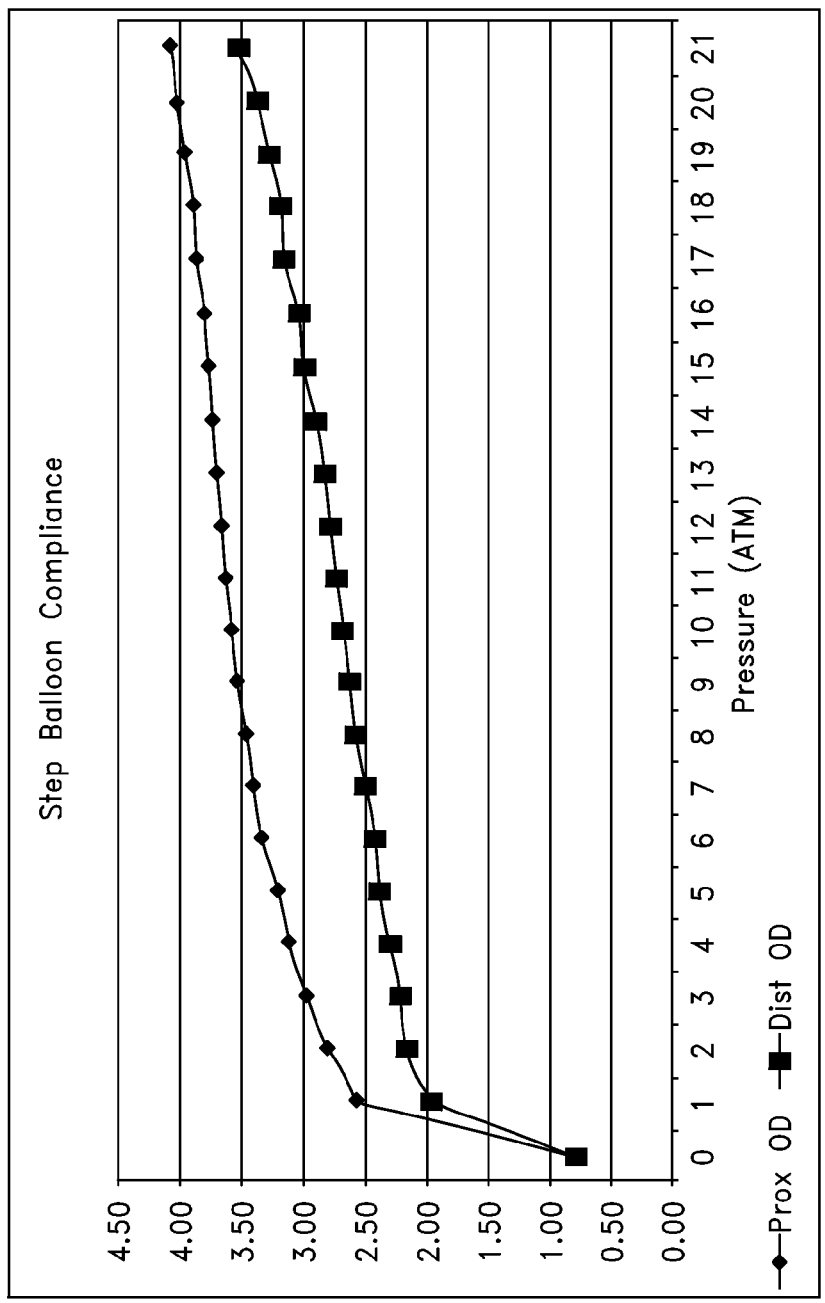
FIG. 16 is a balloon compliance curve for one embodiment of the stepped balloon in accordance with the present invention.

The balloon may be constructed such that it assumes the inflated stepped configuration at a relatively low inflation pressure. See, e.g., an exemplary compliance curve in FIG. 16. Alternatively, the balloon may be configured for sequential expansion, such as by allowing the distal zone 162 to inflate to its final outside diameter at a first pressure, to firmly position the branch vessel stent, and the proximal zone 160 only inflates to its final diameter at a second, higher inflation pressure, where a sequential deployment of the implant is desired.

In one embodiment the balloon is constructed such that it assumes the inflated stepped configuration upon inflation and retains this shape throughout its inflated working range (from initial inflation to rated burst pressure.) In this embodiment the balloon working range is from 1 ATM to 16 ATM at rated burst pressure.

In another embodiment the balloon is constructed such that it initially assumes the inflated stepped configuration within the lower pressures of its working range and trends to the same diameter at the higher pressures. The diameter of this balloon at higher pressure approximates that of the larger diameter in the stepped configuration.

In another embodiment the balloon is constructed such that it initially has a single diameter during the initial lower pressures of its working range and assumes its inflated stepped configuration at higher pressures. The diameter of the balloon at lower pressure approximates that of the smaller diameter in the stepped configuration.

Alternatively, the function of the stepped balloon 154 may be accomplished by providing two distinct balloons, 160' and 162'. The proximal balloon 160' may be inflated by a first inflation lumen (not illustrated) and the distal balloon 162' may be inflated by a second inflation lumen (not illustrated) extending throughout the length of the catheter shaft, to separate inflation ports. Inflation may be accomplished simultaneously or sequentially, depending upon the desired clinical procedure. Alternatively, a proximal balloon 160' and a distal balloon 162' may be both inflated by a single, common inflation lumen extending throughout the length of the catheter shaft.

The stepped balloon 154 is preferably navigated and positioned within the vascular system under conventional fluoroscopic visualization. For this purpose, the catheter 150 may be provided with at least one radiopaque marker. In the illustrated embodiment, a first radiopaque marker 174 is provided on the catheter shaft 152, at about the proximal shoulder 166. At least a second radiopaque marker 176 is provided on the shaft 152, aligned approximately with the distal shoulder 172. Proximal marker 174 and distal marker 176 allow visualization of the overall length and position of the stepped balloon 154.

In addition, a first transition marker 178 and second transition marker 180 may be provided on the shaft 152, at a location corresponding to a transition zone on the prosthesis. Transition markers 178 and 180 thus enable the precise location of the prosthesis transition with respect to the ostium between the main vessel and branch vessel, as has been discussed elsewhere herein. Each of the markers may comprise a band of gold, silver or other radiopaque marker materials known in the catheter arts.

In one embodiment of the stepped balloon 154 intended for use in the coronary artery, the axial length of the balloon between the proximal marker 174 and distal marker 176 is approximately 19.5 mm. The length between the distal marker 176 and transition marker 180 is approximately 6.1 mm. The distance between the transition markers 178 and 180, including the length of the transition markers, is about 4.5 mm. As will be apparent to those of skill in the art other dimensions may be utilized, depending upon the dimensions of the prosthesis and the target anatomy.

Figure 17:
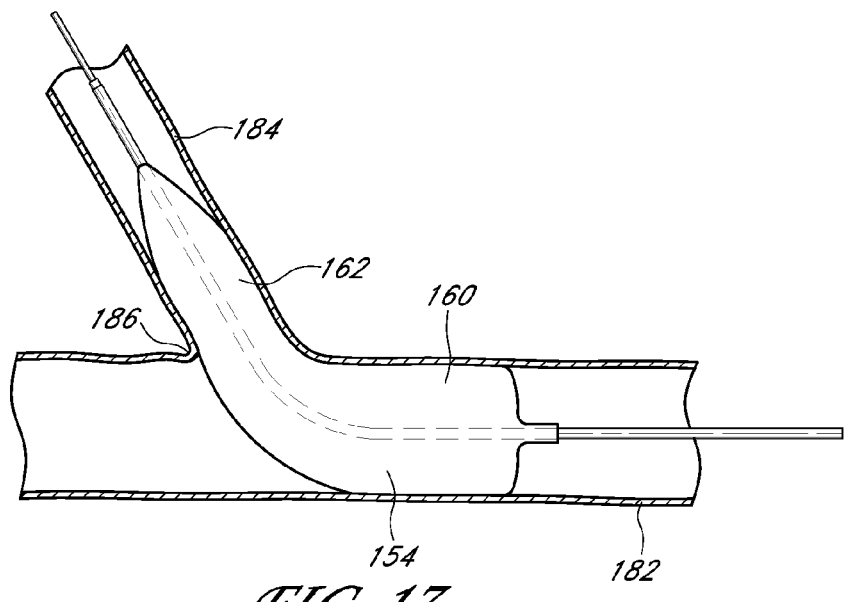
FIG. 17 is a schematic representation of a stepped balloon positioned within a vascular bifurcation.
Figure 18:
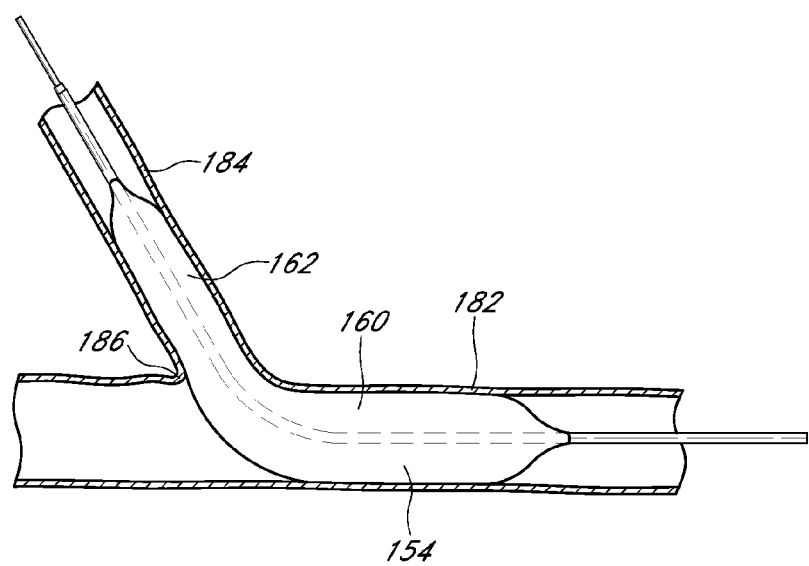
FIG. 18 is a schematic representation as in FIG. 17, with a different configuration of stepped balloon in accordance with the present invention.

Referring to FIGS. 17 and 18, there is schematically illustrated two different configurations of a stepped balloon 154 in accordance with the present invention, positioned and inflated within a treatment site at a vascular bifurcation, with the prosthesis omitted for clarity. In each, a stepped balloon 154 is positioned such that a proximal zone 160 is inflated within a main vessel 182. A distal zone 162, having a smaller inflated diameter than proximal zone 160, is positioned within the branch vessel 184. The stepped balloon 154 has been positioned to illustrate the relative location of the transition markers 178 and 180, with respect to the carina 186 of the bifurcation.

Figure 19:
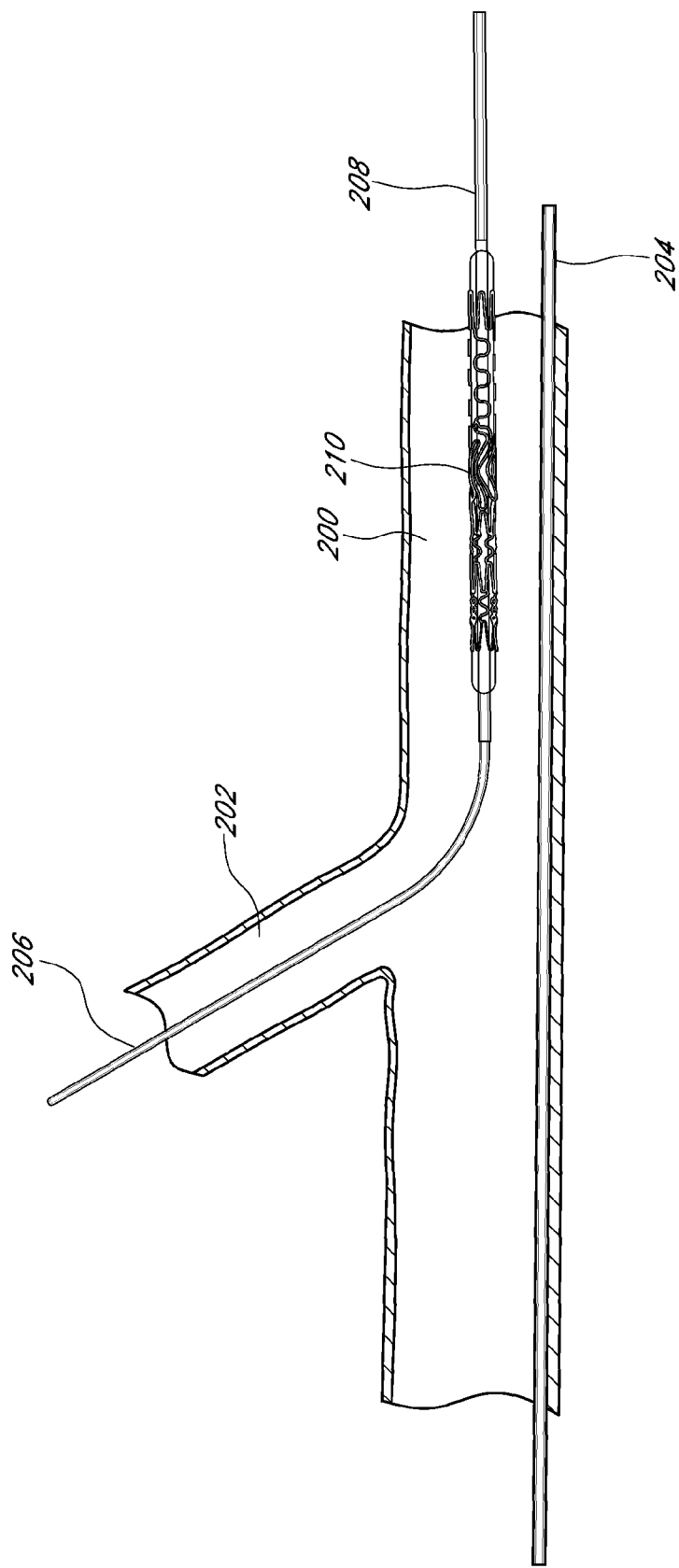
FIG. 19 is a first step in a deployment sequence using a stepped balloon and prosthesis in accordance with the present invention.

FIGS. 19 through 22 illustrate one application of the stepped balloon and prosthesis in accordance with the present invention. Referring to FIG. 19, there is illustrated a bifurcation between a main vessel 200 and a branch vessel 202. A main vessel guidewire 204 is illustrated as positioned within the main vessel, and a branch vessel guidewire 206 is in position extending from the main vessel 200 into the branch vessel 202.

A balloon catheter 208 carrying a prosthesis 210 is advancing along the branch vessel guidewire 206.

Figure 20:
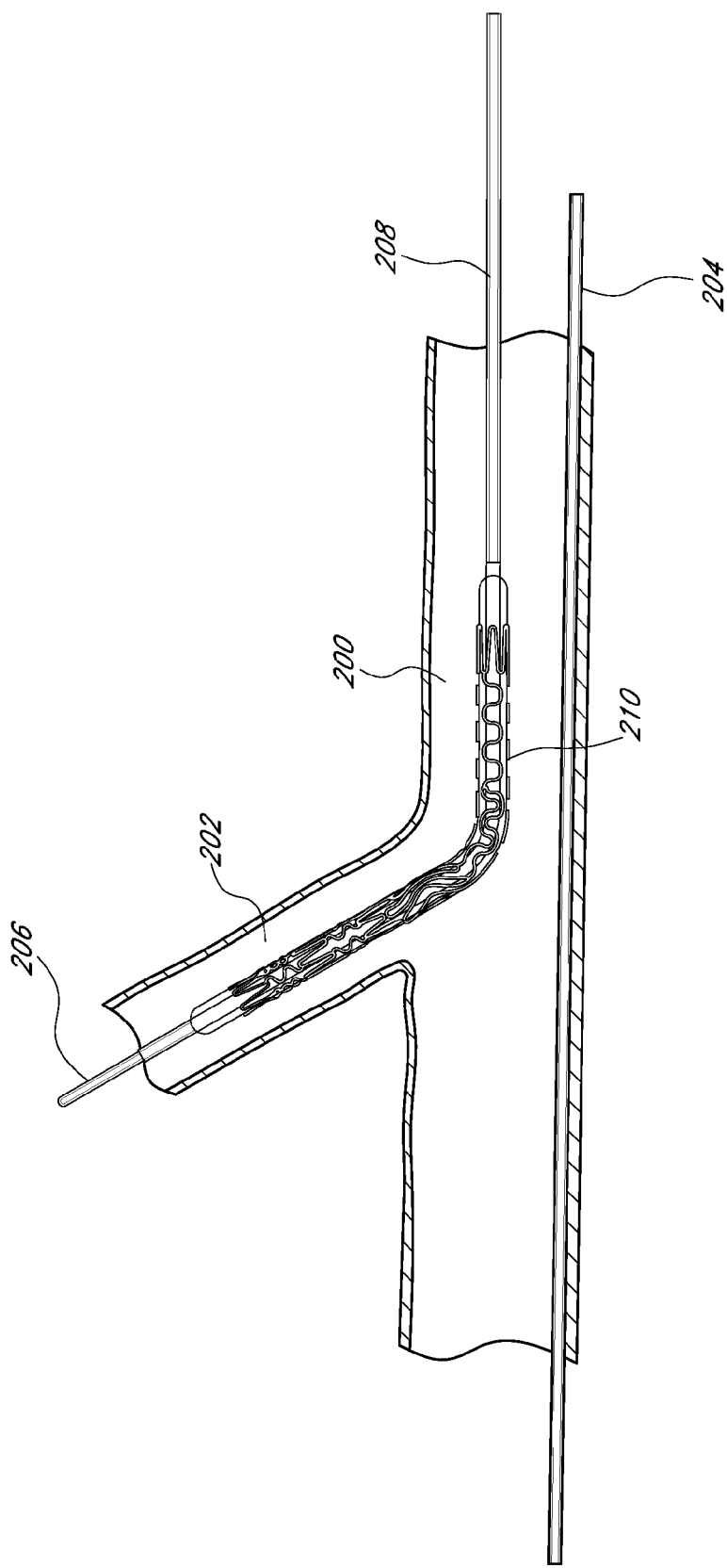
FIG. 20 is a second step in the deployment process disclosed in connection with FIG. 19, in which the prosthesis is positioned across the Os.

Referring to FIG. 20, the catheter 208 has advanced to the point of positioning the prosthesis 210 across the ostium between the main vessel 200 and branch vessel 202.

Figure 21:
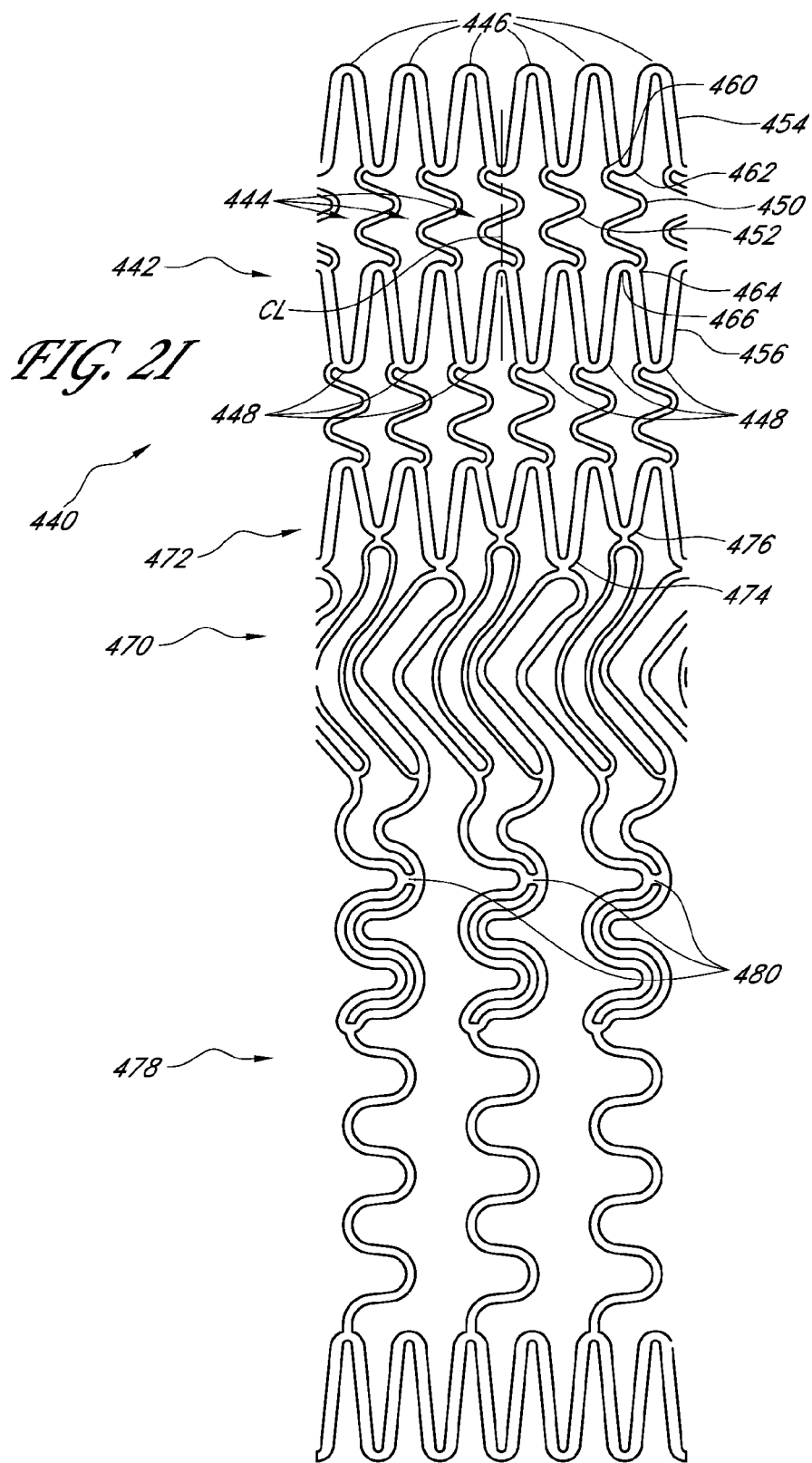
FIG. 21 is a third step in a deployment sequence, in which a prosthesis has been expanded utilizing a stepped balloon in accordance with the present invention.

Referring to FIG. 21, a stepped balloon 212 carried by the catheter 208 has been inflated across the ostium into the branch vessel 202. FIG. 22 illustrates the implanted prosthesis 210, after the balloon catheter 208 has been proximally retracted.

As can be seen from FIGS. 21 and 22, dilation of the stepped balloon 212 across the ostium enables expansion of the distal zone of the prosthesis in the branch vessel, the proximal zone of the prosthesis in the main vessel, and a transition zone of the prosthesis spans the ostium. The main vessel guidewire 204 may thereafter be proximally retracted to a point proximal to the prosthesis 212, and distally advanced through the proximal portion and the fronds of the prosthesis. A main vessel stent may thereafter be positioned in the main vessel 200 as has been discussed elsewhere herein.

Referring to FIGS. 23 and 24, there is illustrated a schematic representation of a distal portion of a stepped balloon catheter in accordance with the present invention. In general, the catheter includes a primary guidewire lumen as is understood in the art, such as for tracking the guidewire which extends into the branch vessel. Unlike previous embodiments disclosed herein, the catheter of FIGS. 23 and 24 includes a secondary guidewire lumen, such as for tracking the guidewire which extends into the main vessel lumen beyond the bifurcation.

Referring to FIG. 23, a catheter 220 extends between a proximal end 222 (not shown) and a distal end 224. A balloon 226 is carried in vicinity of the distal end 224, as is known in the balloon catheter arts. Balloon 226 may comprise a stepped balloon as has been described elsewhere herein, or a tapered balloon, or a conventional cylindrical angioplasty or stent deployment balloon, depending upon the desired performance.

The catheter 220 includes a guidewire lumen 228 which extends throughout the length of at least a distal portion of the catheter 220, to a distal port 230 at the distal end 224 of the catheter 220. In an embodiment intended for over-the-wire functionality, the first guidewire lumen 228 extends proximally throughout the length of the catheter, to a proximal manifold. In an alternate configuration intended for rapid exchange functionality, a proximal access port (not shown) provides access to the first guidewire lumen 228 at a point along the length of the catheter distal to the proximal end 222. In general, rapid exchange proximal access ports may be within the range of from about 10 cm to about 30 cm from the distal end 224.

As can be seen with reference to, for example, FIG. 23A, the catheter 220 is additionally provided with an inflation lumen 232 which extends throughout the length of the catheter to the proximal end 222. The distal end of inflation lumen 232 is in communication via an inflation port 234 with the interior of the balloon 226, to enable placement of the balloon 226 in fluid communication with a source of inflation media.

Referring to FIG. 23B, the catheter 220 is additionally provided with a second guidewire lumen 236. Second guidewire lumen 236 extends between a proximal access port 238 and a distal access port 240. The distal access port 240 is positioned proximally to the distal end 224 of the catheter 220. In the illustrated embodiment, the distal port 240 is positioned on the proximal side of the balloon 226. Generally, the distal port 240 will be no greater than about 4 cm, and often no greater than about 2 cm proximal of the balloon 226.

The proximal access port 238 may be provided on the side wall of the catheter, such as within the range of from about 10 cm to about 60 cm from the distal end 224. In one embodiment, the proximal access port 238 is within the range of from about 25 cm to about 35 cm from the distal end 224. The proximal port 238 is preferably spaced distally apart from the proximal end 222 of the catheter 220, to enable catheter exchange while leaving the main vessel guidewire in place as will be apparent in view of the disclosure herein.

As illustrated in FIG. 23, the second guidewire lumen 236 may be formed as an integral part of the catheter body. This may be accomplished by providing an initial 3 lumen extrusion having the desired length, and trimming away the wall of the second guidewire lumen 236 distally of the distal port 240 and proximally of the proximal port 238.

Alternatively, the second guidewire lumen 236 may be separately attached to a conventional catheter shaft such as is illustrated in FIG. 24. In this construction, the second guidewire lumen 236 is defined within a tubular wall 237, which may be a separate single lumen extrusion. The tubular wall 237 is positioned adjacent the catheter shaft, and bonded thereto using any of a variety of techniques known in the art, such as thermal bonding, adhesives, solvent bonding or others. Superior bonding and a smooth exterior profile may also be achieved by placing a shrink tube around the assembly of the catheter 220 and tubular wall 237, and heating the shrink tube to shrink around and combine the two structures as is well understood in the catheter manufacturing arts. It may be desirable to place a mandrel within the second guidewire lumen 236 and possibly also the first guidewire lumen 228 and inflation lumen 232 during the heat shrinking process.

Figure 25:
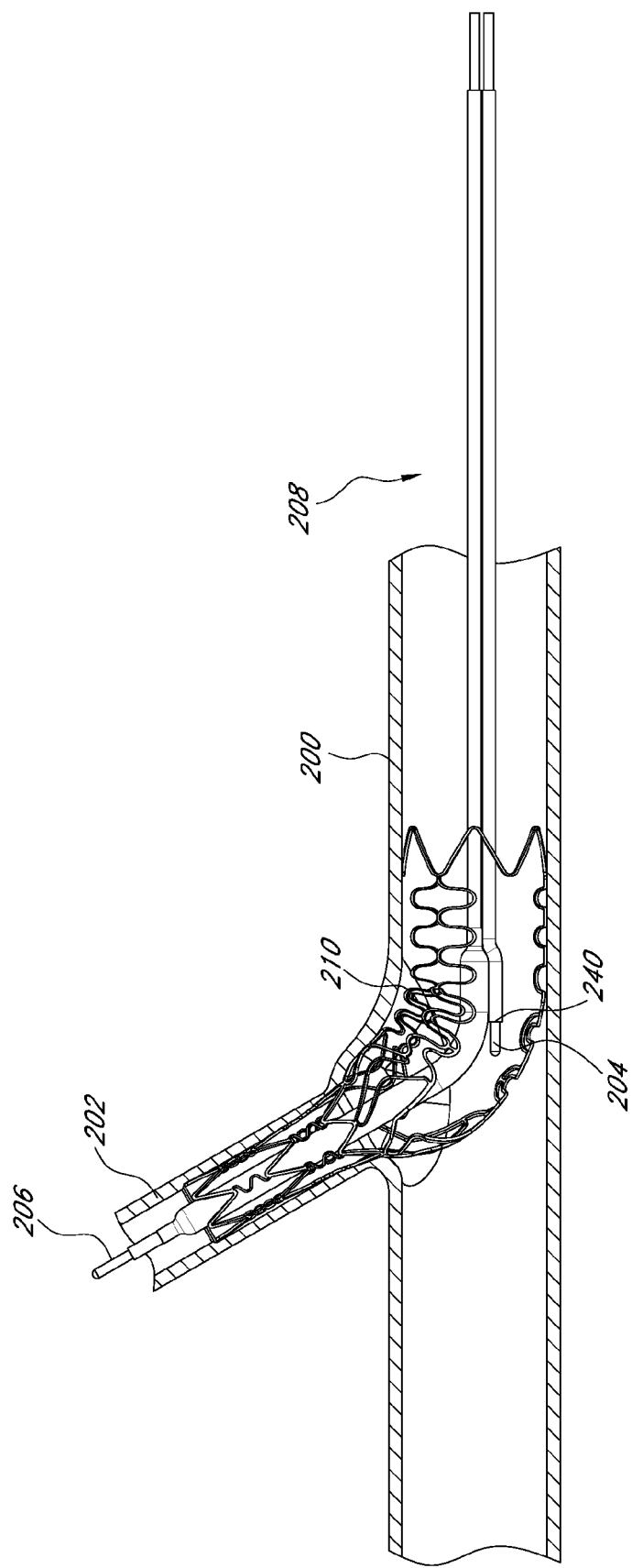
FIG. 25 is a schematic view of a two guidewire catheter in accordance with the present invention, in position at a vascular bifurcation.

In use, the second guidewire lumen 236 enables control over the main vessel guidewire. Referring to FIG. 25, there is illustrated a two guidewire catheter 208 in position across a bifurcation from a main vessel 200 into a branch vessel 202. The branch vessel guidewire 206 has been positioned in the branch vessel 202, and the catheter 208 advanced into position over the wire into the bifurcation. The prosthesis 210 is illustrated in its expanded configuration, and the balloon has been deflated.

Prior to percutaneously introducing the catheter into the patient's vasculature, the main vessel guidewire 204 is positioned within the secondary guidewire lumen 236, and the catheter and main vessel guidewire assembly is advanced as a unit along the branch vessel guidewire to the treatment site.

As seen in FIG. 25, the distal exit port 240 of the secondary guidewire lumen 236 is aligned such that the main vessel guidewire 204 is aimed down the lumen of the main vessel 200. In the illustrated embodiment, the secondary guidewire lumen is attached to the outside of the step balloon. The stent is crimped onto the step balloon, and the exit of the secondary guidewire lumen is between the intermediate zone and the circumferentially extending link of the prosthesis. In the crimped configuration, the distal exit 240 of the secondary lumen 236 resides between two adjacent fronds.

Following deployment of the stent and deflation of the balloon as illustrated in FIG. 25, the main vessel guidewire 204 may be distally advanced into the main vessel beyond the bifurcation, in between the two adjacent fronds. See, FIG. 26.

Figure 27:
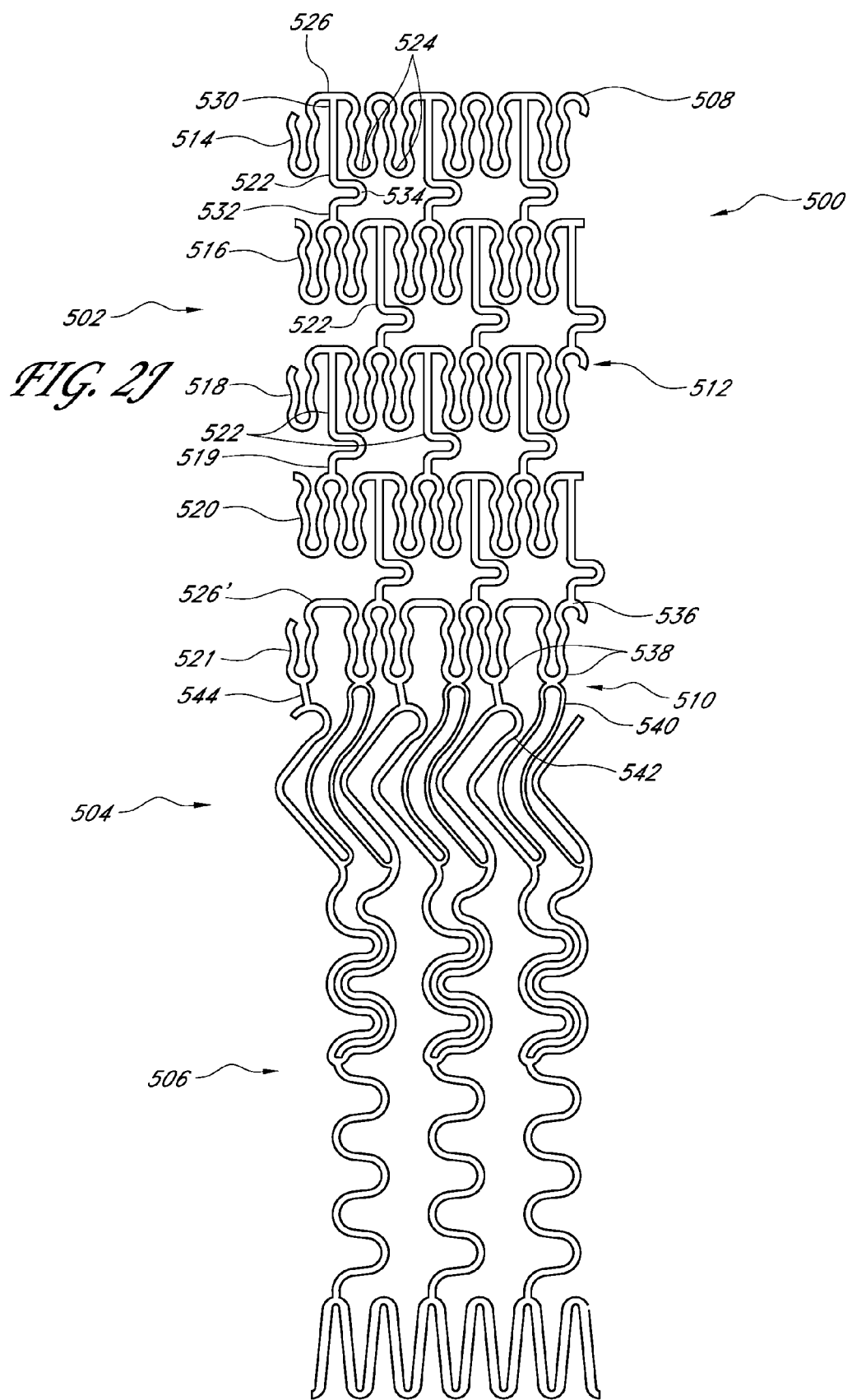
FIG. 27 is a schematic view as in FIG. 25, with a modified two guidewire catheter in accordance with the present invention.

Referring to FIG. 27, there is illustrated an embodiment similar to FIG. 25, except that the distal exit port 240 of the main vessel guidewire lumen 236 is positioned proximally of the balloon. The precise location of the distal exit 240 may be varied, so long as it permits direction of the main vessel guidewire distally within the main vessel beyond the bifurcation. In general, the distal exit 240 may be located within the axial length of the prosthesis as mounted on the catheter.

Following distal advance of the main vessel guidewire 204 into the main vessel distally of the bifurcation, the catheter 208 may be proximally withdrawn from the treatment site leaving the main vessel guidewire 204 in place. The catheter 208 may be removed from the main vessel guidewire 204 as is understood in the rapid exchange catheter practices, and a secondary catheter may be advanced down the main vessel guidewire such as to dilate an opening between the fronds into the main vessel beyond the bifurcation and/or deploy a second stent at the bifurcation as has been discussed herein.

Figure 26:
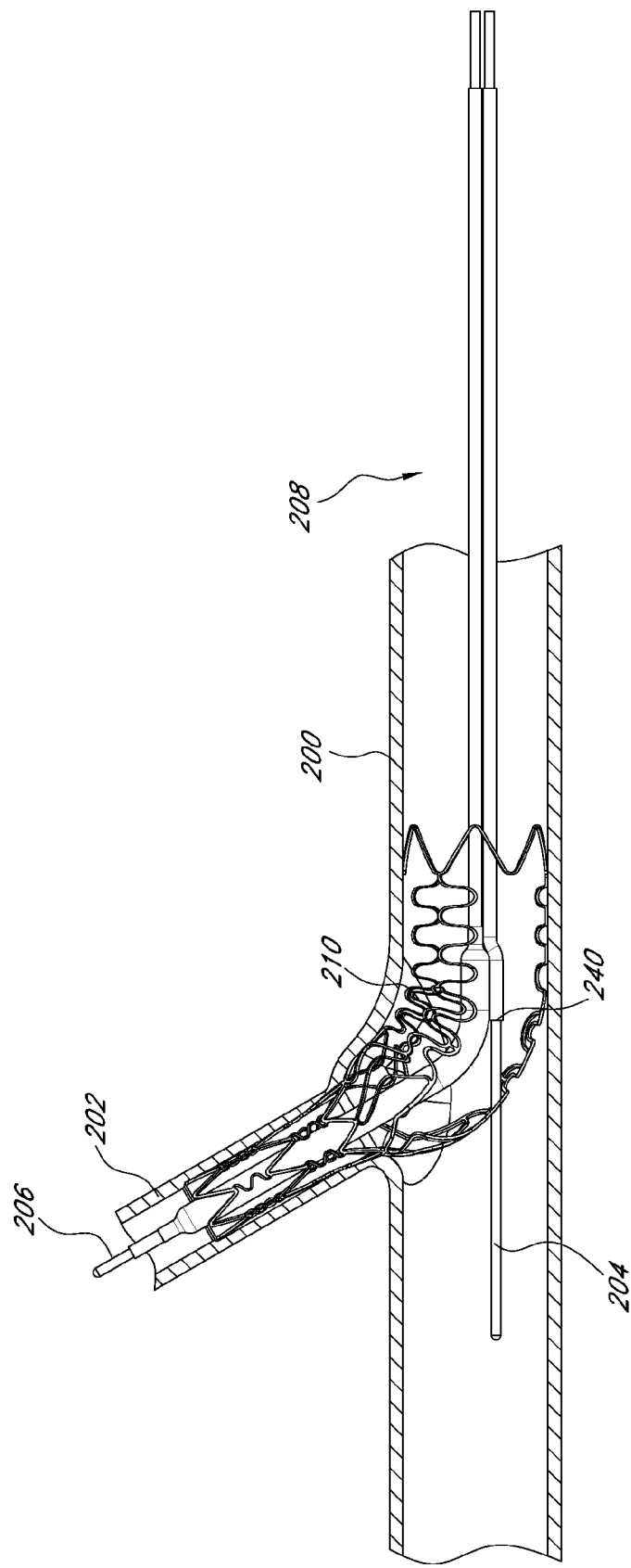
FIG. 26 is a schematic representation as in FIG. 25, showing the second guidewire advanced distally through the fronds.
Figure 27:
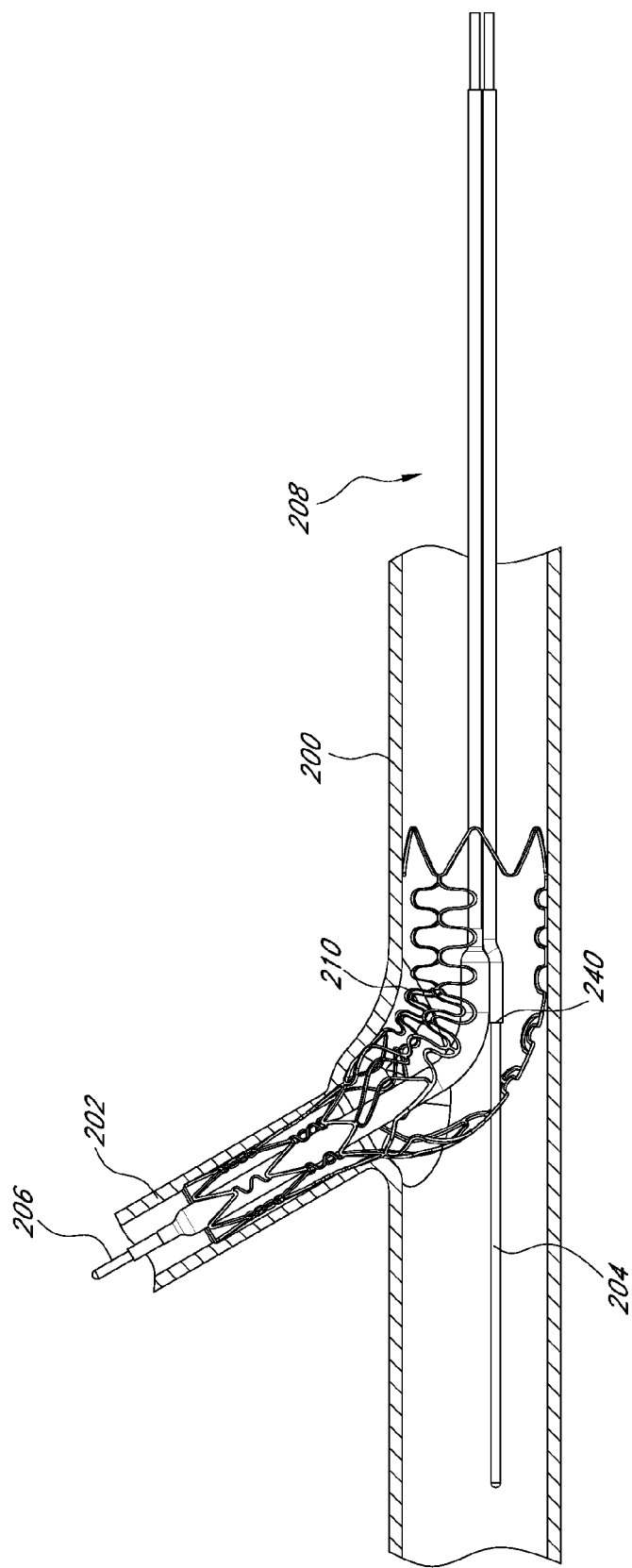

In FIGS. 25 through 27, the catheter 208 is schematically illustrated as a construct of a separate main vessel lumen attached to a catheter body. However, in any of the foregoing catheters the body construction may be that of a unitary extrusion as has been discussed previously.

The stepped balloon of the present invention may be used in a variety of additional applications. For example, the distal lower diameter section of the device may be used to slightly open a small blood vessel then the system advanced to treat the index lesion with an appropriately sized catheter. In one embodiment the stepped balloon may function as a standard PTCA catheter for the treatment of advanced cardiovascular disease. Specifically in cases where only a small diameter balloon catheter is capable of crossing a diseased lesion, the smaller diameter leading portion of the step balloon may be used to predilate the lesion. The catheter would then be deflated and the larger diameter trailing segment advanced across the lesion. The larger diameter portion of the stepped balloon would then be used to dilate the diseased lesion to a larger diameter. In this way the stepped balloon functions as both a pre-dilation and final dilation catheter.

Figure 28:
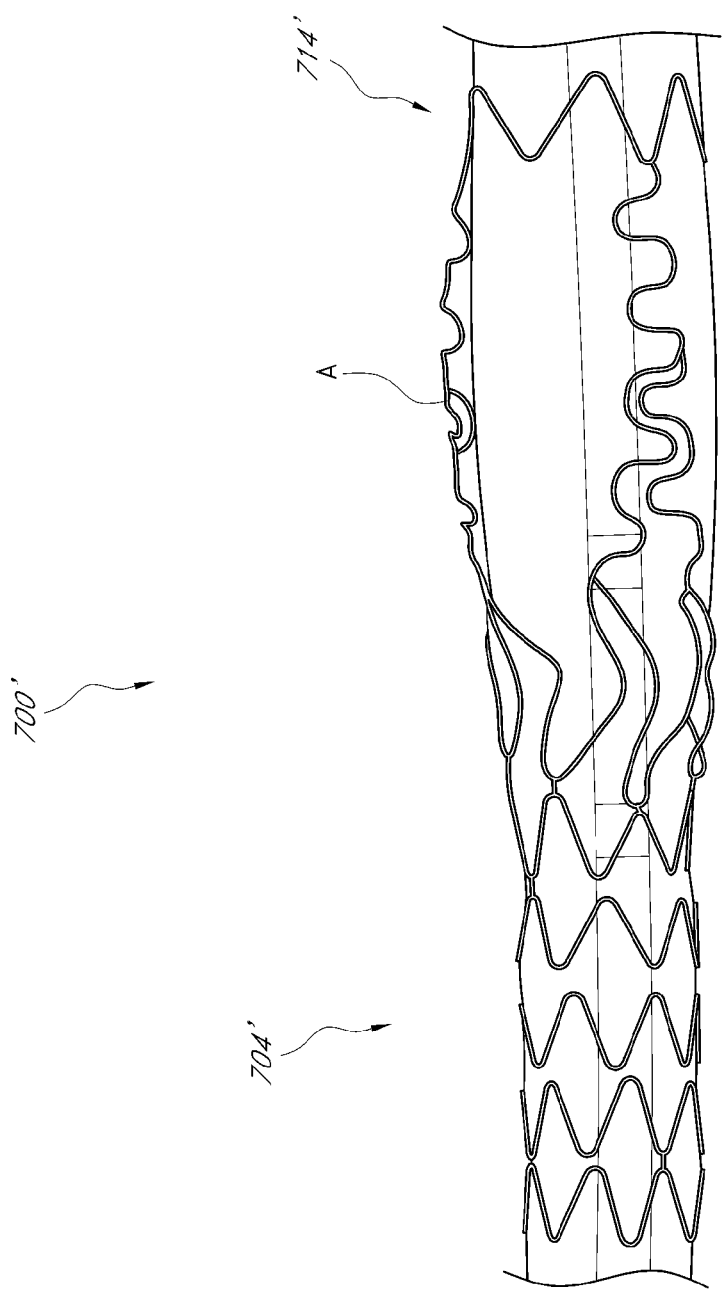
FIG. 28 is a plan view of a variation a prosthesis having a frond section similar to that of FIG. 2H mounted on a deployment device, the prosthesis being shown in an expanded configuration.
Figure 29:
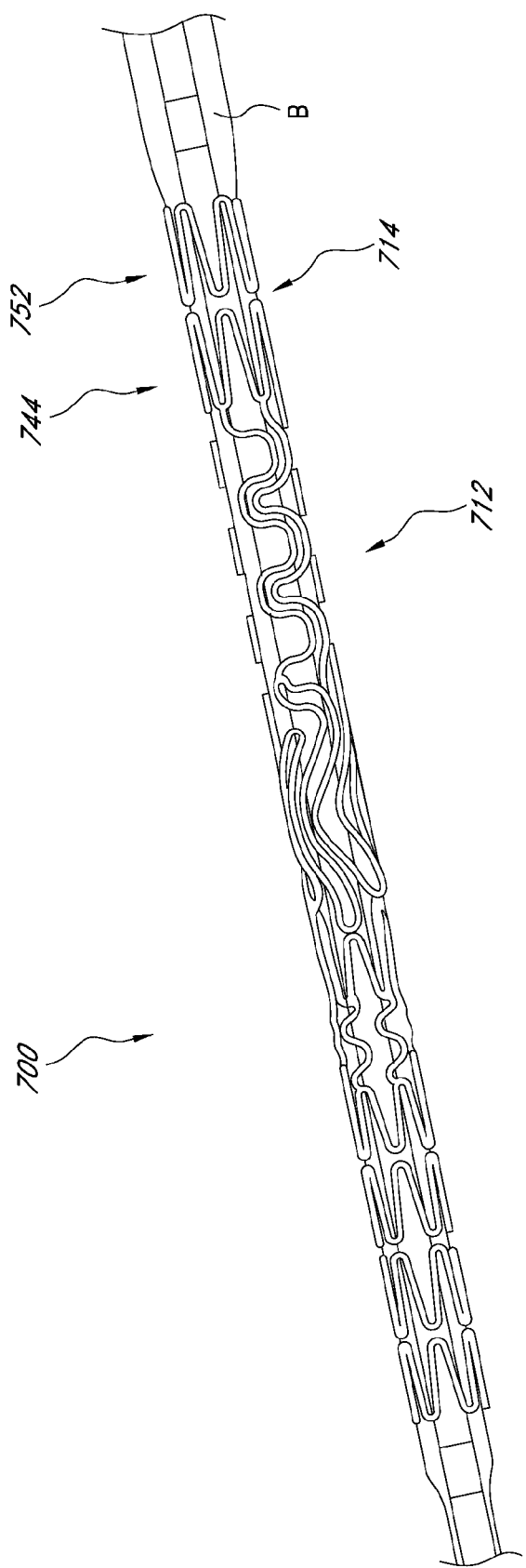
FIG. 29 is a lateral view of the prosthesis of FIGS. 2N-2O mounted on a deployment device in an unexpanded configuration.

FIGS. 28-29 illustrate some of the advantages of the link system 714 discussed above in connection with FIGS. 2N-2O. FIG. 28 shows the relationship of a prosthesis 700' that is similar to the prosthesis 700 except that the prosthesis 700' includes a circumferential link 714' with a single filament member extending circumferentially between each of a plurality of fronds. The prosthesis 700' is shown mounted on a delivery catheter that includes a balloon. The arrow A points to a portion of a frond that is lifting off of the balloon. This can be caused by a number of factors in use, such as a decrease in the distance between the link 714' and a stent section 704', with a lesser shortening of the frond. As can be seen, the frond is lifting away from the surface of the balloon in the middle of the frond. This lifting creates sufficient torque at the proximal end of the prosthesis 700' to deform the circumferential link 714' to some degree. Such deformation can cause the link 714' to be displaced into the central area of the prosthesis, which can cause problems for subsequent treatment steps, such as during introduction of a main vessel stent through the single filament link 714'.

FIG. 29 illustrates the prosthesis 700 with the link system 714 mounted on a balloon B. As discussed above, the frond engagement portion 744 is adapted to absorb a substantial amount of torque from the frond section 712 without transmitting it to the catheter securement portion 752. These structures lessen the deformation of the catheter securement portion 752 and the tendency of the catheter securement portion 752 to be displaced into the central area of the prosthesis 700. The frond engagement portion 744 helps to maintain the crimped profile of the fronds as the device navigates through tortuous vasculature such as the coronary arteries. The link system 714, particularly the frond engagement portion 744, helps to maintain the uniform spacing of the fronds during deployment. The catheter securement portion 752 facilitates re-entry into a guiding catheter, if required, by enhancing the force required to dislodge the prosthesis 700 during retraction based on surface area and frictional engagement between the link system 714 and the balloon. In addition, the effects of the motion of the fronds in the frond section 712 is primarily absorbed by the frond engagement portion 744 thus allowing the catheter securement portion 752 to maintain its crimped profile. Thus, subsequent steps of a procedure are facilitated, such as the passing of a main vessel stent through the proximal end of the prosthesis and through a side-wall opening defined between adjacent fronds, as described above.

Although the present invention has been described primarily in the context of a prosthesis adapted for positioning across the Os between a branch vessel and a main vessel prior to the introduction of the main vessel stent, in certain applications it may be desirable to introduce the main vessel stent first. Alternatively, where the prosthesis of the present invention is used provisionally, the main vessel stent may have already been positioned at the treatment site. The main vessel stent may include a side branch opening, or a side branch opening may be formed by advancing a balloon catheter through the wall of the stent in the vicinity of the branch vessel. Thereafter, the prosthesis of the present invention may be advanced into the main vessel stent, though the side wall opening, and into the branch vessel, with the circumferential link positioned within the interior of the main vessel stent. In many of the embodiments disclosed herein, the circumferential link will expand to a diameter which is approximately equal to the expanded diameter of the branch vessel support. Thus, upon initial deployment of the prosthesis, the circumferential link may be expanded to a diameter which is less than the adjacent diameter of the main vessel. If the prosthesis of the present invention is positioned within a previously positioned main vessel stent, it may therefore be desirable to include a post dilatation step to expand the circumferential link up to the inside diameter of the main vessel stent and also to deform the fronds outwardly and rotationally to conform to the interior surface of the main vessel stent.

While the above is a complete description of the preferred embodiments of the invention, various alternatives, modifications, and equivalents may be used. Also, elements or steps from one embodiment can be readily recombined with one or more elements or steps from other embodiments. Therefore, the above description should not be taken as limiting the scope of the invention which is defined by the appended claims.

What is claimed is:

1. A prosthesis for placement at an opening from a main body lumen to a branch body lumen, the prosthesis comprising:
 a radially expansible support configured to be deployed in at least a portion of the branch body lumen;
 a plurality of elongate members extending from an end of the support, the elongate members comprising a transition section comprising a plurality of spaced apart axially undulating filaments, the elongate members configured to be positioned across the opening and into the main body lumen;
 a plurality of elongate side wall spaces in between adjacent elongate members defined at least partially by a zone of the elongate members having an axially extending single filament having a first end connected to the transition section and a second end disposed proximal to the first end of the single filament, the spaces configured to receive a stent deployment device therethrough; and
 a circumferential link connected to the elongate members, the circumferential link spaced apart from the support by the elongate members, the circumferential link comprising a first portion located adjacent to proximal ends of the elongate members, and a second portion located on a proximal side of the first portion, the second portion configured to surround a space that can be occupied by at least a portion of an expansion device.

2. The prosthesis of claim 1, wherein the first portion comprises an undulating circumferentially expandable structure.

3. The prosthesis of claim 1, wherein the first portion comprises a plurality of peaks and valleys that are axially arranged.

4. The prosthesis of claim 3, wherein alternating peaks of the first portion are coupled with the proximal ends of the elongate members.

5. The prosthesis of claim 1, wherein the first portion is configured to absorb torque applied from the elongate members to isolate mechanically a distal portion of the second portion from the torque.

6. The prosthesis of claim 1, wherein the second portion comprises a circumferentially expandable structure.

7. The prosthesis of claim 1, wherein the second portion has an undulating configuration.

8. The prosthesis of claim 7, wherein the undulating pattern is out-of-phase with an undulating pattern of the first portion.

9. The prosthesis of claim 1 further comprising an axial coupling member disposed between the first portion and the second portion.

10. The prosthesis of claim 9, wherein the axial coupling member provides sufficient connection between the first portion and the second portion to resist premature expansion of a proximal portion of the first portion from a low profile configuration.

11. The prosthesis of claim 9, wherein the axial coupling member comprises a plurality of axially extending connectors.

12. The prosthesis of claim 11, wherein each connector connects a peak of the second portion with a valley of the first portion.

13. The prosthesis of claim 9, wherein the axial coupling member is a generally straight member.

14. The prosthesis of claim 9, wherein the axial coupling member has one or more undulations.

15. A prosthesis for placement at an opening from a main body lumen to a branch body lumen, the prosthesis comprising:
   a radially expansible support configured to be deployed in at least a portion of the branch body lumen, the support adapted to provide a radial force to support a first body lumen by a first density of struts;
   a plurality of elongate members extending from an end of the support, the elongate members each having a first end, a second end, and an axially extending undulating portion, at least a portion of the undulating portion having a second density of struts greater than the first density of struts of the support at least in the unexpanded state, the elongate members configured to be positioned across the opening and into a second body lumen; and
   a circumferential member connected to at least one of the elongate members, the circumferential member spaced apart from the support by the elongate members,
   wherein the axially extending undulating portion comprises a zone having a single filament, the single filament having a proximal end coupled with the circumferential member and a distal end disposed between the proximal end and the portion of the undulating portion having the second density of struts,
   wherein the circumferential member comprises an elongate member engagement portion adjacent to the second ends of the elongate members and a catheter securement portion located on a proximal side of the elongate member engagement portion.

16. The prosthesis of claim 15 further comprising an axially extending member disposed between the elongate member engagement portion and the catheter securement portion.

17. The prosthesis of claim 16, wherein the elongate member engagement portion and the catheter securement portion are undulating portions that extend circumferentially and out-of-phase with each other and wherein the axially extending member connects a trough of the elongate member engagement portion with a peak of the catheter securement portion.

18. A prosthesis for placement at an ostium opening from a first body lumen to a second body lumen, the prosthesis comprising:
   a radially expansible support having a first amount of material per unit area of support members, the support extending along a longitudinal axis and configured to be deployed in at least a portion of the first body lumen;
   at least one elongate member extending from an end of the support, the at least one elongate member configured to be positioned across the ostium opening, the elongate member including a first end with a transition portion coupled to apices on the support and a second end, the elongate member comprising a section with a single filament extending between the transition portion to the second end of the elongate member, the single filament having a distal end, a proximal end, and a longitudinal axis extending between the distal and proximal ends, the longitudinal axis of the single filament and the longitudinal axis of the radially expansible support being substantially parallel at least in an unexpanded state, wherein the transition portion has a second amount of material per unit area of support members different from the first amount of material per unit area at least in an unexpanded state; and
   a circumferential member connected to the at least one elongate member, the circumferential member spaced apart from the support by the at least one elongate member,
   wherein the circumferential member comprises a catheter securement portion located adjacent to the second end of the at least one elongate member that is spaced apart from the support and an elongate member engagement portion located adjacent the second end of the at least one elongate member that is spaced apart from the support, the elongate member engagement portion located between the catheter securement portion and the support, the catheter securement portion configured to surround a space that can be occupied by at least a portion of an expansion device;
   wherein the prosthesis is configured to receive a second prosthesis through the space surrounded by the catheter securement portion such that when the second prosthesis is deployed the at least one elongate member is entrapped between a vessel wall and the second prosthesis.

19. The prosthesis of claim 18 wherein the at least one elongate member is configured to be disposed in the second body lumen in an upstream or downsteam direction from the ostium when deployed.

20. The prosthesis of claim 18 further comprising an axial coupling member disposed between the elongate member engagement portion and the catheter securement portion.

21. The prosthesis of claim 20, wherein the elongate member engagement portion and the catheter securement portion are undulating portions that extend circumferentially and out-of-phase with each other and wherein the axial coupling member connects a trough of the elongate member engagement portion with a peak of the catheter securement portion.

22. A prosthesis for placement at an opening from a main body lumen to a branch body lumen, the prosthesis comprising:
   a radially expansible support adapted to provide a radial force to support a body lumen on a first side of the opening;
   at least two elongate, flexible members each having a first end, a second end, and an axially extending undulating portion, at least a portion of the undulating portion comprising a plurality of spaced apart axially undulating filaments, the elongate members extending from an end of the support and configured to be positioned across the ostium;
   at least one circumferential link being connected to the second ends of the elongate members, the circumferential link spaced axially apart from the support by the elongate members, wherein the circumferential link comprises an elongate member engagement portion, a catheter securement portion, and an axially extending member extending therebetween; and
   a plurality of elongate gaps in between adjacent elongate members defined at least partially by a zone of the elongate members having a single filament having a proximal end connected to the circumferential link and a distal end disposed distally of the proximal end of the single filament, the gaps configured to facilitate crossing of a second stent therethrough when the support is positioned on the first side of the opening and the circumferential link is positioned on a second side of the opening.

23. The prosthesis of claim 22, wherein the elongate member engagement portion and the catheter securement portion are undulating portions that extend out-of-phase and wherein the axially extending member connects a trough of the elongate member engagement portion with a peak of the catheter securement portion.

24. The prosthesis of claim 22, wherein the single filament comprises an undulating structure wherein the maximum angle of approach thereof does not exceed 45 degrees.

* * * * *

UNITED STATES PATENT AND TRADEMARK OFFICE
CERTIFICATE OF CORRECTION

| | | |
|---|---|---|
| PATENT NO. | : 8,382,818 B2 | Page 1 of 1 |
| APPLICATION NO. | : 12/829193 | |
| DATED | : February 26, 2013 | |
| INVENTOR(S) | : Davis et al. | |

It is certified that error appears in the above-identified patent and that said Letters Patent is hereby corrected as shown below:

On the Title Page
    In column 2 (page 3 item 56) at line 62, Under OTHER PUBLICATIONS, change "Catherization" to --Catheterization--.

In the Specifications
    In column 8 at line 11, change "the of" to --the--.
    In column 19 at line 41, change "polygluconate," to --polyglyconate,--.
    In column 29 at line 14, change "approaching)90°," to --approaching 90°),--.
    In column 29 at line 62, change "that that" to --that--.
    In column 31 at line 63, change "describe" to --described--.
    In column 40 at line 44, change "theses" to --these--.

In the Claims
    In column 56 at line 32, in Claim 19, change "downsteam" to --downstream--.

Signed and Sealed this
First Day of October, 2013

Teresa Stanek Rea
*Deputy Director of the United States Patent and Trademark Office*